(12) United States Patent
Stoit et al.

(10) Patent No.: US 8,084,473 B2
(45) Date of Patent: Dec. 27, 2011

(54) HETEROCYCLIC COMPOUNDS WITH AFFINITY TO MUSCARINIC RECEPTORS

(75) Inventors: Axel Stoit, Weesp (NL); Hein K. A. C. Coolen, Weesp (NL); Cornelis G. Kruse, Weesp (NL); Jan H. Reinders, Weesp (NL); Louise Terwel, legal representative, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 253 days.

(21) Appl. No.: 12/108,275

(22) Filed: Apr. 23, 2008

(65) Prior Publication Data

US 2009/0018160 A1    Jan. 15, 2009

Related U.S. Application Data

(60) Provisional application No. 60/913,584, filed on Apr. 24, 2007.

(51) Int. Cl.
| | |
|---|---|
| *C07D 413/00* | (2006.01) |
| *C07D 401/00* | (2006.01) |
| *A01N 43/40* | (2006.01) |
| *A61K 31/44* | (2006.01) |

(52) U.S. Cl. ............... 514/340; 514/341; 546/272.1; 546/275.4

(58) Field of Classification Search ............... 546/275.4, 546/272.1; 514/340, 341
See application file for complete search history.

(56) References Cited

U.S. PATENT DOCUMENTS 6,506,747 B1    1/2003    Betageri et al.

FOREIGN PATENT DOCUMENTS

| EP | 0 259 621 A2 | 3/1988 |
|---|---|---|
| EP | 0 296 721 A2 | 12/1988 |
| EP | 0 316 718 A2 | 5/1989 |
| WO | WO 03/037327 A1 | 5/2003 |
| WO | WO 2006/070198 A1 | 7/2006 |
| WO | WO 2008/129054 A2 | 10/2008 |

OTHER PUBLICATIONS

Del Giudice et al., Archiv der Pharmazie (Weinheim, Germany) (2003), 336(3), 143-154.*
International Preliminary Report on Patentability for PCT/EP2008/054897 dated Jul. 24, 2009 (14 pages).
International Search Report for PCT/EP2008/054897 dated Mar. 12, 2008 (published as WO 2008/129054 A3 on Feb. 5, 2009) (9 pages).
Clemo, G.R. et al., "The Synthesis of Pyridylpyrazoles," *J. Chemical Society* (1934), p. 1739, Beilstein Registry No. 15155.
Plate, R. et al., "Synthesis and In Vitro Muscarinic Activities of a Series of 3-(Pyrazol-3-y1)-1-azabicyclo[2.2.2]octanes," *Bioorganic & Medicinal Chemistry* (2000), vol. 8, pp. 449-454.
Plate, R. et al., "Synthesis and Muscarinic Activities of 3-(Pyrazolyl)-1,2,5,6-tetrahydropyridine Derivatives," *Bioorganic & Medicinal Chemistry* (1996), vol. 4, pp. 227-237.
Sauerberg, P. et al., "Novel Functional $M_1$ Selective Muscarinic Agonists. Synthesis and Structure Activity Relationships of 3-(1,2,5-Thiadiazolyl)-1,2,5,6-tetrahydro-1-methylpyridines," *J. Medicinal Chemistry* (1992), vol. 35, pp. 2274-2283.
Ward, J.S. et al., "Novel Functional $M_1$ Selective Muscarinic Agonists. 2. Synthesis and Structure-Activity Relationships of 3-Pyrazinyl-1,2,5,6-tetrahydro 1-methylpyridines. Construction of a Molecular Model for the $M_1$ Pharmacophore," *J. Medicinal Chemistry* (1992), vol. 35, pp. 4011-4019.
Zlotos, D.P. et al., "Muscarinic Receptor Agonists and Antagonists," *Expert Opinion on Therapeutic Patents* (1999), vol. 9, pp. 1029-1053.

* cited by examiner

*Primary Examiner* — Janet L. Andres
*Assistant Examiner* — Niloofar Rahmani
(74) *Attorney, Agent, or Firm* — Finnegan, Henderson, Farabow, Garrett & Dunner, L.L.P.

(57) ABSTRACT

The present invention relates to heterocyclic compounds of the formula (I)

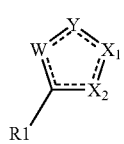

(I)

or a pharmaceutically acceptable salt, a solvate or hydrate thereof.

15 Claims, No Drawings

HETEROCYCLIC COMPOUNDS WITH AFFINITY TO MUSCARINIC RECEPTORS

This application claims the benefit of priority of U.S. Provisional Application No. 60/913,584, filed on Apr. 24, 2007, the disclosure of which is incorporated herein by reference.

FIELD OF THE INVENTION

This invention relates to new heterocyclic compounds having affinity to muscarinic receptors, a pharmaceutical composition containing said compounds, as well as the use of said compounds for the preparation of a medicament for treating, alleviating or preventing muscarinic receptor mediated diseases and conditions.

BACKGROUND OF THE INVENTION

Muscarinic cholinergic receptors mediate the actions of the neurotransmitter acetylcholine in the central and peripheral nervous systems. Muscarinic receptors comprise five distinct subtypes, denoted as muscarinic M1, M2, M3, M4 and M5 receptors. Each subtype has a unique distribution in the central and peripheral nervous systems. The M1 receptor is predominantly expressed in the cerebral cortex and is believed to be involved in the control of higher cognitive functions; the M2 receptor is the predominant subtype found in heart and is involved in the control of heart rate; the M3 receptor is widely expressed in many peripheral tissues and is believed to be involved in gastrointestinal and urinary tract stimulation as well as sweating and salivation; the M4 receptor is present in the brain and may be involved in locomotion and antipsychotic effects; the M5 receptor is located in the brain and may be involved in compound addition and in psychotic conditions such as schizophrenia. In view of the key physiological roles attributed to each of the muscarinic receptor subtypes, extensive efforts have been made to generate new compounds showing selective agonistic or antagonistic properties (see for example EP 0296721; EP 0316718; Sauerberg, P. et al., J. Med. Chem., 1992, Vol. 35, No. 22, 2274-2283; Ward, J. S. et al., 1992, J. Med. Chem., Vol. 35, No. 22, 4011-4019; U.S. Pat. No. 5,527,813; Zlotos, D. P. et al., Exp. Opin. Ther. Patents, Vol. 9, No. 8, 1999, 1029-1053; Plate, R., et al., Bioorg. Med. Chem. 4 (1996), 227-237; Plate, R. et al., Bioorg. Med. Chem. 8 (2000), 449-454; Del Guidice, M. R. et al., Arch. Pharm. Med. Chem. 2003, 336, 143-154).

A well known example of a M1/M4 preferring muscarinic receptor agonist is the thiadiazole compound xanomeline which in preclinical studies has a desirable profile, however, in clinical studies displays a unfavourable side effects (see for example the review by Eglen, R. M., *Progress in Medicinal Chemistry*, 2005, 43, p. 105-136 and U.S. Pat. No. 5,376,668), which seem to be related to M2 receptor mediated activity (e.g. heart rate effects). In addition, xanomeline has a relatively low (in vitro) metabolic stability. Xanomeline related compounds are further disclosed in U.S. Pat. No. 5,527,813. However, representative compounds display unfavourable side effects which seem to be related to M2 and M3 receptor mediated activity (e.g. heart rate effects and salivation, respectively).

Although further research is ongoing to develop therapeutics that have the selective M1/M4 profile, this has not yet resulted in successful candidates. Therefore, there is a need for new selective compounds with the desired properties.

DESCRIPTION OF THE INVENTION

It has now been found that heterocyclic compounds of the formula (I)

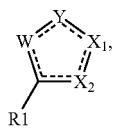

(I)

or a pharmaceutically acceptable salt, a solvate or hydrate thereof,
wherein
the heterocycle comprises two double bonds which may be present at varying positions, and which are represented by the dashed lines (—);
the heterocycle contains two heteroatoms,
W is N or NH;
Y is CH, O or NH, wherein
if Y is O, $X_1$ is CH and $X_2$ is C—Z—R2 or C—R3, wherein Z is NH, O, or S; and
if Y is CH or NH, one of $X_1$ and $X_2$ is CH or N, wherein if $X_1$ is CH or N, $X_2$ is C—Z—R2 or C—R3, and if $X_2$ is CH or N, $X_1$ is C—Z—R2 or C—R3, wherein Z is NH or S;
R1 is chosen from structures (a), (b) and (c):

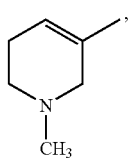

(a)

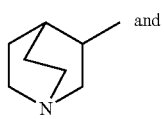

and (b)

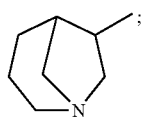

(c)

R2 is chosen from $(C_1-C_{10})$alkyl, $(C_2-C_{10})$alkenyl and $(C_2-C_{10})$alkynyl, optionally independently substituted with one or more substituents chosen from halogen, hydroxy, cyano, oxo, $(C_1-C_6)$alkoxy, $(C_1-C_6)$alkylthio, $(C_1-C_6)$alkenyloxy, $(C_1-C_6)$alkenylthio, $(C_1-C_4)$alkoxy$(C_1-C_4)$alkoxy, $(C_5-C_7)$cycloalkyl, a 5-membered unsaturated heterocycle (optionally substituted with halogen), phenyl, phenyloxy and phenylthio, wherein the phenyl group is optionally substituted with halogen; and R3 is chosen from $(C_4-C_{10})$alkyl, $(C_2-C_{10})$alkenyl and $(C_2-C_{10})$alkynyl, optionally independently substituted with one or more substituents chosen from halogen, hydroxy, cyano, $(C_1-C_6)$alkoxy, $(C_1-C_6)$alkylthio, $(C_1-C_6)$alkenyloxy, $(C_1-C_6)$alkenylthio, $(C_1-C_4)$alkoxy$(C_1-C_4)$alkoxy, $(C_5-C_7)$cycloalkyl, a 5-membered unsaturated heterocycle optionally substituted with halogen, phenyl, phenyloxy and phenylthio, wherein the phenyl group is optionally substituted with halogen;

and optionally, when R2 is an unbranched $(C_2-C_8)$alkyl, R2 links to formula (Ia)

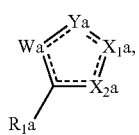

(Ia)

or a pharmaceutically acceptable salt, a solvate or hydrate thereof, through the $X_1a$ or $X_2a$ of formula (Ia), wherein if $X_1$ is CH or N, $X_1a$ is CH or N and $X_2a$ is C-Za-, or if $X_1$ is C—Z—R2, $X_1a$ is C-Za- and $X_2a$ is CH or N, wherein $X_1a$ or $X_2a$ having Za links to R2; and the symbols Wa, Ya and Za and the substituent R1a have the same meanings as defined previously for the symbols W, Y and Z and the substituent R1 and are not independently selected, each of the symbols Wa, Ya and Za and the substituent R1a representing identical symbols and substituents, respectively, as the symbols W, Y and Z and the substituent R1 in the other part of the structure of formula (I).

These heterocyclic compounds display affinity to muscarinic receptors, in particular to M1 and/or M4 receptors, having muscarinic receptor modulating, in particular (partially) agonistic, properties.

In addition, compounds of this invention display a higher (in vitro) metabolic stability than the prior art compound xanomeline.

The compounds of the invention are useful for treating, alleviating and preventing muscarinic receptor mediated diseases and conditions. Preferred compounds are M1 and M4 receptor agonists and may be used in the treatment of muscarinic M1/M4 mediated diseases and conditions, e.g.—but not limited to—Alzheimer's disease, cognitive impairment, Sjögren's disease, Schizophrenia and antinociception. In particular, the compounds of the present invention may be used to treat, alleviate or prevent cognitive impairment and psychotic disorders.

In an embodiment of the invention, the compounds have formula (I) wherein R2 is selected from $(C_1-C_{10})$alkyl, $(C_2-C_{10})$alkenyl and $(C_2-C_{10})$alkynyl, optionally independently substituted with one or more substituents selected from halogen, hydroxy, cyano, oxo, $(C_1-C_6)$alkoxy, $(C_1-C_6)$alkylthio, $(C_1-C_6)$alkenyloxy, $(C_1-C_6)$alkenylthio, $(C_1-C_4)$alkoxy$(C_1-C_4)$alkoxy, $(C_5-C_7)$cycloalkyl, a 5-membered unsaturated heterocycle (optionally substituted with halogen), phenyl, phenyloxy and phenylthio, wherein the phenyl group is optionally substituted with halogen. Preferably, R2 is selected from $(C_1-C_8)$alkyl, $(C_2-C_8)$alkenyl and $(C_2-C_8)$alkynyl, optionally independently substituted with one or more substituents selected from halogen, hydroxy, cyano, oxo, $(C_1-C_6)$alkoxy, $(C_1-C_4)$alkoxy$(C_1-C_4)$alkoxy, $(C_5-C_7)$cycloalkyl, tetrahydrofuranyl and phenyl, wherein the phenyl group is optionally substituted with halogen. In particular preferred are compounds of formula (I) wherein R2 is selected from $(C_1-C_8)$alkyl, $(C_2-C_8)$alkenyl, optionally substituted with one or more halogen or $(C_1-C_6)$alkoxy.

Further, in an embodiment of the invention, R3 is selected from $(C_4-C_{10})$alkyl, $(C_2-C_{10})$alkenyl and $(C_2-C_{10})$alkynyl, optionally substituted with a substituent selected from $(C_5-C_7)$cycloalkyl or phenyl, wherein the phenyl group is optionally substituted with halogen.

In a further embodiment of the invention, R1 has the structure (a) or (b), in particular (a).

In another embodiment, the compounds have formula (I) wherein W is N and Y is NH, in particular when $X_1$ is CH and $X_2$ is the residue C—Z—R2 or C—R3, and Z is O or S and preferably $X_2$ is the residue C—Z—R2. Z preferably is S.

In a further embodiment Y is O and Z is O or S, and preferably Z is S.

The term halogen refers to fluoro, chloro, bromo, or iodo. Preferred is fluoro.

The term $(C_1-C_{10})$alkyl means a branched or unbranched alkyl group having 1-10 carbon atoms, for example methyl, ethyl, propyl, isopropyl, butyl, n-pentyl, sec-pentyl, hexyl, octyl. In particular in the residue C—Z—R2 when Z is O or S, unsubstituted n-pentyl is a preferred alkyl group. Preferred substituted R2 alkyl groups are ethoxyethyl, when Z is O or S, and —$(CH_2)_3CF_3$ when Z is S.

The term $(C_1-C_6)$alkoxy means an alkoxy group having 1-6 carbon atoms, wherein the alkyl moiety is as defined above. The term $(C_1-C_6)$alkylthio has a similar meaning. The term $(C_1-C_4)$alkoxy$(C_1-C_4)$alkoxy means a $(C_1-C_4)$alkoxy group, the alkyl moiety of which is in turn substituted with $(C_1-C_4)$alkoxy.

The term $(C_2-C_8)$alkenyl means a branched or unbranched alkenyl group having 2-8 carbon atoms wherein the double bond(s) may be present at different parts of the group, for example vinyl, allyl, butenyl, n-pentenyl, sec-pentenyl, hexenyl, octenyl, etc. In the residue C—Z—R2, when Z is O or S, a preferred alkenyl group is 4-pentenyl and a preferred substituted alkenyl group is 4,4-difluoro-but-3-enyl.

The term $(C_1-C_6)$alkenyloxy means an alkenyloxy group having 1-6 carbon atoms, wherein the alkenyl moiety is as defined above. The term $(C_1-C_6)$alkenylthio has a similar meaning.

The term $(C_2-C_8)$alkynyl means a branched or unbranched alkynyl group having 2-8 carbon atoms wherein the triple bond(s) may be present at different parts of the group, for example ethynyl, propargyl, 1-butynyl, 2-butynyl, etc.

The term $(C_5-C_7)$cycloalkyl means a cyclic alkyl group having 5-7 carbon atoms, thus cyclopentyl, cyclohexyl, cycloheptyl or cyclooctyl.

The term 5-membered unsaturated heterocycle in the definition of R2 means a heterocycle containing 5 atoms, wherein at least one atom is a heteroatom selected from O, N and S, the other atoms being carbon atoms, wherein the heterocycle further at least contains one double bond. Examples are furanyl and pyrrolyl groups.

With reference to substituents, the term "independently" means that the substituents may be the same or different from each other.

The compounds of the invention may suitably be prepared by methods available in the art, and as illustrated in the experimental section of this description. Some novel and useful intermediates have been found for the preparation of the compounds of this invention.

Thus, another embodiment of the invention is a heterocyclic compound of the formula (II)

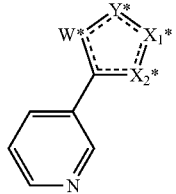

(II)

or a pharmaceutically acceptable salt, a solvate or hydrate thereof,
wherein
the heterocycle comprises two double bonds which may be present at varying positions, represented by the dashed lines —(—);
the heterocycle comprises two heteroatoms,
W* is N, NH or N-2-(trimethylsilyl)ethoxymethyl;
Y* is CH, O, N or NR4, wherein R4 is chosen from H, 2-(trimethylsilyl)-ethoxymethyl, —SO$_2$N(CH$_3$)$_2$ and —SO$_2$-phenyl; wherein
if Y* is O, X$_1$* is CH and X$_2$* is tC—Z*13 R2* or C—R3*, wherein Z* is NH, O, or S; and
if Y* is CH or NH, one of X$_1$* and X$_2$* is CH or N, wherein if X$_1$* is CH or N, X$_2$* is C—Z—R2 or C—R3, and if X$_2$* is CH or N, X$_1$* is C—Z—R2 or C—R3, wherein Z* is NH or S;
R2* is chosen from (C$_1$-C$_8$)alkyl, (C$_2$-C$_8$)alkenyl and (C$_2$-C$_8$)alkynyl, optionally independently substituted with one or more substituents chosen from halogen, hydroxy, cyano, oxo, (C$_1$-C$_6$)alkoxy, (C$_1$-C$_6$)alkylthio, (C$_1$-C$_6$)alkenyloxy, (C$_1$-C$_6$)alkenylthio, (C$_1$-C$_4$)alkoxy(C$_1$-C$_4$)alkoxy, (C$_5$-C$_7$)cycloalkyl, a 5-membered unsaturated heterocycle (optionally substituted with halogen), phenyl, phenyloxy, and phenylthio, wherein the phenyl group is optionally substituted with halogen; and
R3* is chosen from (C$_4$-C$_{10}$)alkyl, (C$_2$-C$_{10}$)alkenyl and (C$_2$-C$_{10}$)alkynyl, optionally independently substituted with one or more substituents chosen from halogen, hydroxy, cyano, (C$_1$-C$_6$)alkoxy, (C$_1$-C$_6$)alkylthio, (C$_1$-C$_6$)alkenyloxy, (C$_1$-C$_6$)alkenylthio, (C$_1$-C$_4$)alkoxy(C$_1$-C$_4$)alkoxy, (C$_5$-C$_7$)cycloalkyl, a 5-membered unsaturated heterocycle optionally substituted with halogen, phenyl, phenyloxy and phenylthio, wherein the phenyl group is optionally substituted with halogen;
and optionally, when R2* is an unbranched (C$_2$-C$_8$)alkyl, R2* links to formula (IIa)

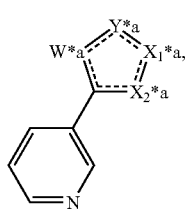

(IIa)

or a pharmaceutically acceptable salt, a solvate or hydrate thereof,
through X$_1$*a or X$_2$*a of formula (IIa), wherein if X$_1$* is CH or N, X1*a is CH or N and X2*a is C-Z*a-, or
if X$_1$* is C—Z*—R2*, X$_1$*a is C-Z*a- and X$_2$*a is CH or N,
wherein X$_1$*a or X$_2$*a having Z*a links to R2*; and
the symbols W*a, Y*a and Z*a have the same meanings as defined previously for the symbols W*, Y* and Z* and are not independently selected, each of the symbols W*a, Y*a and Z*a representing identical symbols, respectively, as the symbols W*, Y* and Z* in the other part of the structure of formula (II).

These heterocyclic compounds are useful in the preparation of compounds of formula (I) wherein R1 has the structure (a). The preferred substitution pattern in the compound of formula (II) corresponds to the preferred substitution pattern of compounds of formula (I).

Also an embodiment of this invention is a heterocyclic compound of the formula (III)

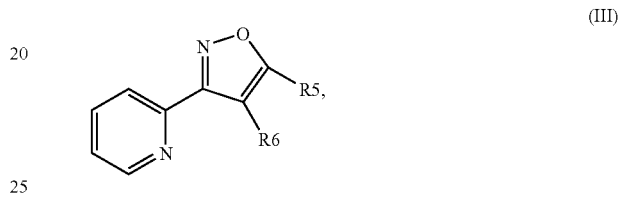

(III)

wherein R5 is H and R6 is Br,
or R5 is —Si(CH$_3$)$_3$ and R6 is Br or —Si(CH$_3$)$_3$,
which compound is useful in the preparation of compounds of formula (I) wherein R1 has the structure (a).

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

Compounds may exist as polymorphs and as such are intended to be included in the present invention. In addition, compounds may form solvates with water (i.e., hydrates) or common organic solvents, and such solvates are also intended to be encompassed within the scope of this invention.

Isotopically-labeled compound of formula (I) or pharmaceutically acceptable salts thereof, including compounds of formula (I) isotopically-labeled to be detectable by PET or SPECT, also fall within the scope of the invention. The same applies to compounds of formula (I) labeled with [$^{13}$C]—,

[$^{14}$C]—, [$^3$H]—, [$^{18}$F]—, [$^{125}$I]—or other isotopically enriched atoms, suitable for receptor binding or metabolism studies.

The term "pharmaceutically acceptable salt" refers to those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. They can be prepared in situ when finally isolating and purifying the compounds of the invention, or separately by reacting them with pharmaceutically acceptable non-toxic bases or acids, including inorganic or organic bases and inorganic or organic acids.

The compounds of the invention may be administered enterally or parenterally. The exact dose and regimen of these compounds and compositions thereof will be dependent on the biological activity of the compound per se, the age, weight and sex of the patient, the needs of the individual subject to whom the medicament is administered, the degree of affliction or need and the judgment of the medical practitioner. In general, parenteral administration requires lower dosages than other methods of administration which are more dependent upon adsorption. However, the dosages for humans are preferably 0.001-10 mg per kg body weight, more preferably 0.01-1 mg per kg body weight. In general, enteral and parenteral dosages will be in the range of 0.1 to 1,000 mg per day of total active ingredients.

The medicament manufactured with the compounds of this invention may also be used as adjuvant in therapy. In such a case, the medicament or is administered in a combination treatment with other compounds useful in treating such disease states. Also pharmaceutical combination preparations comprising at least one compound of the present invention and at least one other pharmacologically active substance are considered in this respect.

Mixed with pharmaceutically suitable auxiliaries, e.g. as described in the standard reference "Remington, The Science and Practice of Pharmacy" (21$^{st}$ edition, Lippincott Williams & Wilkins, 2005, see especially Part 5: Pharmaceutical Manufacturing) the compounds may be compressed into solid dosage units, such as pills or tablets, or be processed into capsules or suppositories. By means of pharmaceutically suitable liquids the compounds can also be applied in the form of a solution, suspension or emulsion.

For making dosage units, e.g. tablets, the use of conventional additives such as fillers, colorants, polymeric binders and the like, is contemplated. In general, any pharmaceutically suitable additive which does not interfere with the function of the active compounds can be used.

Suitable carriers with which the compounds of the invention can be administered include for instance lactose, starch, cellulose derivatives and the like, or mixtures thereof, used in suitable amounts. Compositions for intravenous administration may for example be solutions of the compounds of the invention in sterile isotonic aqueous buffer. Where necessary, the intravenous compositions may include for instance solubilizing agents, stabilizing agents and/or a local anesthetic to ease the pain at the site of the injection.

Pharmaceutical compositions of the invention may be formulated for any route of administration and comprise at least one compound of the present invention and pharmaceutically acceptable salts thereof, with any pharmaceutically suitable ingredient, excipient, carrier, adjuvant or vehicle.

By "pharmaceutically suitable" it is meant that the carrier, diluent or excipient must be compatible with the other ingredients of the formulation and not deleterious to the recipient thereof.

In an embodiment of the invention, a pharmaceutical pack or kit is provided comprising one or more containers filled with one or more pharmaceutical compositions of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described in this document. All publications, patent applications, patents, and other references mentioned herein are incorporated by reference in their entirety. In case of conflict, the present specification, including definitions, will control.

The following examples are only intended to further illustrate the invention in more detail, and therefore these examples are not deemed to restrict or limit the scope of the invention in any way.

EXAMPLES

§1. Materials and Methods

Nuclear magnetic resonance spectra ($^1$H NMR and $^{13}$C NMR, APT) were determined in the indicated solvent using a Bruker ARX 400 (1H: 400 MHz, $^{13}$C: 100 MHz) at 300 K, unless indicated otherwise. $^{19}$F NMR and $^{13}$C NMR experiments were carried out on a Varian Inova 500 spectrometer operating at 11.74 T (499.9 MHz for $^1$H, 125.7 MHz for $^{13}$C; 50.7 Mhz, 470.4 MHz for $^{19}$F) using a 5 mm SW probe. The spectra were determined in deuterated chloroform or dichloromethane obtained from Cambridge Isotope Laboratories Ltd. Chemical shifts (δ) are given in ppm downfield from tetramethylsilane (1H, 13C) or CCl3F ($^{19}$F). Coupling constants J are given in Hz. Peakshapes in the NMR spectra are indicated with the symbols 'q' (quartet), 'dq' (double quartet), 't' (triplet), 'dt' (double triplet), 'd' (doublet), 'dd' (double doublet), 's' (singlet), 'bs' (broad singlet) and 'm' (multiplet). NH and OH signals were identified after mixing the sample with a drop of D$_2$O.

Flash chromatography refers to purification using the indicated eluent and silica gel (either Acros: 0.030-0.075 mm or Merck silica gel 60: 0.040-0.063 mm).

Column chromatography was performed using silica gel 60 (0.063-0.200 mm, Merck).

Melting points were recorded on a Büchi B-545 melting point apparatus.

Mass spectra (MS) were recorded on a Micromass QTOF-2 instrument with MassLynx application software for acquisition and reconstruction of the data. Exact mass measurement was done of the quasimolecular ion [M+H]$^+$. Accurate mass measurements were performed using a JEOL JMS-SX/SX 102 A Tandem Mass Spectrometer using Fast Atom Bombardement (FAB). A resolving power of 10,000 (10% valley definition) for high resolution FAB mass spectrometry was used.

All reactions involving moisture sensitive compounds or conditions were carried out under an anhydrous nitrogen atmosphere.

Reactions were monitored by using thin-layer chromatography (TLC) on silica coated plastic sheets (Merck precoated silica gel 60 F254) with the indicated eluent. Spots were visualised by UV light (254 nm) or 12.

Extinction coefficients were determined with a HP 8453 UV-Vis spectrophotometer.

Analytical high performance liquid chromatography (HPLC) was performed on a C18 column (Inertsil ODS-3, particle size 3 mm; 4.6 mm 50 mm) using the following elution gradient: linear gradient of 5% to 95% aqueous $CH_3CN$ containing 0.04% $HCO_2H$ over 5 min, then 95% aqueous $CH_3CN$ containing 0.04% $HCO_2H$ for 2 min at 2.0 ml min$^{-1}$. Products were detected at $\lambda=254$ nm.

Liquid Chromatography-Mass Spectrometry (LC-MS), Method A

The LC-MS system consists of 2 Perkin elmer series 200 micro pumps. The pumps are connected to each other by a 50 µl tee mixer, connected to a Gilson 215 auto sampler. The method is as follows:

| step | total time | flow (ul/min) | A (%) | B (%) |
|---|---|---|---|---|
| 0 | 0 | 2000 | 95 | 5 |
| 1 | 1.8 | 2000 | 0 | 100 |
| 2 | 2.5 | 2000 | 0 | 100 |
| 3 | 2.7 | 2000 | 95 | 5 |
| 4 | 3.0 | 2000 | 95 | 5 |

A = 100% Water with 0.025% HCOOH and 10 mmol NH4HCOO pH = +/−3
B = 100% ACN with 0.025% HCOOH The auto sampler has a 2 µl injection loop. The auto sampler is connected to a Waters Atlantis C18 30*4.6 mm column with 3 µm particles. The column is thermo stated in a Perkin Elmer series 200 column oven at 40° C. The column is connected to a Perkin Elmer series 200 UV meter with a 2.7 µl flowcel. The wavelength is set to 254 nm. The UV meter is connected to a Sciex API 150EX mass spectrometer.

The mass spectrometer has the following parameters: Scanrange: 150-900 a.m.u.; polarity: positive; scan mode: profile; resolution Q1: UNIT; step size: 0.10 a.m.u.; time per scan: 0.500 sec; NEB: 10; CUR: 10 IS: 5200; TEM: 325; DF: 30; FP: 225 and EP: 10.

The light scattering detector is connected to the Sciex API 150. The light scattering detector is a Sedere Sedex 55 operating at 50° C. and 3 bar $N_2$.

The complete system is controlled by a G3 powermac.

Liquid Chromatography-Mass Spectrometry (LC-MS), Method B

The LC-MS system consists of an Agilent series 1100 system consisting of the following components:
G1379A Degasser
G1312A Binary Pump The pumps are connected to a G1313A ALS auto sampler. The method is as follows:

| Step | total Time (min) | flow (ml/min) | A (%) | B (%) |
|---|---|---|---|---|
| 0 | 0 | 1.0 | 2 | 98 |
| 1 | 10.5 | 1.0 | 98 | 2 |
| 2 | 18.0 | 1.0 | 98 | 2 |
| 3 | 18.1 | 1.0 | 2 | 98 |
| 4 | 24.0 | 1.0 | 2 | 98 |

A: Acetonitrile with 0.1% HCOOH or Acetonitrile with 10 mM NH3
B: Water with 0.1% HCOOH or Water with 10 mM NH3

The auto sampler is connected to a Zorbax Extend C18 column 150×4.6 mm with 3.5 um particles.

The column is thermo stated in a G1316A Colcomm column oven at 35° C.

The column is connected to a G1315B DAD diode array detector. The wavelength range is set from 220 to 320 nm. The UV meter is connected to G1946D MSD mass spectrometer, operating in electron spray mode.

The mass spectrometer has the following parameters:

| | |
|---|---|
| Scan range: | 100-800 amu |
| Polarity: | Positive & Negative |
| Mode: | Scan |
| Step size: | 0.20 |
| Cycle time: | 1.04 sec |
| % Cycle time: | 50% |
| Drying gas: | Nitrogen |
| Gas flow: | 10 l/min |
| Gas temp.: | 300° C. |
| Neb. Press.: | 30 psi |
| Capillary Volt.: | 3000 V |

An Alltech ELSD 2000 detector is connected parallel with the MSD. The flow is split after the DAD.

The ELSD has the following parameters:

| | |
|---|---|
| Drying gas: | Nitrogen |
| Gas flow: | 1.5 l/min |
| Drift tube temp.: | 39° C. |
| Impactor: | On |

§2. Abbreviations n-BuLi n-butyl lithium
t-BuOH t-butanol
dba dibenzylideneacetone
DCM dichloromethane
DMF N,N'-dimethylformamide
DMF-DMA N,N'-dimethylformamide dimethyl acetal
DMSO dimethylsulfoxide
EtOH ethanol
Et2O diethyl ether
g gram(s)
h hour(s)
Me methyl
MeI methyl iodide
MeOH methanol
mg milligram(s)
min minute(s)
ml milliliter(s)
m.p. melting point c.q. melting range
NBS N-bromosuccinimide
NIS N-iodosuccinimide
PE petroleum ether (40-65° C.)
Rt retention time (LC/MS)
SEM-Cl (2-Chloromethoxy-ethyl)-trimethylsilane
TBAF tetrabutylammonium fluoride
THF tetrahydrofuran

§3. General Aspects of Syntheses

Different synthetic routes for the preparations of compounds of the present invention illustrated in formula I are described and easily prepared from readily available starting materials. More general information on pyrazole, imidazole and isoxazole chemistry, see for example: J. A. Joule, K. Mills and G. F. Smith, "Heterocyclic Chemistry", third edition, Stanley Thornes (Publishers) Ltd., Cheltenham, 1998. More information on addition and subsequent removal of protective groups in organic synthesis can be found in: T. W. Greene and P. G. M. Wuts, "Protective Groups in Organic Synthesis", third edition, John Wiley & Sons, Inc., New York, 1999.

The selection of the particular method depends on factors such as the compatibility of functional groups with the reagent used, the possibility to use protecting groups, catalysts, activating and coupling reagents and the ultimate structural features present in the final compound being prepared.

In an example of the general procedure (scheme 1), nicotinoyl chloride hydrochloride (1) is converted to the N-methyl-N-methoxyamide (2) in the presence of a base and reacted with hexyl-lithium (J. Med. Chem., 35, 1992, 2392-2406) to produce 1-pyridin-3-yl-heptan-1-one (3).

Mild α-methylenation of compound 3 (J. Org. Chem., 71, 2006, 2538-2541) afforded 2-methylene-1-pyridin-3-yl-heptan-1-one (4), which was reacted with hydrazine (Synthesis, 1989, 320-321) to produce 1-(4-pentyl-3-pyridin-3-yl-4,5-dihydropyrazol-1-yl)-ethanone (5). Oxidation of a 2-pyrazoline to a pyrazol can be accomplished using methods well known to those skilled in the art. Specific conditions are: activated $MnO_2$ in dichloroethane (EP0094555) to produce compound 6, which was deprotected under basic conditions to afford compound 7. The 3-(4-pentyl-1H-pyrazol-3-yl)-1,2,5,6-tetrahydro-1-methylpyridine derivate (9) was obtained from compound 8 by quarternizing the pyridine moiety with $CH_3I$ and reducing the corresponding pyridinium salt with $NaBH_4$ (Arch. Pharm. Pharm. Med. Chem., 336, 2003, 143-154).

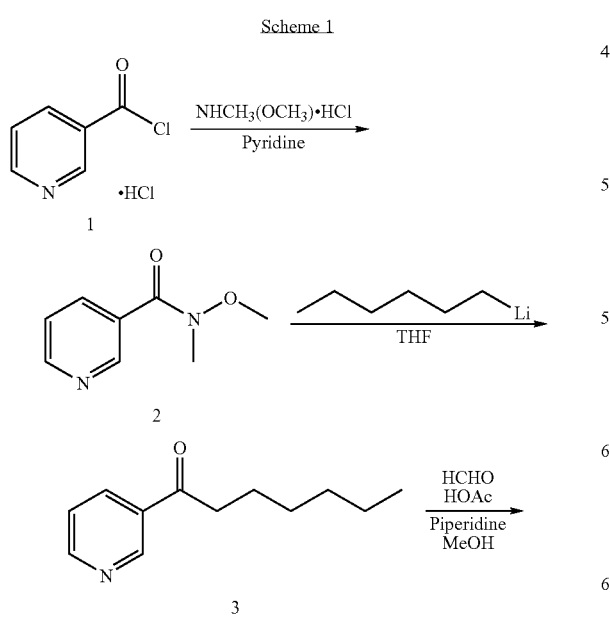
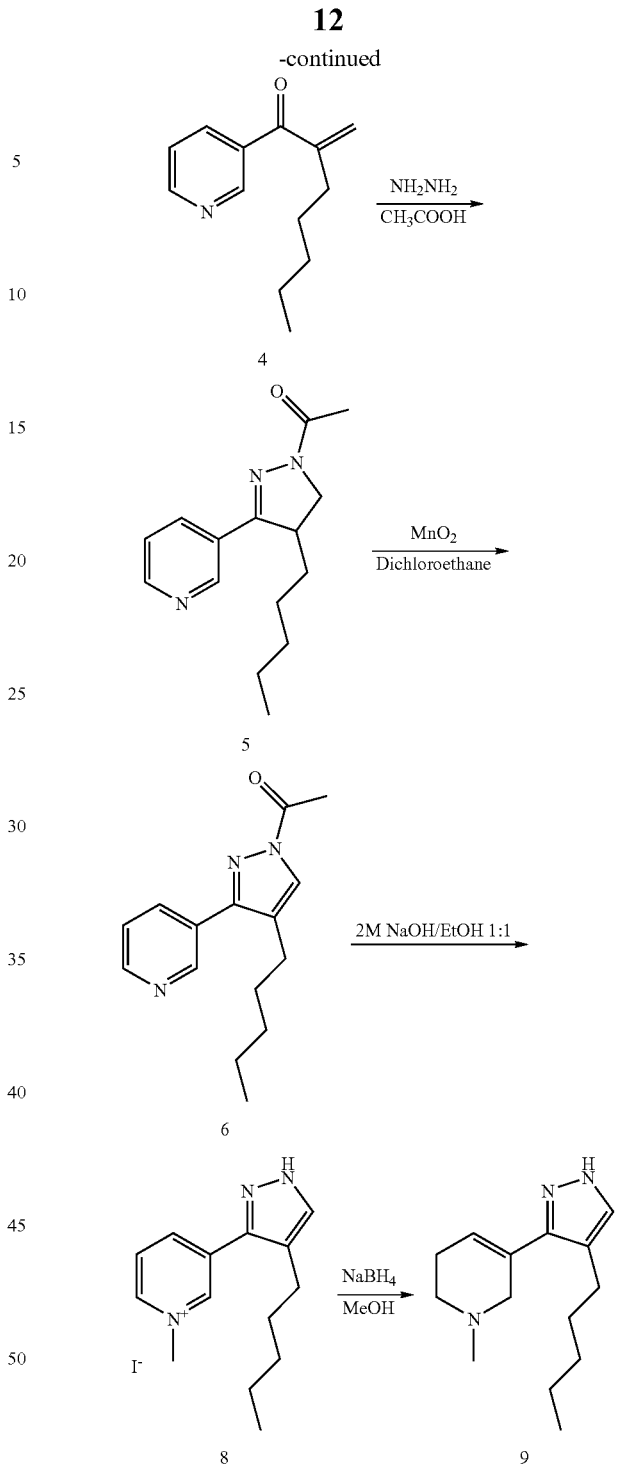

In another example of the general procedure (scheme 2), readily available pyridin-3-yl-acetic acid (10) is converted to the N-methyl-N-methoxyamide derivate (12), which is reacted with BuLi to produce 1-pyridin-3-yl-hexan-2-one (13). N,N-dimethylformamide dimethylacetal treatment of 13 furnished the enamine (14) which is converted to the pyrazol (15). The synthesis of 3-(4-Butyl-1H-pyrazol-3-yl)-1,2,5,6-tetrahydro-1-methylpyridine (16) is illustrated in scheme 2 according to the two step sequence shown in scheme 1.

Scheme 2

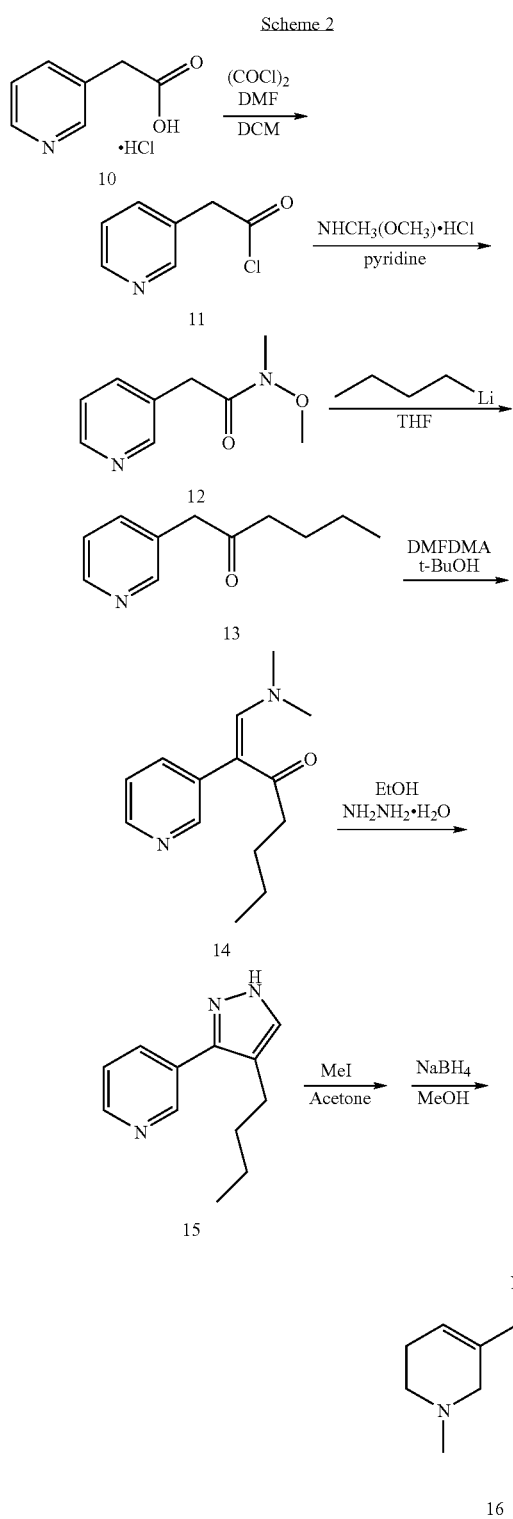

hr), was trapped with a disulfide (for example methyldisulfanylmethane) affording 3-(4-methylsulfanyl-1H-pyrazol-3-yl)-pyridine 21A, which was converted to the 1,2,5,6-tetrahydro-1-methylpyridine derivate 22A according to the two step sequence shown in scheme 1.

The generation of anions at the ortho position of the aromatic systems employed in the synthetic procedures described in this application is performed according to a general synthetic strategy known as Directed Ortho Metalation (DOM). Within this area, a number of functional groups known as Directed Metalation Groups (DMG's) have been studied for this purpose.

The dimethylsulfonamide group as Directing Metalation Group (DMG) in the $N_1$-position of 3-pyridin-3-yl-pyrazole-1-sulfonic acid dimethylamide (23) enables the lithiation of the 5-position and thereby its functionalisation (Chem. Ber., 124, 1991, 1639-1650). The 5-lithioderivate of 23, prepared on multigram scale by α-metallation (1.0 equiv, t-Buli, THF, −78° C., 1 hr), was trapped (J. Org. Chem., 64, 1999, 5366-5370) with a disulfide (for example 1-butyldisulfanylbutane) to afford 5-butylsulfanyl-3-pyridin-3-yl-pyrazol-1-sulfonic acid dimethylamide 24, which was deprotected (25) and converted to the 1,2,5,6-tetrahydro-1-methylpyridine derivate 26 according to the two step sequence shown in scheme 1.

Scheme 3

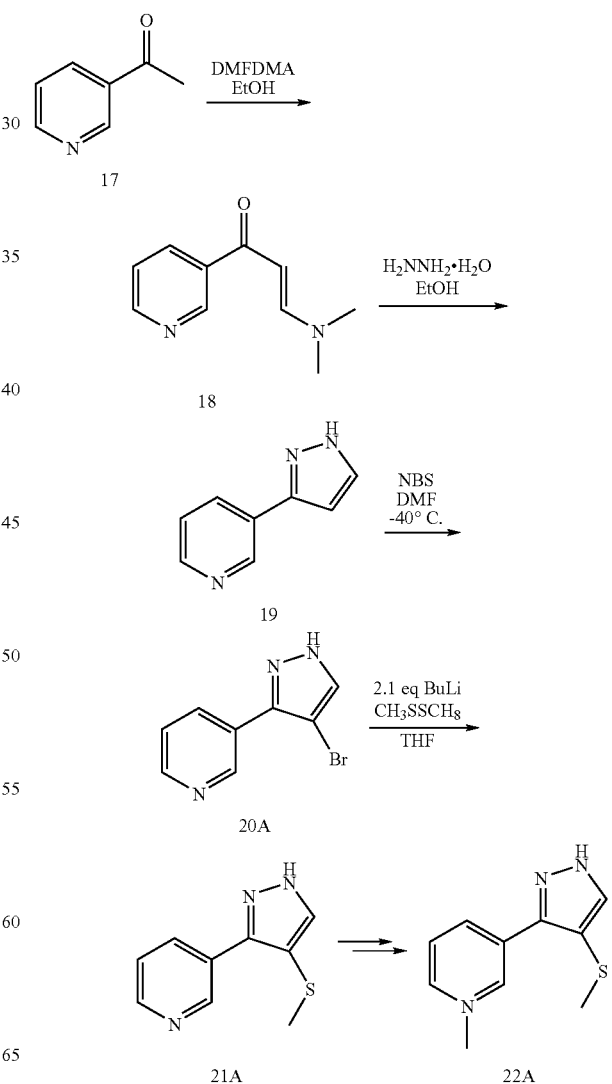

In yet another example of the general procedure (scheme 3), 3-(4-bromo-1H-pyrazol-3-yl)-pyridine (20A) or its iodo analog (20B) (Bioorganic & Medicinal Chemistry, 4, 1996, 227-237) is used as precursor for the synthesis of compounds of the general formula I. The di-lithio derivate (Bioorganic & Medicinal Chemistry, 8, 2000, 2317-2335) of 20A, prepared on multigram scale by pyrazol-NH deprotonation and bromine-lithium exchange (2.1 equiv. n-Buli, THF, −78° C., 2

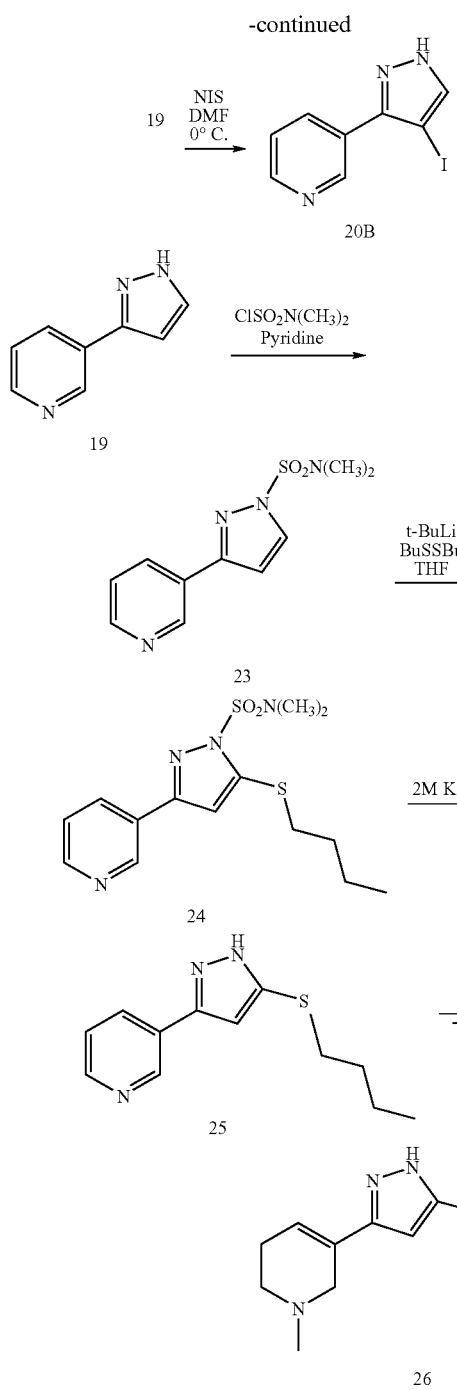

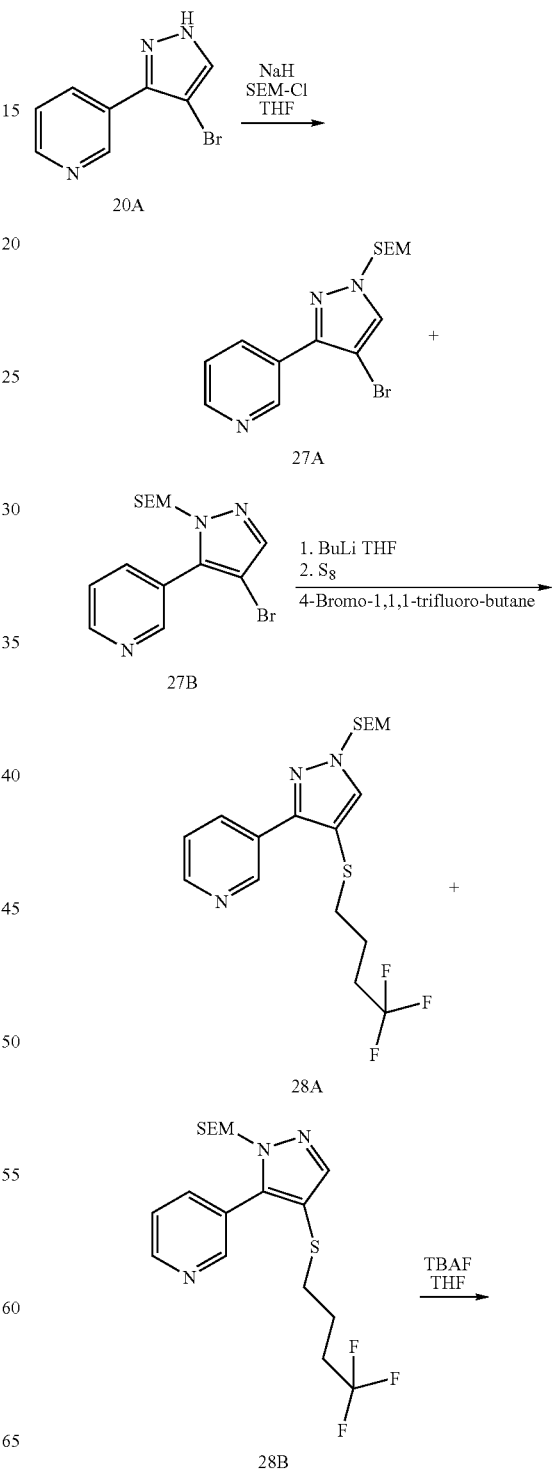

with 4-bromo-1,1,1-trifluoro-butane to afford a mixture of 28A and 28B. Subsequent removal of the SEM protecting group resulted in the desired 3-[4-(4,4,4-trifluoro-butylsulfanyl)-1H-pyrazol-3-yl]-pyridine 21B, which was converted to the 1,2,5,6-tetrahydro-1-methylpyridine derivate 22B according to the two step sequence shown in scheme 1.

Another synthetic route for the preparations of compounds of the present invention illustrated in formula I is described in scheme 4. The introduction of the 2-(trimethylsilyl)-ethoxymethyl group (SEM) as a protective group (Tetrahedron Letters, 39, 1998, 5171-5174) afforded a mixture of compounds 27A and 27B. Subsequent bromine-lithium exchange (1.1 equiv. n-BuLi, THF, −78° C., 1 hr) and reacting this 4-lithioderivate of 27A/B with S₈ generates the intermediate lithium aryl thiolate (J. Org. Chem., 69, 2004, 3236-3239) of 3-pyridin-3-yl-1-(2-trimethylsilanyl-ethoxymethyl)-1H-pyrazol-4-thiol. This intermediate was trapped

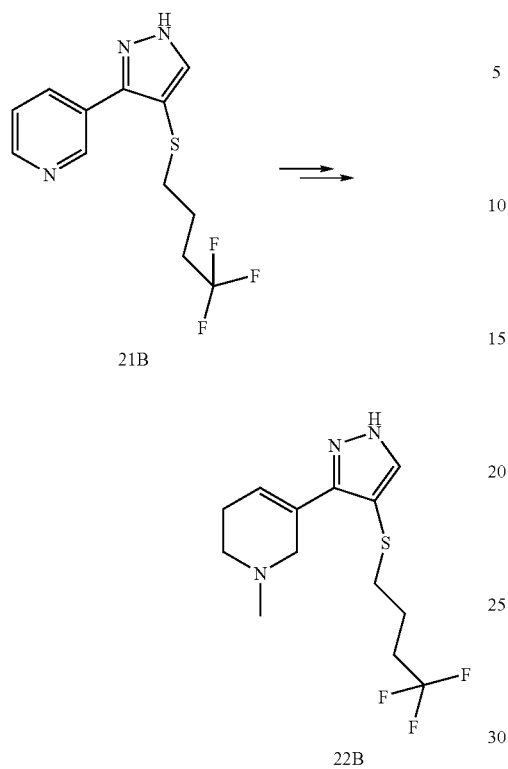

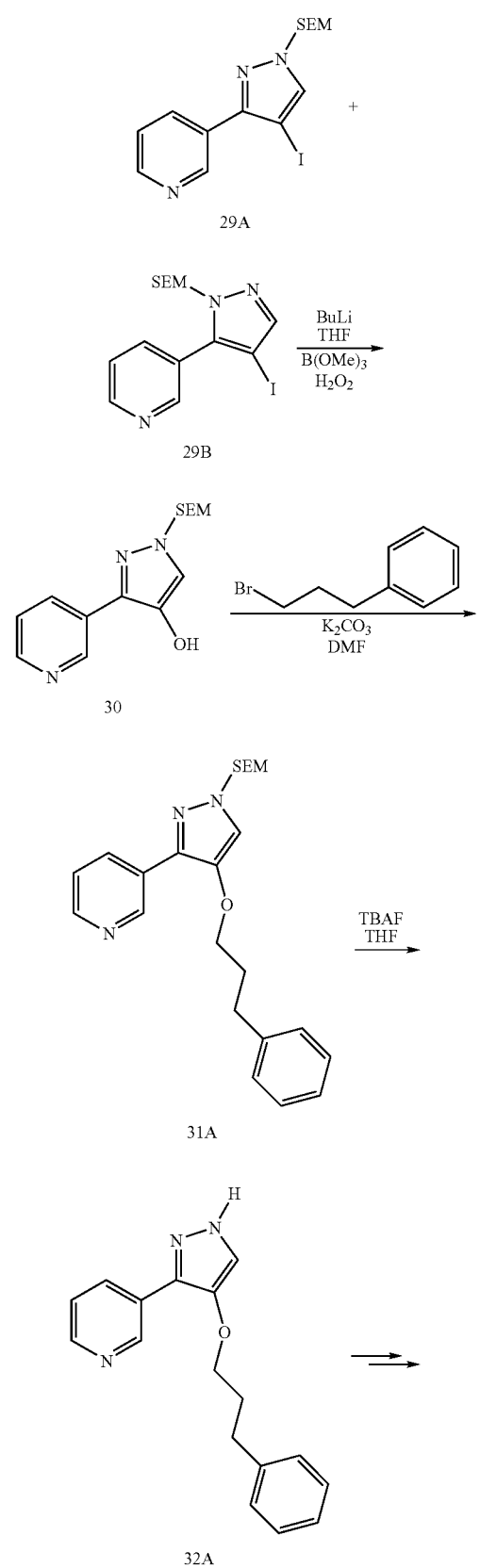

In another aspect, 3-(4-iodo-1H-pyrazol-3-yl)-pyridine (20B, scheme 5) is employed as starting material for compounds of the present invention illustrated in formula I.

The 4-lithioderivate of the SEM protected derivative 29A/B, prepared according to the corresponding compounds 27A/B (scheme 4), was reacted with trimethyl borate followed by in situ hydrogen peroxide oxidation (J. Heterocyclic Chem., 31, 1994, 1377-1380) to afford the corresponding 3-pyridin-3-yl-1-(2-trimethylsilanyl-1-ethoxymethyl)-1H-pyrazol-4-ol (30, one isomer given). Alkylation of the 4-hydroxy derivate 30 can be accomplished using methods well known in the art, for example, by reacting compound 30 with $K_2CO_3$ in DMF in the presence of a variety of (aryl)alkyl halides, for example (3-bromo-propyl)-benzene, to generate compound 31A (one isomer given). Subsequent removal of the SEM group resulted in 3-[4-(3-phenyl-propoxy)-1H-pyrazol-3-yl]-pyridine (32A), which was converted to the 1,2,5,6-tetrahydro-1-methylpyridine derivate 33A according to the two step sequence shown in scheme 1.

Scheme 5

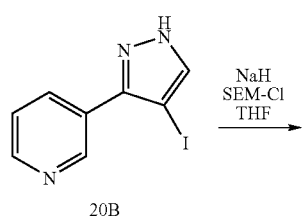

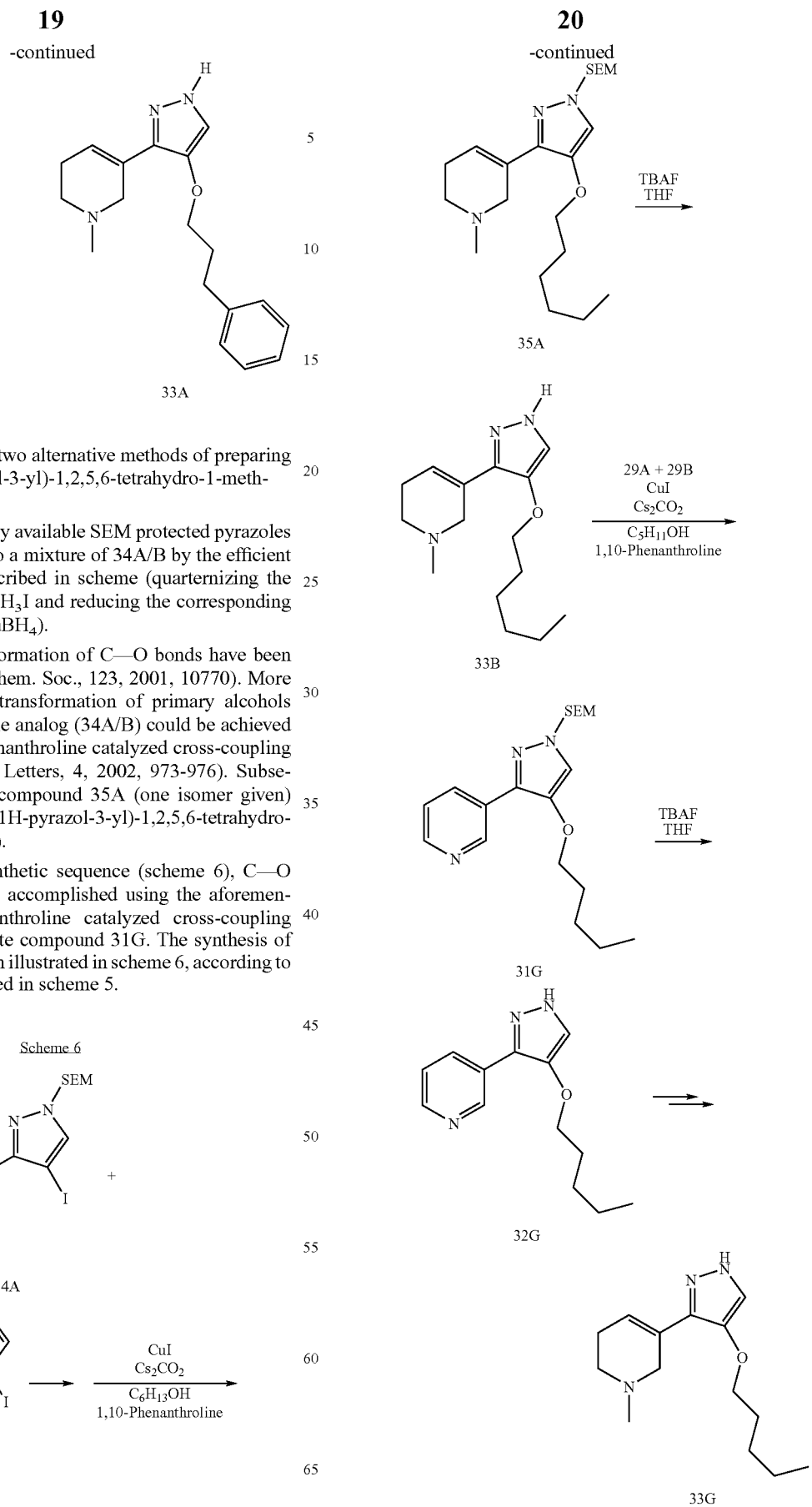

Scheme 6 illustrates two alternative methods of preparing 3-(4-alkoxy-1H-pyrazol-3-yl)-1,2,5,6-tetrahydro-1-methylpyridine compounds.

The mixture of readily available SEM protected pyrazoles 29A/B was converted to a mixture of 34A/B by the efficient two step sequence described in scheme (quarternizing the pyridine moiety with CH$_3$I and reducing the corresponding pyridinium salt with NaBH$_4$).

Techniques for the formation of C—O bonds have been reported (e.g. J. Am. Chem. Soc., 123, 2001, 10770). More precisely, an efficient transformation of primary alcohols with the 4-iodo-pyrazole analog (34A/B) could be achieved using the CuI/1,10-phenanthroline catalyzed cross-coupling methodology (Organic Letters, 4, 2002, 973-976). Subsequent deprotection of compound 35A (one isomer given) yielded 3-(4-hexyloxy-1H-pyrazol-3-yl)-1,2,5,6-tetrahydro-1-methylpyridine (33B).

In an alternative synthetic sequence (scheme 6), C—O bond formation can be accomplished using the aforementioned CuI/1,10-phenanthroline catalyzed cross-coupling methodology to generate compound 31G. The synthesis of compound 33G has been illustrated in scheme 6, according to the procedures illustrated in scheme 5.

One aspect of the invention relates to bis 3-(4-alkylsulfanyl-1H-pyrazol-3-yl)-1,2,5,6-tetrahydro-1-methylpyridine derivatives (for example compound 22C, scheme 7) that bind to and can activate muscarinic receptors (J. Med. Chem., 44, 2001, 4563-4576).

Introduction of the phenylsulfonyl as protective group (starting from 20A) was accomplished regio-selectively to generate 3-(1-phenylsulfonyl-4-bromo-1H-pyrazol-3-yl)-pyridine (36A from 20A).

The cross-coupling of aliphatic and aromatic thiols and aryl bromides can be mediated by a $Pd_2(dba)_3$/Xantphos catalytic system in refluxing xylene to afford the corresponding aryl thioethers (Organic Letters, 6, 2004, 4587-4590, Tetrahedron, 61, 2005, 5253-5259).

Using this methodology, 36A was converted to the protected bis-alkylsulfanyl-pyrazol derivative 37. Removal of the Ni-phenylsulfonyl group can be accomplished using methods well known to those skilled in the art, for example, optionally reacting compound 37 with potassium hydroxide in diethylene glycol in the presence of hydrazine. Quarternizing the (bis)-pyridine moiety with $CH_3I$ and reducing the corresponding (bis)-pyridinium salt with $NaBH_4$ afforded pyrazol derivative 22C.

Scheme 7 illustrates an alternative method for preparing 3-(4-alkylsulfanyl-1H-pyrazol-3-yl)-1,2,5,6-tetrahydro-1-methylpyridine derivatives, so can be used to synthezise compounds presented in scheme 3 & 4 (22A and 22B respectively), the main feature being the availability of the parent thiol.

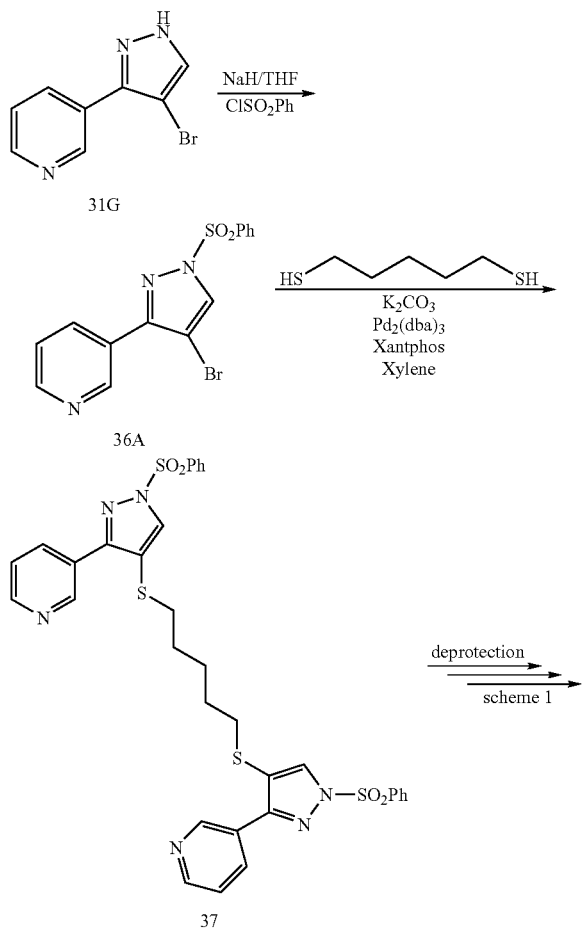

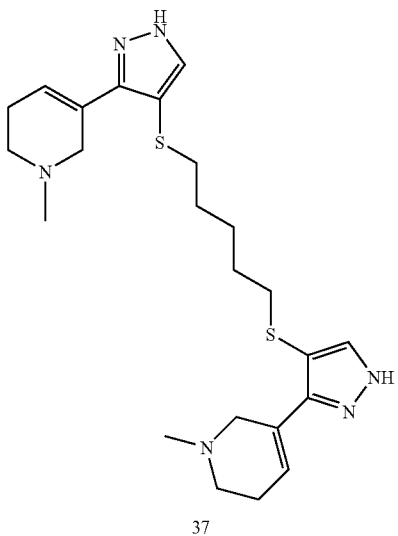

Another illustration of the preparation of compounds of the present invention of formula I is shown in scheme 8.

Straightforward nitration (Chem. Ber., 88, 1955, 1577) of pyrazole derivative 19, afforded 3-(4-nitro-1H-pyrazol-3-yl)-pyridine (38), which was reduced to the corresponding 3-pyridin-3-yl-1H-pyrazol-4-ylamine (39) and reacted with an acid chloride, for example butyryl chloride, to generate the amide (40). Subsequent conversion to the 1,2,5,6-tetrahydro-1-methylpyridine derivate 41 was done accordingly to the two step sequence shown in scheme 1. Subsequent $LiAlH_4$ reduction of the amide generates butyl-[3-(1-methyl-1,2,5,6-tetrahydro-pyridin-3-yl)-1H-pyrazol-4-yl]-amine (42).

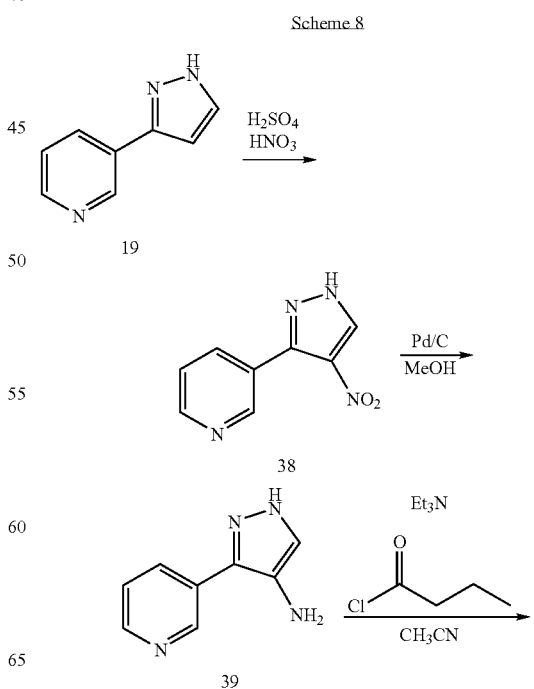

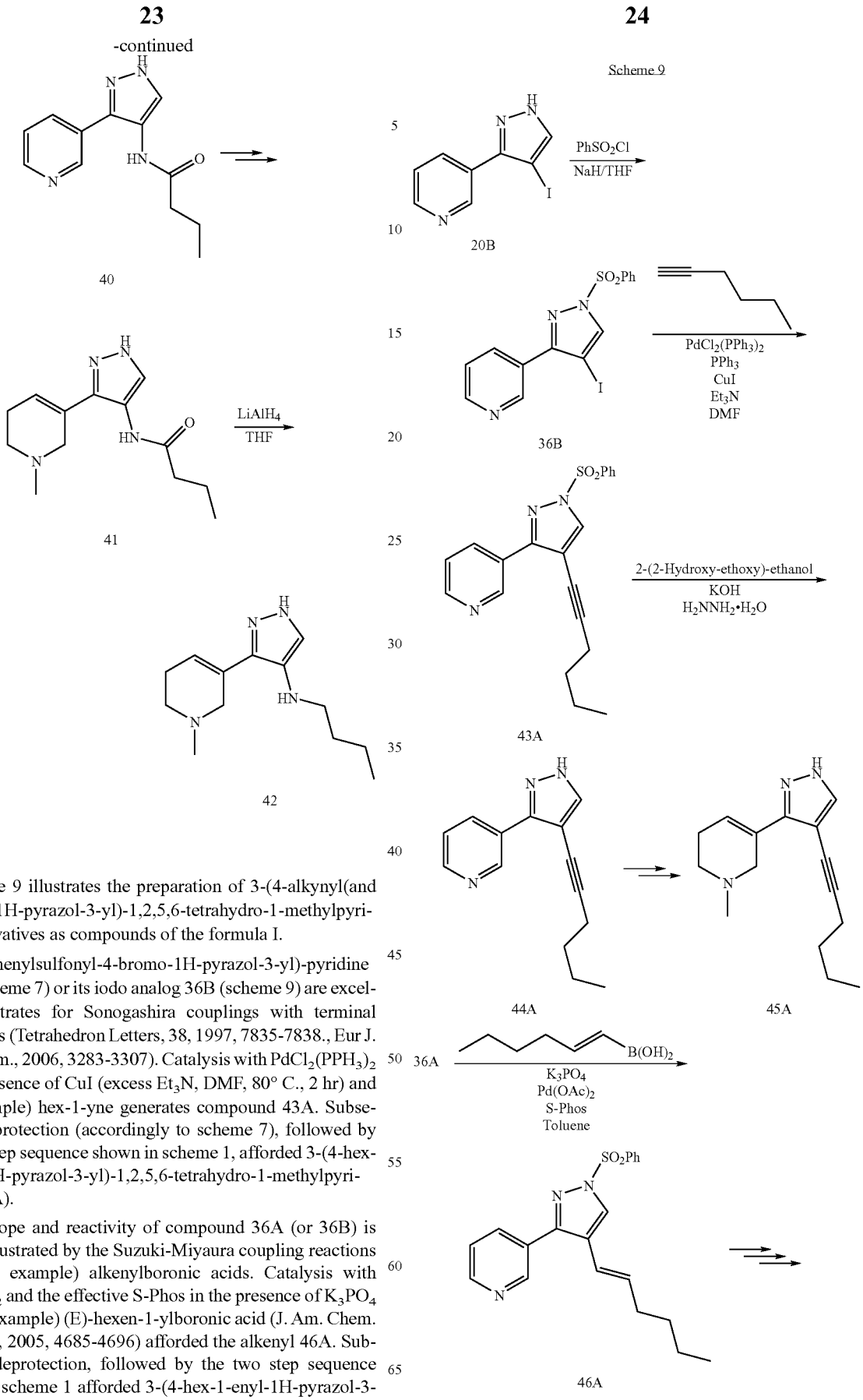

Scheme 9 illustrates the preparation of 3-(4-alkynyl(and alkenyl)-1H-pyrazol-3-yl)-1,2,5,6-tetrahydro-1-methylpyridine derivatives as compounds of the formula I.

3-(1-Phenylsulfonyl-4-bromo-1H-pyrazol-3-yl)-pyridine (36A, scheme 7) or its iodo analog 36B (scheme 9) are excellent substrates for Sonogashira couplings with terminal acetylenes (Tetrahedron Letters, 38, 1997, 7835-7838., Eur J. Org. Chem., 2006, 3283-3307). Catalysis with $PdCl_2(PPH_3)_2$ in the presence of CuI (excess $Et_3N$, DMF, 80° C., 2 hr) and (for example) hex-1-yne generates compound 43A. Subsequent deprotection (accordingly to scheme 7), followed by the two step sequence shown in scheme 1, afforded 3-(4-hex-1-ynyl-1H-pyrazol-3-yl)-1,2,5,6-tetrahydro-1-methylpyridine (45A).

The scope and reactivity of compound 36A (or 36B) is further illustrated by the Suzuki-Miyaura coupling reactions with (for example) alkenylboronic acids. Catalysis with $Pd(OAc)_2$ and the effective S-Phos in the presence of $K_3PO_4$ and (for example) (E)-hexen-1-ylboronic acid (J. Am. Chem. Soc., 127, 2005, 4685-4696) afforded the alkenyl 46A. Subsequent deprotection, followed by the two step sequence shown in scheme 1 afforded 3-(4-hex-1-enyl-1H-pyrazol-3-yl)-1,2,5,6-tetrahydro-1-methylpyridine (47A).

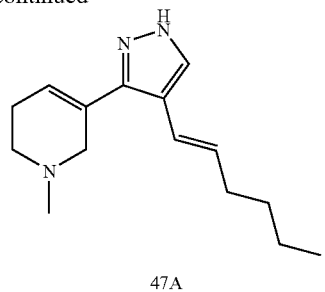

47A

In another aspect, 3-(4-iodo-1H-pyrazol-3-yl)-1-azabicyclo[2.2.2]octane (48, Bioorganic & Medicinal Chemistry 8, 2000, 449-454) is employed as starting material for compounds of the present invention of formula I (scheme 10).

Referring to scheme 3, the di-lithio derivative (Bioorganic & Medicinal Chemistry, 8, 2000, 2317-2335) of 48, (2.1 equiv. n-BuLi, THF, −78° C., 2 hr), was trapped with a disulfide (for example 1-butyldisulfanyl-butane) to afford the corresponding 3-(4-butylsulfanyl-1H-pyrazol-3-yl)-1-azabicyclo[2.2.2]octane 49A.

Scheme 10 illustrates an alternative—but also general—method of preparing 3-(4-alkylsulfanyl-1H-pyrazol-3-yl)-1-azabicyclo[2.2.2]octane derivatives. So, compound 48 could be converted by the Pd$_2$(dba)$_3$/Xantphos catalytic system (analogous to scheme 7, but in DMF at 120° C.) yielding the corresponding aryl thioether 49B, in a single step without protection.

The mixture of readily available SEM protected pyrazoles 50 (one isomer given) was converted to a mixture of 51A by the CuI/1,10-phenanthroline catalyzed cross-coupling methodology as described in scheme 6, however using different conditions. Subsequent deprotection of 51A yields the corresponding 3-(4-butoxy-1H-pyrazol-3-yl)-1-azabicyclo[2.2.2]-octane 52A.

Scheme 10

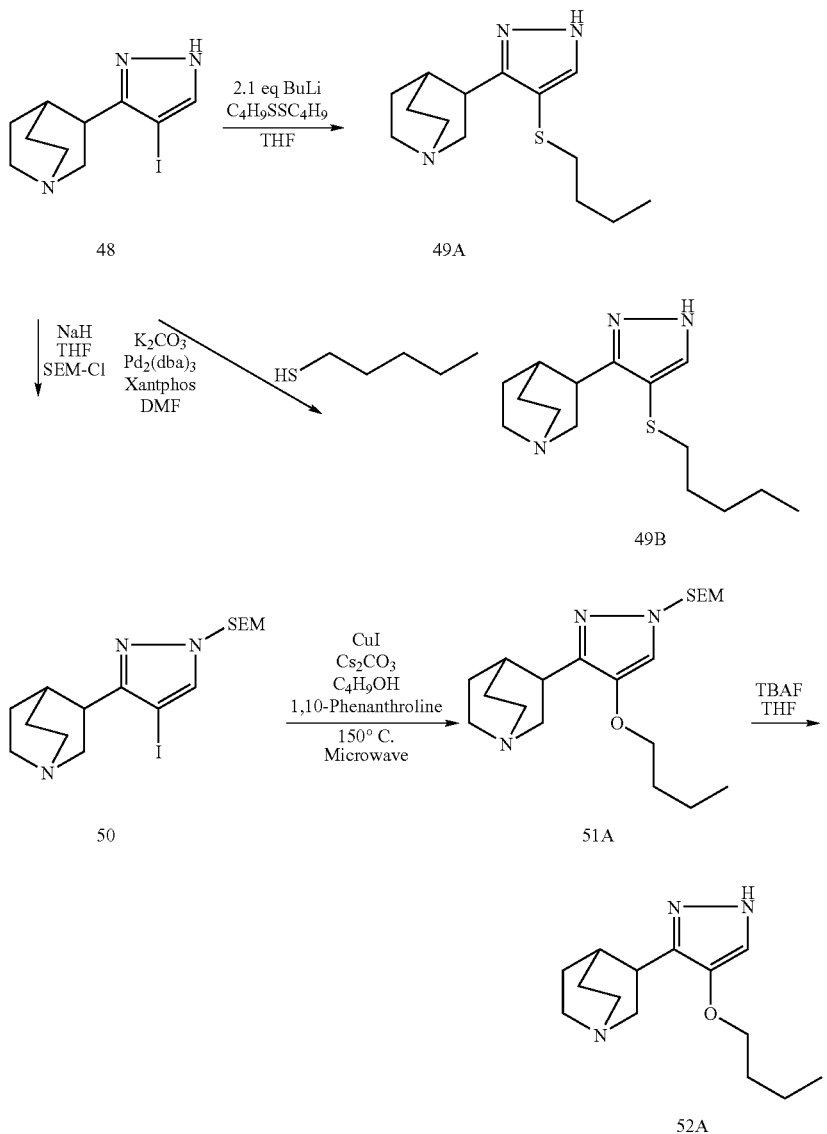

A further illustration of the preparation of compounds of the present invention of formula I is shown in scheme 11.

The readily available 1-aza-bicyclo[3.2.1]octan-6-one (53), (J. Med. Chem., 36, 1993, 683-689) was converted to 6-(1H-pyrazol-3-yl)-1-azabicyclo[3.2.1]-6-ol (55), analogous to an efficient two step sequence (Bioorganic & Medicinal Chemistry 8, 2000, 449-454). Attempts to improve the yield of dehydratation of the alcohol (55) was accomplished by acylation (56) (Heterocycles, 24, 1986, 971-977) and subsequent elimination in the heat (185° C.). Reduction of the enamine (57) gave the anticipated endo 1-azabicyclo[3.2.1] derivative (58). Iodination (Bioorganic & Medicinal Chemistry, 4, 1996, 227-237) and introduction of pentane-1-thiol by the Pd$_2$(dba)/Xantphos catalytic system (accordingly to scheme 7) afforded endo-6-(4-pentylsulfanyl-1-H-pyrazol-3-yl)-1-azabicyclo[3.2.1]octane (60A).

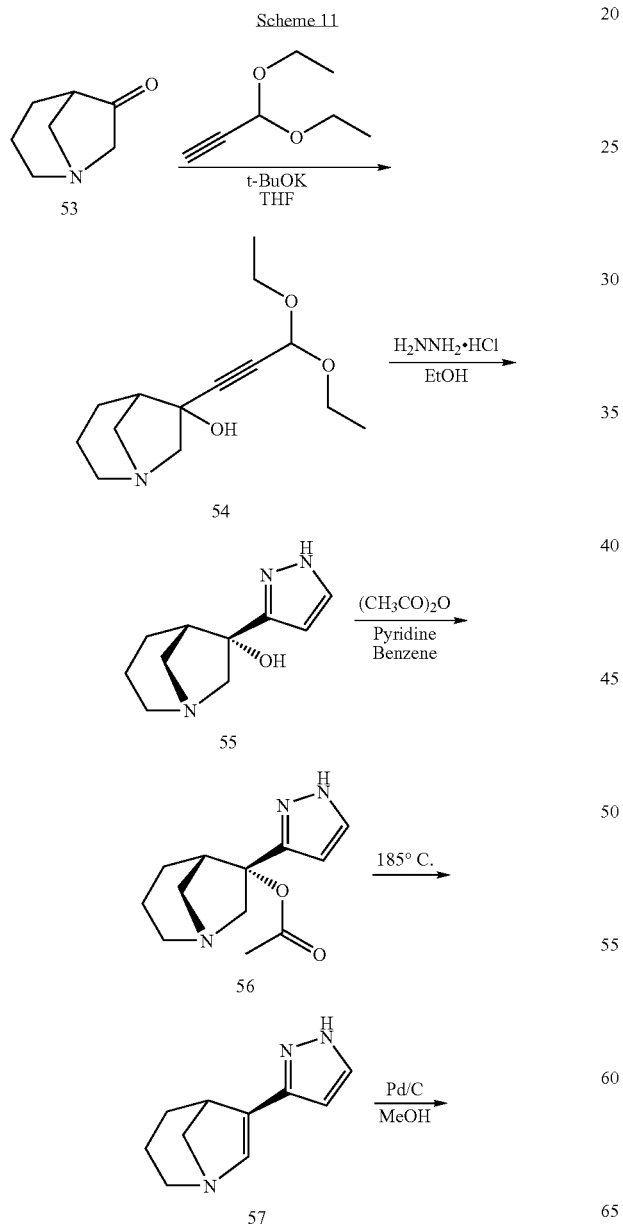

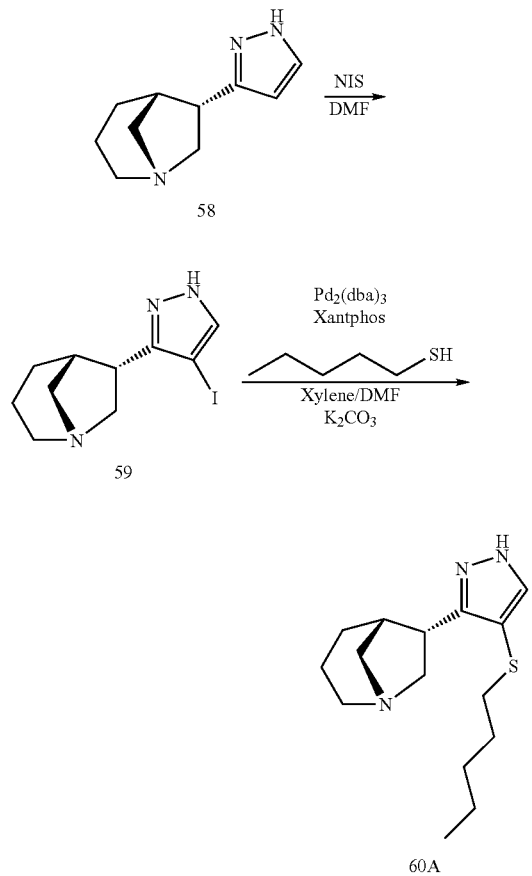

In scheme 12, yet another illustration of the preparation of compounds of the present invention of formula I is shown.

Commercially available 3-pyridinealdoxime (61) is converted to its chlorohydroxyimino derivative (US 2004/0157900) which is converted to nicotinonitrile oxide (Tetrahedron, 61, 2005, 4363-4371) "in situ" and reacted with 1,2-bis-trimethylsilanyl-ethyne (Chem. Ber., 107, 1974, 3717-3722) to afford the 1,3-dipolar cycloaddition product 3-(4,5-bis-trimethylsilanyl-isoxazol-3-yl)-pyridine (62). Halogen-induced ipso desilylation resulted in the 4-bromo-5-trimethylsilanyl derivative (63). Subsequent desilylation with NH$_4$OH (Chem. Ber., 112, 1979, 2829-2836) generates 3-(4-bromo-isoxazol-3-yl)-pyridine (64).

The isoxazole-pyridine derivatives 62, 63 and 64 are new compounds and, as such, embodiments of the present invention.

Introduction of (for example) butane-1-thiol to compound 64 by the Pd$_2$(dba)$_3$/Xantphos catalytic system (accordingly to scheme 7, 10 and 11) afforded 3-(4-butylsulfanyl-isoxazol-3-yl)-pyridine (65A). Quarternizing the pyridine moiety, preferentially with sulfuric acid dimethyl ester and reducing the corresponding pyridinium salt with NaBH$_4$, generates the corresponding 3-(4-butylsulfanyl-isoxazol-3-yl)-1,2,5,6-tetrahydro-1-methylpyridine (66A).

Scheme 12

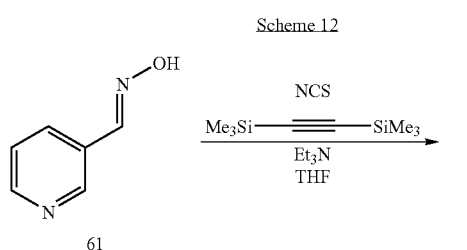
61

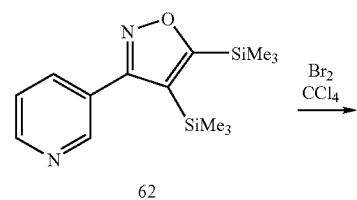
62

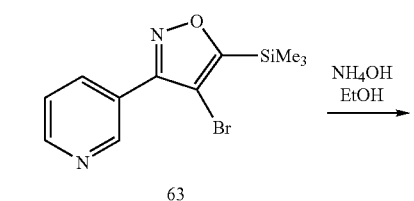
63

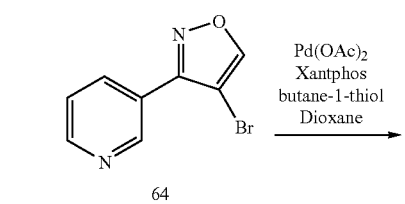
64

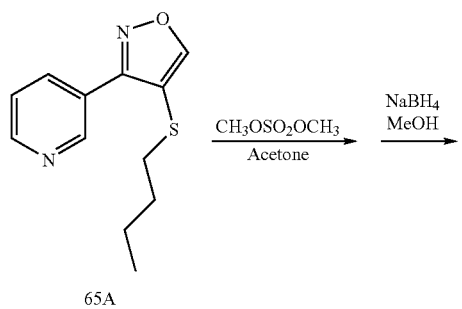
65A 3-(4-Bromo-isoxazol-3-yl)-pyridine (64) is an excellent substrate for Sonogashira couplings with (terminal) acetylenes using an analog of the methodology described in scheme 9.

Subsequent conversion of these alkynyl derivatives (scheme 13, for example 69A) using the quarternizing and reduction conditions described in scheme 12, afforded the corresponding 3-(4-alkynyl-isoxazol-3-yl)-1,2,5,6-tetrahydro-1-methylpyridine derivatives (for example 70A).

The scope and reactivity of compound 64 is further illustrated by the Suzuki-Miyaura coupling reactions with (for example) alkenylboronic acids using the methodology described in scheme 9. Subsequent conversion of these alkenyl derivatives (scheme 13, for example 67A) using the quarternizing and reduction conditions described in scheme 12, afforded the corresponding 3-(4-alkenyl-isoxazol-3-yl)-1,2,5,6-tetrahydro-1-methylpyridine derivatives (for example 68A).

Scheme 13

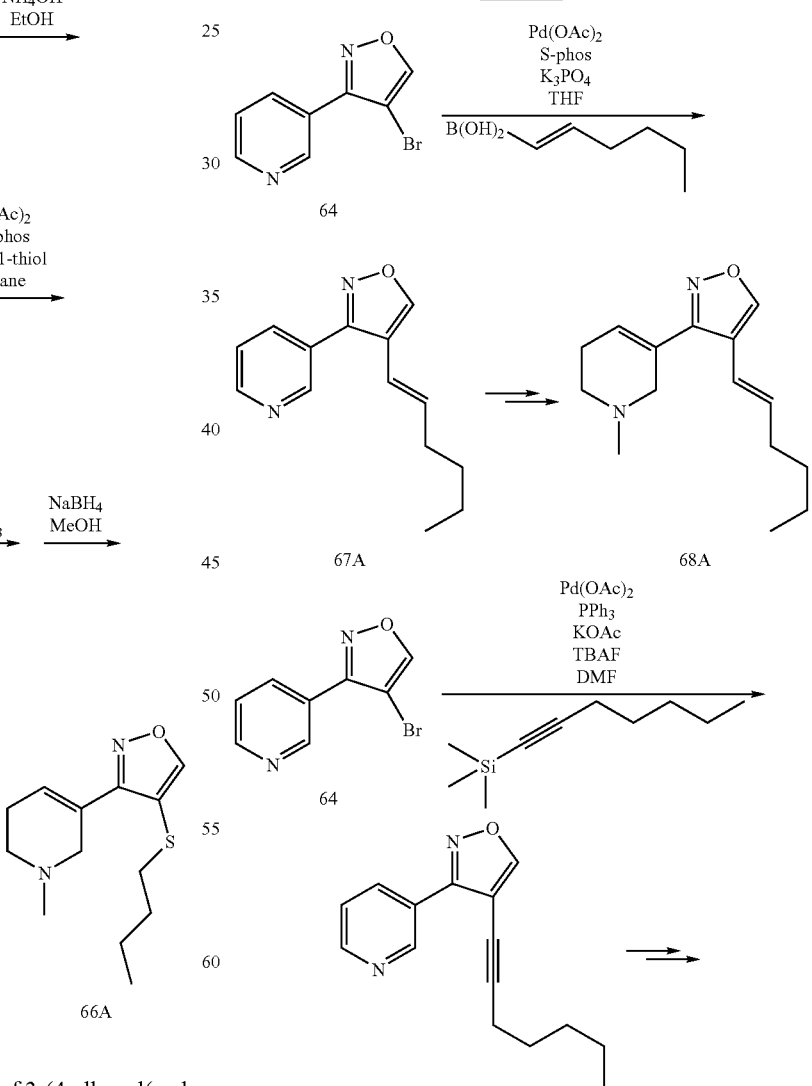

66A

Scheme 13 illustrates the preparation of 3-(4-alkynyl(and alkenyl)-isoxazol-3-yl)-1,2,5,6-tetrahydro-1-methylpyridine derivatives as compounds of the formula I.

-continued

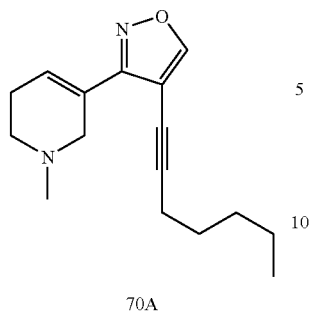
70A

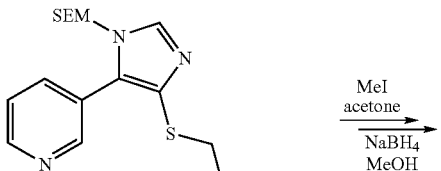
74A

The preparation of compounds of the present invention of formula I is further shown in scheme 14.

3-Trimethylstannanyl-pyridine (71), (Eur. J. Org. Chem., 2002, 2126), obtained from 3-bromo-pyridine using Knochel methodology (Angew. Chem., Int. Ed., 39, 2000, 4414-4435) is coupled under Stille conditions (Toluene, 120° C., PdCl$_2$(PPH$_3$)$_2$ with 4,5-dibromo-1-(2-trimethylsilanyl-ethoxymethyl)-1H-imidazole (72) (Tetrahedron Letters, 39, 1998, 5171-5174) to afford the 3-[5-bromo-3-(2-trimethylsilanyl-ethoxymethyl)-3H-imidazol-4-yl]-pyridine (73). Introduction of (for example) pentane-1-thiol by the Pd$_2$(dba)$_3$/Xantphos catalytic system (accordingly to scheme 12) afforded the corresponding 5-pentylsulfanyl-isoxazole derivative (74A). Quarternizing the pyridine moiety (CH$_3$I) and reducing the corresponding pyridinium salt with NaBH$_4$ (75A) followed by subsequent removal of the SEM group, generates 3-[5-pentylsulfanyl-3H-imidazol-4-yl]-1,2,5,6-tetrahydro-1-methylpyridine (76A).

Alternative to the conversion of 74A to 76A, deprotection of 74B (scheme 14, compound 77) followed by quaternization and reduction generates the desired 3-[5-hexylsulfanyl-3H-imidazol-4-yl]-1,2,5,6-tetrahydro-1-methylpyridine (76B).

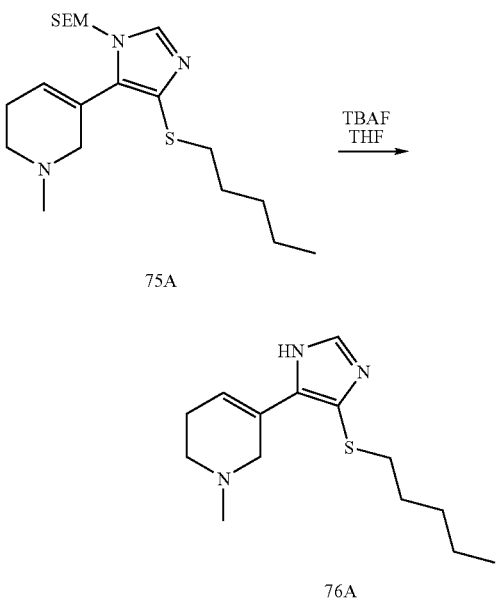
75A

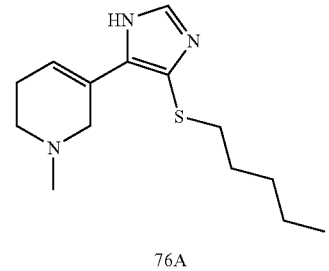
76A

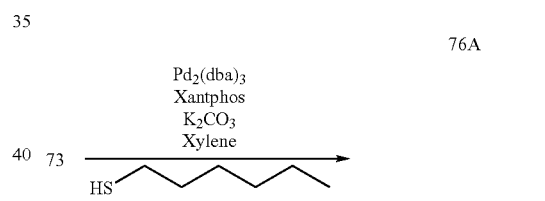

Scheme 14

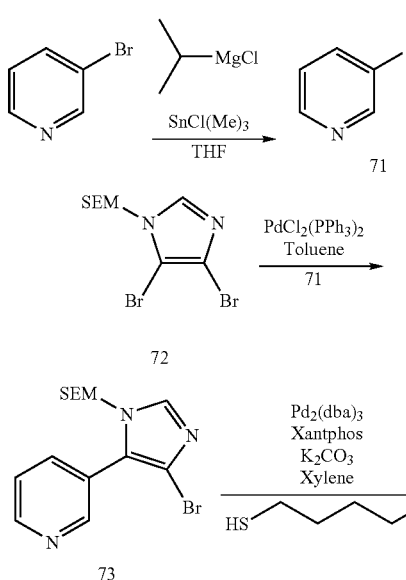

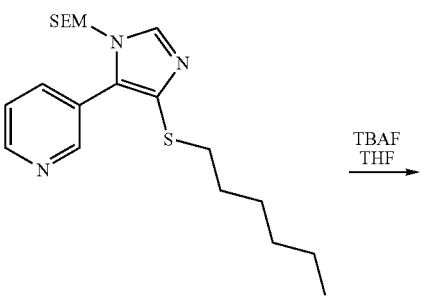
74B

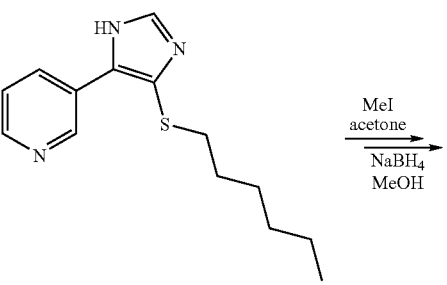
77

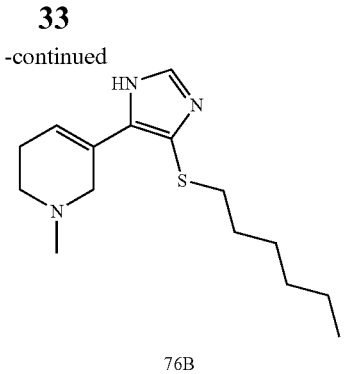

76B

§4. Syntheses of Specific Compounds

N-Methoxy-N-methyl-nicotinamide (Compound 2, Scheme 1)

Nicotinoyl chloride hydrochloride (compound 1) (10 g, 56 mmol) and 6.28 g of N,O-dimethyl-hydroxylamine.HCl (72.8 mmol) were combined in 200 ml dichloromethane. To this mixture was added 18.14 ml of pyridine (in 15 minutes at 0° C.). The reaction mixture was subsequently stirred for 4 hours at room temperature. The reaction was concentrated in vacuo. The resulting residue was taken up in dichloromethane and $H_2O$ (0° C.), washed with a 2N NaOH solution followed by brine, dried ($Na_2SO_4$), filtered and concentrated in vacuo. Purification by flash chromatography (MeOH/triethylamine 97/3) afforded compound 2 as an oil (6.92 g, 74%). $^1$H-NMR (200 MHz, $CDCl_3$) δ 8.96 (d, J=2 Hz, 1H), 8.69 (d, J=5 Hz, 2 Hz, 1H), 8.04 (dt, J=8 Hz, 2 Hz, 1H), 7.41-7.32 (m, 1H), 3.56 (s, 3H), 3.40 (s, 3H). (TLC MeOH/triethylamine $R_f$ 0.19).

1-Pyridin-3-yl-heptan-1-one (Compound 3, Scheme 1)

To a solution of anhydrous THF (15 ml) containing compound 2 (1.0 g, 6.02 mmol) was added 3.08 ml (7.66 mmol) of hexyl-lithium (2.5 M in hexane) dropwise at −78° C. under $N_2$. After the addition, the resulting solution was stirred for 30 minutes at −78° C. The mixture was allowed to warm to ambient temperature and poured into a $NH_4Cl$ solution (10 g/50 ml $H_2O$, 0° C.). Ethyl acetate was added and the organic layer was washed with a 5% $NaHCO_3$ solution, dried ($Na_2SO_4$), filtered and concentrated in vacuo. The resulting residue was purified by flash chromatography (diethyl ether/PE 1:1) to give compound 3 as an oil (0.91 g, 78%). $^1$H-NMR (200 MHz, $CDCl_3$): δ 9.18 (d, J=2 Hz, 1H), 8.78 (d, J=5 Hz, 2 Hz, 1H), 8.24 (dt, J=8 Hz, 2 Hz, 1H), 7.47-7.37 (m, 1H), 2.99 (t, J=7 Hz, 2H), 1.84-1.65 (m, 2H), 1.47-1.25 (m, 6H), 0.90 (bt, J=7 Hz, 3H).

2-Methylene-1-pyridin-3-yl-heptan-1-one (Compound 4, Scheme 1)

To 1 g (5.2 mmol) of compound 3, dissolved in 10 ml of MeOH, was added 0.1 ml of piperidine, 0.1 ml of acetic acid and 3 ml of an aqueous formaldehyde solution (37% formaldehyde in water). The mixture was heated to reflux for 48 hour. The mixture was cooled and concentrated in vacuo. Ethyl acetate was added and the organic layer was washed with a 5% $NaHCO_3$ solution, dried ($Na_2SO_4$), filtered and concentrated in vacuo. The resulting residue was purified by flash chromatography (diethyl ether/PE 1/1) to give compound 4 as an oil (1.05 g, 95%). $^1$H-NMR (200 MHz, $CDCl_3$): δ 8.94 (d, J=2 Hz, 1H), 8.76 (d, J=5 Hz, 2 Hz, 1H), 8.05 (dt, J=8 Hz, 2 Hz, 1H), 7.46-7.35 (m, 1H), 5.94 (s, 1H), 5.64 (s, 1H), 2.48 (bt, J=7 Hz, 2H), 1.60-1.25 (m, 6H), 0.99-0.82 (m, 3H).

1-(4-Pentyl-3-pyridin-3-yl-4,5-dihydropyrazol-1-yl)-ethanone (Compound 5, Scheme 1)

Compound 4 (3.37 g, 16.6 mmol) and 5.89 ml of hydrazine hydrate were dissolved in 50 ml of acetic acid and heated to reflux for 1.5 hour. The mixture was cooled and concentrated in vacuo. Ethyl acetate was added and the organic layer was washed with a 5% $NaHCO_3$ solution, dried ($Na_2SO_4$), filtered and concentrated in vacuo. The resulting residue was purified by flash chromatography (ether/ethyl acetate 1/1) to give compound 4. (amorphous, 2.92 g, 68%). $^1$H-NMR (600 MHz, $D_6DMSO$): δ 8.92 (d, J=2 Hz, 1H), 8.67-8.64 (m, 1H), 8.07 (bd, J=8 Hz, 1H), 7.39-7.36 (m, 1H), 4.04 (t, J=10 Hz, 1H), 3.96 (dd, J=10 Hz, J=5 Hz, 1H), 3.67-3.61 (m, 1H), 2.40 (s, 3H), 1.76-1.69 (m, 1H), 1.50-1.42 (m, 1H), 1.39-1.22 (m, 6H), 0.87 (bt, J=7 Hz, 3H).

3-(4-Pentyl-1H-pyrazol-3-yl)-pyridine (Compound 7, Scheme 1)

Compound 5 (0.9 g, 3.47 mmol) and 3.01 g of $MnO_2$ (10 eq.) were combined in dichloroethane (100 ml) and warmed to reflux for 2 hours (Dean Stark conditions).
Additional $MnO_2$ (6.02 g) was added and the mixture was refluxed for another 12 hours. The mixture was cooled, filtered and the filtrate was washed thoroughly with dichloroethane/isopropyl alcohol (1/1). This mixture was concentrated in vacuo to afford the oxidation product (6) (TLC ethyl acetate $R_f$ 0.20), contaminated with some starting material (5) (TLC ethyl acetate $R_f$ 0.27) and already deacylated product (7) (TLC ethyl acetate $R_f$ 0.12). This mixture (0.64 g) was used as in the next step without further purification.

The aforementioned material was dissolved in 5 ml of EtOH and 5 ml of 2 N NaOH and the reaction mixture was refluxed for 4 hours. The mixture was cooled and concentrated in vacuo. Ethyl acetate was added and the organic layer was washed with a 5% $NaHCO_3$ solution, dried ($Na_2SO_4$), filtered and concentrated in vacuo. The resulting residue was purified by flash chromatography (ethyl acetate) to afford the title compound (7) as an oil (344 mg, 1.6 mmol, 46% (overall)). $^1$H-NMR (200 MHz, $CDCl_3$): δ 8.88 (d, J=2 Hz, 1H), 8.60 (dd, J=5 Hz, 2 Hz, 1H), 7.92 (dt, J=8 Hz, 2 Hz, 1H), 7.47 (bs, 1H), 7.38-7.33 (m, 1H), 2.62 (t, J=7 Hz, 2H), 1.64-1.55 (m, 2H), 1.36-1.28 (m, 6H), 0.85 (bt, J=7 Hz, 3H).

3-(4-Pentyl-1H-pyrazol-3-yl)-1,2,5,6-tetrahydro-1-methylpyridine (Compound 9, Scheme 1)

Iodomethane (0.08 ml, 1.28 mmol) was added to a solution of 7 (130 mg, 0.6 mmol) in acetone (10 ml). After heating for 12 hours, the reaction mixture was cooled and the precipitated crystals were filtered, washed with diethyl ether and dried to afford compound 8. To a cooled (−30° C.) suspension of this pyridinium iodide derivative (8) in MeOH (15 ml), sodium borohydride (90 mg, 2.4 mmol) was added in small portions. The mixture was allowed to warm to ambient temperature and poured into a saturated $NH_4Cl$ solution (0° C.). The solvent was (partly) removed under reduced pressure. Ethyl acetate was added and the organic layer was washed with a concentrated $NaHCO_3$ solution, dried ($Na_2SO_4$), filtered and concentrated in vacuo. The resulting residue was purified by flash chromatography (MeOH/triethylamine 97/3) to afford the title compound 9 (amorphous, 63 mg, 45% (overall)). $^1$H-NMR (200 MHz, CDCl$_3$) δ 7.35 (bs, 1H), 6.07-6.00 (bs, 1H), 3.33-3.25 (m, 2H), 2.64-2.35 (m, 6H), 2.45 (s, 3H), 1.68-1.50 (m, 2H), 1.41-1.28 (m, 4H), 0.90 (bt, J=7 Hz, 3H).

N-Methoxy-N-methyl-2-pyridine-3-yl-acetamide (Compound 12, Scheme 2)

To a solution of anhydrous dichloromethane (200 ml) containing compound 10 (15.35 g, 88.4 mmol) was added 14.93 ml (163.3 mmol) of oxalyl chloride and a few drops of DMF. The mixture was gently refluxed for 8 hours under N$_2$. The mixture was cooled and concentrated, re-dissolved in dichloromethane and concentrated. The residue was dissolved in 200 ml of anhydrous dichloromethane and 11.09 g (113.7 mmol) of N,O-Dimethyl-hydroxylamine.HCl was added. To this mixture (0° C.) was added 2.73 ml of pyridine (in 15 minutes). The reaction mixture was subsequently stirred for 4 hours at room temperature. The reaction was concentrated in vacuo. The resulting residue was taken up in dichloromethane and H$_2$O (0° C.), washed with a 2N NaOH solution followed by brine, dried (Na$_2$SO$_4$), filtered and concentrated in vacuo. Purification by flash chromatography (ethyl acetate) afforded compound 12 as an oil (5.2 g, 33%). $^1$H-NMR (400 MHz, CDCl$_3$): δ 8.53-8.49 (m, 2H), 7.66 (bd, J=8 Hz, 1H), 7.29-7.24 (m, 1H), 3.78 (s, 2H), 3.68 (s, 3H), 3.20 (s, 3H).

1-Pyridin-3-yl-hexan-2-one (Compound 13, Scheme 2)

To a solution of anhydrous THF (15 ml) containing compound 12 (1.0 g, 5.5 mmol) was added 2.6 ml (6.5 mmol) of n-BuLi (2.5 M in hexanes) dropwise at −50° C. under N$_2$. After the addition, the resulting solution was stirred for 30 minutes at −50° C. The mixture was allowed to warm to ambient temperature and poured into a NH$_4$Cl solution (10 g/50 ml H$_2$O, 0° C.). Ethyl acetate was added and the organic layer was washed with a 5% NaHCO$_3$ solution, dried (Na$_2$SO$_4$), filtered and concentrated in vacuo. The resulting residue was purified by flash chromatography (ethyl acetate) to give compound 13 as an oil (0.21 g, 25%). $^1$H-NMR (400 MHz, CDCl$_3$): δ 8.50 (dd, J=5 Hz, 2 Hz, 1H), 8.45 (d, J=2 Hz, 1H), 7.54 (dt, J=8 Hz, J=2 Hz, 1H), 7.29-7.24 (m, 1H), 3.70 (s, 2H), 2.50 (t, J=7 Hz, 2H), 1.62-1.53 (m, 2H), 1.34-1.24 (m, 2H), 0.9 (bt, J=7 Hz, 3H).

1-Dimethylamino-2-pyridin-3-yl-hept-1-en-3-one. (Compound 14, Scheme 2)

A solution of 13 (2.0 g, 11 mmol) and DMFDMA (2.5 ml, 14.6 mmol) in dry t-BuOH was refluxed for 18 hours under N$_2$. The solution was allowed to attain room temperature and subsequently concentrated in vacuo. The resulting residue was purified by flash chromatography (ethyl acetate) to give compound 14 as an oil (1.85 g, 62%). $^1$H-NMR (400 MHz, CDCl$_3$): δ 8.51 (dd, J=5 Hz, 2 Hz, 1H), 8.45 (d, J=2 Hz, 1H), 7.66 (s, 1H), 7.53 (dt, J=8 Hz, J=2 Hz, 1H), 7.28-7.24 (m, 1H), 2.72 (bs, 6H), 2.20 (t, J=7 Hz, 2H), 1.54-1.46 (m, 2H), 1.26-1.16 (m, 2H), 0.9 (bt, J=7 Hz, 3H).

3-(4-Butyl-1H-pyrazol-3-yl)-pyridine (Compound 15, Scheme 2)

Compound 14 (0.95 g, 4 mmol) and 0.46 ml hydrazine hydrate (9.4 mmol) were dissolved in anhydrous ethanol (25 ml) and heated to reflux for 2 hours. The mixture was cooled and concentrated in vacuo. The resulting residue was purified by flash chromatography (ethyl acetate) to give compound 15. (amorphous, 0.7 g, 85%). $^1$H-NMR (200 MHz, CDCl$_3$): δ 8.65 (d, J=2 Hz, 1H), 8.52 (dd, J=5 Hz, 2 Hz, 1H), 7.72-7.67 (m, 2H), 7.35-7.31 (m, 1H), 2.82 (t, J=7 Hz, 2H), 1.70-1.62 (m, 2H), 1.42-1.33 (m, 2H), 0.9 (bt, J=7 Hz, 3H).

3-(4-Butyl-1H-pyrazol-3-yl)-1,2,5,6-tetrahydro-1-methylpyridine (Compound 16, Scheme 2)

Iodomethane (0.9 ml, 14 mmol) was added to a solution of 15 (600 mg, 3 mmol) in acetone (50 ml). After heating for 12 hours, the reaction mixture was cooled and the precipitated crystals were filtered, washed with diethyl ether and dried to afford the corresponding pyridinium iodide derivative. To a cooled (−30° C.) suspension of this pyridinium iodide derivative in MeOH (100 ml), sodium borohydride (0.5 g, 18.9 mmol) was added in small portions. The mixture was allowed to warm to ambient temperature and poured into a saturated NH$_4$Cl solution (0° C.). The solvent was (partly) removed under reduced pressure. Ethyl acetate was added and the organic layer was washed with a concentrated NaHCO$_3$ solution, dried (Na$_2$SO$_4$), filtered and concentrated in vacuo. The resulting residue was purified by flash chromatography (MeOH/triethylamine 97/3) to afford the title compound 16 (amorphous, 500 mg, 70% (overall)). $^1$H-NMR (400 MHz, CDCl$_3$): δ 7.40 (bs, 1H), 5.78-5.74 (bs, 1H), 3.15-3.05 (m, 2H), 2.71 (bt, J=7 Hz, 2H), 2.56 (t, J=6 Hz, 2H), 2.43 (s, 3H), 2.38-2.32 (m, 2H), 1.68-1.60 (m, 2H), 1.43-1.36 (m, 2H), 0.96 (t, J=7 Hz, 3H).

3-(4-Methylsulfanyl-1H-pyrazol-3-yl)-pyridine (Compound 21A, Scheme 3)

To a solution of anhydrous THF (150 ml) containing compound 20A (3.0 g, 13.4 mmol, prepared accordingly to Bioorganic & Medicinal Chemistry, 4, 1996, 227-237) was added 2.1 eq n-BuLi (11.2 ml, 2.5 M in hexane) dropwise at −78° C. under N$_2$. After the addition, the resulting solution was stirred for 2 hours at −78° C. At this temperature 1.1 eq methyldisulfanyl methane (1.33 ml) was added and the resulting solution was stirred for 1 hour at −78° C. and subsequently allowed to warm to ambient temperature overnight. Then the mixture was quenched with a saturated NH$_4$Cl solution at 0° C. and concentrated in vacuo. Ethyl acetate was added and the organic layer was washed with 5% NaHCO$_3$, dried (Na$_2$SO$_4$), filtered and concentrated in vacuo. Purification by flash chromatography (ethyl acetate) afforded compound 21A (oil, 1.71 g, 67%). $^1$H-NMR (200 MHz, CDCl$_3$): δ 9.18 (d, J=2 Hz, 1H), 8.60 (dd, J=5 Hz, 2 Hz, 1H), 8.28 (dt, J=8 Hz, 2 Hz, 1H), 7.70 (s, 1H), 7.42-7.33 (m, 1H), 2.38 (s, 3H).

3-(4-Methylsulfanyl-1H-pyrazol-3-yl)-1,2,5,6-tetrahydro-1-methylpyridine (Compound 22A, Scheme 3)

2.5 eq iodomethane (1.39 ml, 22.37 mmol) were added to a solution of 21A (1.71 g, 8.95 mmol) in acetone (100 ml) and the mixture was stirred for 18 hours. The precipitated crystals were filtered, washed with diethyl ether and dried to afford the corresponding pyridinium iodide derivative. To a cooled (−30° C.) suspension of this pyridinium iodide derivative in MeOH (100 ml), sodium borohydride (1.35 g, 35.5 mmol) was added in small portions. The mixture was allowed to warm to ambient temperature and poured into a saturated NH$_4$Cl solution (0° C.). The solvent was (partly) removed under reduced pressure. Ethyl acetate was added and the organic layer was washed with a concentrated NaHCO$_3$ solution, dried (Na$_2$SO$_4$), filtered and concentrated in vacuo. The resulting residue was purified by flash chromatography (MeOH) to afford the title compound 22A. (solid, 1.39 g, 74% (overall)). mp 131.5° C. LCMS (method A); R$_t$: 0.96 min, ([M+H]$^+$=210). $^1$H-NMR (400 MHz, CDCl$_3$): δ 7.52 (s, 1H), 6.56-6.46 (bs, 1H), 3.40-3.36 (m, 2H), 2.62 (bt, J=6 Hz, 2H), 2.46 (s, 3H), 2.45-2.38 (m, 2H), 2.30 (s, 3H).

3-[4-(4,4,4-trifluoro-butylsulfanyl)-1H-pyrazol-3-yl]-1,2,5,6-tetrahydro-1-methylpyridine (Compound 22B, Scheme 4)

A 60% dispersion of NaH in mineral oil (0.54 g, 13.64 mmol) was added to a solution of anhydrous THF (100 ml) containing compound 20A (2.79, 12.4 mmol) under N$_2$. The resulting mixture was stirred for 2 hours at room temperature and subsequently treated with 13.64 mmol (2.41 ml) of (2-Chloromethoxy-ethyl)-trimethylsilane (SEM-Cl). The resulting mixture was stirred for 18 hours at room temperature. Ethyl acetate was added to the mixture and the organic layer was washed three times with a saturated NaHCO$_3$ solution, dried (Na$_2$SO$_4$), filtered and concentrated. The resulting residue was purified by flash chromatography (diethyl ether/PE 1/1) to give a mixture of 27A (major component) and 27B as an oil (3.19 g, 73%). Carefully controlled purification by flash chromatography (diethyl ether/PE 1/1) gave 27B and subsequently 27A. Compound 27B (oil). $^1$H-NMR (400 MHz, CDCl$_3$): δ 9.15 (d, J=2 Hz, 1H), 8.60 (dd, J=5 Hz, 2 Hz, 1H), 8.20 (dt, J=8 Hz, 2 Hz, 1H), 7.71 (s, 1H), 7.38-7.34 (m, 1H), 5.44 (s, 2H), 3.64 (t, J=8 Hz, 2H), 0.94 (bt, J=8 Hz, 2H), 0.02 (s, 9H). Compound 27A (oil). $^1$H-NMR (400 MHz, CDCl$_3$): δ 8.90 (d, J=2 Hz, 1H), 8.75 (dd, J=5 Hz, 2 Hz, 1H), 7.96 (dt, J=8 Hz, 2 Hz, 1H), 7.63 (s, 1H), 7.47-7.42 (m, 1H), 5.34 (s, 2H), 3.70 (t, J=8 Hz, 2H), 0.92 (bt, J=8 Hz, 2H), 0.02 (s, 9H). NOESYPHSW and HMBCGP analyses were used to confirm both compounds.

To a solution of anhydrous THF (50 ml) containing a mixture of 27A/B (0.92 g, 2.6 mmol) was added 1.14 ml (1.1 eq) of n-BuLi (2.5 M in hexane) dropwise (−78° C. under N$_2$). After the addition, the resulting solution was stirred for 60 minutes at −78° C. At this temperature, sulfur powder (2.6 mmol, 0.083 g) was added and the reaction mixture was stirred for another 2 hours (−78° C.). The reaction was monitored by thin-layer chromatography. After the addition of 4-bromo-1,1,1-trifluoro-butane (1.1 eq, 0.54 ml), the mixture was allowed to warm to ambient temperature (overnight) and poured into a saturated NH$_4$Cl solution (0° C.). The solvent was (partly) removed under reduced pressure. Ethyl acetate was added and the organic layer was washed with a concentrated NaHCO$_3$ solution, dried (Na$_2$SO$_4$), filtered and concentrated in vacuo. The resulting residue was purified by flash chromatography (diethyl ether/PE 1/1)) to afford a mixture of (predominantly) 28A and 28B. (oil, 0.49 g, 45%). $^1$H-NMR (data of 28A are described, 400 MHz, CDCl$_3$): δ 8.80 (d, J=2 Hz, 1H), 8.70 (dd, J=5 Hz, 2 Hz, 1H), 7.96 (dt, J=8 Hz, 2 Hz, 1H), 7.68 (s, 1H), 7.48-7.43 (m, 1H), 5.35 (s, 2H), 3.72 (bt, J=8 Hz, 2H), 2.58 (t, J=7 Hz, 2H), 2.10-1.97 (m, 2H), 1.71-1.59 (m, 2H), 0.93 (bt, J=8 Hz, 2H), 0.00 (s, 9H).

To a solution of anhydrous THF (20 ml) containing a mixture of 28A/B (0.49 g, 1.18 mmol) was added 3.54 ml (3.0 eq) of TBAF (1.0 M in THF) under N$_2$. After the addition, the resulting solution was refluxed for 18 hours and subsequently concentrated in vacuo. Ethyl acetate was added and the organic layer was washed with a concentrated NaHCO$_3$ solution, dried (Na$_2$SO$_4$), filtered and concentrated in vacuo. The resulting residue was purified by flash chromatography (diethyl ether) to afford 3-[4-(4,4,4-Trifluoro-butylsulfanyl)-1H-pyrazol-3-yl]-pyridine (21B). (oil, 0.32 g, 95%). $^1$H-NMR (400 MHz, CDCl$_3$): δ 9.20 (d, J=2 Hz, 1H), 8.65 (dd, J=5 Hz, 2 Hz, 1H), 8.28 (dt, J=8 Hz, 2 Hz, 1H), 7.73 (s, 1H), 7.42-7.37 (m, 1H), 2.61 (t, J=7 Hz, 2H), 2.19-2.08 (m, 2H), 1.75-1.65 (m, 2H).

Compound 21B (0.3 g, 1.49 mmol) was converted to compound 22B, using the methodology described for the conversion of 21A to 22A. Yield 0.131 g (amorphous, 72% overall). LCMS (method A); R$_t$: 1.64 min, ([M+H]$^+$=306). $^1$H-NMR (400 MHz, CDCl$_3$): δ 7.57 (s, 1H), 6.67-6.60 (bs, 1H), 3.43-3.39 (m, 2H), 2.71-2.62 (m, 4H), 2.49 (s, 3H), 2.48-2.43 (m, 2H), 2.28-2.19 (m, 2H), 1.81-1.75 (m, 2H).

bis-[3-(1-Methyl-1,2,5,6-tetrahydro-pyridin-3-yl)-1H-pyrazol-4-yl)-2-sulfanylethyl]-methane (Compound 22C, Scheme 7)

A 60% dispersion of NaH in mineral oil (0.73 g, 18.3 mmol) was added to a solution of anhydrous THF (100 ml) containing compound 20A (3.71, 16.6 mmol) under N$_2$. The resulting mixture was stirred for 2 hours at room temperature and subsequently treated with 18.3 mmol (2.33 ml) Phenylsulfonyl chloride. The resulting mixture was stirred for 18 hours at room temperature. Ethyl acetate was added to the mixture and the organic layer was washed three times with a saturated NaHCO$_3$ solution, dried (Na$_2$SO$_4$), filtered and concentrated. The resulting residue was purified by flash chromatography (diethyl ether to afford 3-(1-phenylsulfonyl-4-bromo-1H-pyrazol-3-yl)-pyridine (36A). (TLC ethyl acetate R$_f$ 0.7) (amorphous, 5.34 g, 89%). $^1$H-NMR (400 MHz, CDCl$_3$): δ 9.1 (d, J=2 Hz, 1H), 8.65 (dd, J=5 Hz, 2 Hz, 1H), 8.24 (s, 1H), 8.16 (dt, J=8 Hz, 2 Hz, 1H), 8.10-8.05 (m, 2H), 7.70 (bt, J=7 Hz, 2H), 7.62-7.56 (m, 2H), 7.39-7.34 (m, 1H).

To a degassed solution of xylene (20 ml) containing 36 (0.7 g, 1.92 mmol), were added 0.45 eq (0.12 ml, 0.86 mmol) of pentane-1,5-di-thiol and 0.5 eq of K$_2$CO$_3$ (0.137 g, 0.96 mmol). The resulting mixture was stirred for another 2 hours under N$_2$. Successively were added 0.192 mmol of Pd$_2$(dba)$_3$ (176 mg) and 0.384 mmol of Xantphos (222 mg). After the addition, the resulting solution was refluxed for 18 hours under N$_2$. After cooling to room temperature, the mixture was diluted with ethyl acetate, washed three times with a saturated NaHCO$_3$ solution, dried (Na$_2$SO$_4$), filtered and concentrated. The resulting residue was purified by flash chromatography (ethyl acetate) to afford compound 37 as an oil (0.46 g, 68%). (TLC ethyl acetate R$_f$ 0.29).

Compound 37 (0.46 g, 0.65 mmol), 0.7 g KOH and 1 ml NH$_2$NH$_2$.H$_2$O were combined in diethylene glycol (10 ml) and warmed to reflux for 1 hour under N$_2$. The mixture was cooled, concentrated and re-dissolved in MeOH. Filtration over 5 g of SCX-2 (MeOH followed by 1 N NH$_3$/MeOH) and subsequent purification by flash chromatography (ethyl acetate) afforded bis-[3-pyridin-3-yl-1H-pyrazol-4-yl)-2-sulfanylethyl]-methane as the deprotected analog of 37 (amorphous, 0.23 g, 83%). $^1$H-NMR (400 MHz, CDCl$_3$): δ 9.15 (d, J=2 Hz, 2H), 8.57 (dd, J=5 Hz, 2 Hz, 2H), 8.31 (dt, J=8 Hz, 2 Hz, 2H), 7.66 (s, 2H), 7.36-7.32 (m, 2H), 2.50-2.42 (m, 4H), 1.34-1.26 (m, 6H).

The deprotected analog of compound 37 (0.23 g, 0.54 mmol) was converted to compound 22C, using the methodology described for the conversion of 21 A to 22A. Yield 0.2 g (oil, 80% overall). LCMS (method A); R$_t$: 1.66 min, ([M+H]$^+$=459). $^1$H-NMR (400 MHz, CDCl$_3$): δ 7.50 (s, 2H), 6.92-

6.85 (bs, 2H), 3.90-3.80 (m, 4H), 3.07 (bt, J=7 Hz, 4H), 2.77 (s, 6H), 2.66-2.54 (m, 8H), 1.54-1.43 (m, 6H).

3-(4-Ethylsulfanyl-1H-pyrazol-3-yl)-pyridine (Compound 21D)

Compound 21D was prepared following the procedure as described for the synthesis of compound 21A (see Scheme 3) using ethyldisulfanyl-ethane as the disulfide and 3-(4-bromo-1H-pyrazol-3-yl)-pyridine (compound 20A).

Yield: 76%. (oil). LCMS (Method A); $R_t$: 1.56 min, ([M+H]$^+$=206). $^1$H-NMR (200 MHz, CDCl$_3$): δ 9.11 (d, J=2 Hz, 1H), 8.64 (dd, J=5 Hz, 2 Hz, 1H), 8.18 (dt, J=8 Hz, 2 Hz, 1H), 7.71 (s, 1H), 7.39-7.35 (m, 1H), 2.64 (q, J=7 Hz, 2H), 1.26 (t, J=7 Hz, 3H).

3-(4-Ethylsulfanyl-1H-pyrazol-3-yl)-1,2,5,6-tetrahydro-1-methylpyridine (Compound 22D)

Compound 22D was prepared from compound 21D following the procedure as described for the synthesis of compound 22A (from 21A) (see Scheme 3).

Yield: 73% (solid). mp 95-97° C. LCMS (method A); $R_t$: 1.15 min, ([M+H]$^+$=224). $^1$H-NMR (mixture of rotational isomers (3/1), major one described, 400 MHz, CDCl$_3$): δ 7.53 (s, 1H), 6.55-6.46 (bs, 1H), 3.40-3.37 (m, 2H), 2.67-2.60 (m, 4H), 2.46 (s, 3H), 2.43-2.36 (m, 2H), 1.19 (3H).

3-(4-Propylsulfanyl-1H-pyrazol-3-yl)-pyridine (Compound 21E)

Compound 21E was prepared following the procedure as described for the synthesis of compound 21A using (see scheme 3) 1-propyldisulfanyl-propane as the disulfide and 3-(4-bromo-1H-pyrazol-3-yl)-pyridine (compound 20A). (flash chromatography conditions ethyl acetate/diethyl ether 5/1).

Yield: 76%. (oil). $^1$H-NMR (200 MHz, CDCl$_3$): δ 9.20 (d, J=2 Hz, 1H), 8.60 (dd, J=5 Hz, 2 Hz, 1H), 8.31 (dt, J=8 Hz, 2 Hz, 1H), 7.68 (s, 1H), 7.39-7.35 (m, 1H), 2.56 (t, J=7 Hz, 2H), 1.54-1.43 (m, 2H), 0.90 (t, J=7 Hz, 3H).

3-(4-Propylsulfanyl-1H-pyrazol-3-yl)-1,2,5,6-tetrahydro-1-methylpyridine (Compound 22E)

Compound 22E was prepared compound from 21E following the procedure as described for the synthesis of compound 22A (from 21A) (see Scheme 3). Yield: 77% (solid). mp 111° C. LCMS (method A); $R_t$: 1.39 min, ([M+H]$^+$=238). $^1$H-NMR (mixture of rotational isomers 8/1), major one described, 400 MHz, CDCl$_3$): δ 7.55 (s, 1H), 6.61-6.55 (bs, 1H), 3.43-3.39 (m, 2H), 2.68-2.60 (m, 4H), 2.48 (s, 3H), 2.46-2.39 (m, 2H), 1.58 (dq, J=7 Hz, 7 Hz, 2H), 0.98 (t, J=7 Hz, 3H).

3-(4-Butylsulfanyl-1H-pyrazol-3-yl)-pyridine (Compound 21F)

Compound 21F was prepared following the procedure as described for the synthesis of compound 21A (see Scheme 3) using 1-butyldisulfanyl-butane as the disulfide and 3-(4-iodo-1H-pyrazol-3-yl)-pyridine (compound 20B). (flash chromatography conditions ethyl acetate/diethyl ether 3/1).

Yield: 18.4%. (oil). $^1$H-NMR (200 MHz, CDCl$_3$): δ 9.20 (d, J=2 Hz, 1H), 8.60 (dd, J=5 Hz, 2 Hz, 1H), 8.31 (dt, J=8 Hz, 2 Hz, 1H), 7.68 (s, 1H), 7.39-7.34 (m, 1H), 2.58 (t, J=7 Hz, 2H), 1.48-1.40 (m, 2H), 1.36-1.25 (m, 2H), 0.90 (t, J=7 Hz, 3H).

3-(4-Butylsulfanyl-1H-pyrazol-3-yl)-1,2,5,6-tetrahydro-1-methylpyridine (Compound 22F)

Compound 22F was prepared from compound 21F following the procedure as described for the synthesis of compound 22A (from 21A) (see Scheme 3).

Yield: 73% (amorphous). Compound 22A was reacted with 1 equivalent of fumaric acid in EtOH and concentrated. Recrystallization from EtOH/ethyl acetate afforded a solid (free base/fumaric acid 1/1), mp 120-121° C. LCMS (method A); $R_t$: 1.16 min, ([M+H]$^+$=252).

3-(4-Pentylsulfanyl-1H-pyrazol-3-yl)-pyridine (Compound 21G)

Compound 21G was prepared following the procedure as described for the synthesis of compound 21A (see Scheme 3) using 1-pentyldisulfanyl-pentane as the disulfide and 3-(4-bromo-1H-pyrazol-3-yl)-pyridine (compound 20A).

Yield: 71%. (oil). $^1$H-NMR (400 MHz, CDCl$_3$): δ 9.18 (d, J=2 Hz, 1H), 8.60 (dd, J=5 Hz, 2 Hz, 1H), 8.32 (dt, J=8 Hz, 2 Hz, 1H), 7.66 (s, 1H), 7.39-7.34 (m, 1H), 2.57 (t, J=7 Hz, 2H), 1.48-1.41 (m, 2H), 1.30-1.14 (m, 4H), 0.81 (t, J=7 Hz, 3H).

3-(4-Pentylsulfanyl-1H-pyrazol-3-yl)-1,2,516-tetrahydro-1-methylpyridine (Compound 22G)

Compound 22G was prepared from compound 21G following the procedure as described for the synthesis of compound 22A (from 21A) (see Scheme 3).

Yield: 77% (solid). mp 100-101° C. LCMS (method A); $R_t$: 1.67 min, ([M+H]$^+$=266). $^1$H-NMR (400 MHz, CDCl$_3$): δ 7.51 (s, 1H), 6.56-6.47 (bs, 1H), 3.40-3.36 (m, 2H), 2.65-2.59 (m, 4H), 2.45 (s, 3H), 2.44-2.38 (m, 2H), 1.57-1.47 (m, 4H), 1.39-1.24 (m, 4H) 0.88 (t, J=7 Hz, 3H).

3-(4-Hexylsulfanyl-1H-pyrazol-3-yl)-pyridine (Compound 21H)

Compound 21H was prepared following the procedure as described for the synthesis of compound 21A (see Scheme 3) using 1-hexyldisulfanyl-hexane as the disulfide and 3-(4-iodo-1H-pyrazol-3-yl)-pyridine (compound 20B).

Yield: 37%. (oil). $^1$H-NMR (400 MHz, CDCl$_3$): δ 9.18 (d, J=2 Hz, 1H), 8.62 (dd, J=5 Hz, 2 Hz, 1H), 8.31 (dt, J=8 Hz, 2 Hz, 1H), 7.70 (s, 1H), 7.40-7.35 (m, 1H), 2.59 (t, J=7 Hz, 2H), 1.50-1.42 (m, 2H), 1.34-1.12 (m, 6H), 0.81 (t, J=7 Hz, 3H).

3-(4-Hexylsulfanyl-1H-pyrazol-3-yl)-1,2,5,6-tetrahydro-1-methylpyridine (Compound 22H)

Compound 22H was prepared from compound 21H following the procedure as described for the synthesis of compound 22A (from 21A) (see Scheme 3).

Yield: 49% (amorphous). LCMS (method A); $R_t$: 1.81 min, ([M+H]$^+$=280). $^1$H-NMR (400 MHz, CDCl$_3$): δ 7.51 (s, 1H), 6.60-6.50 (bs, 1H), 3.40-3.36 (m, 2H), 2.65-2.59 (m, 4H), 2.45 (s, 3H), 2.44-2.38 (m, 2H), 1.56-1.48 (m, 2H), 1.39-1.20 (m, 6H) 0.88 (t, J=7 Hz, 3H).

3-[4-(3-Phenyl-propylsulfanyl)-1H-pyrazol-3-yl]-pyridine (Compound 21I)

Compound 21I was prepared following the procedure as described for the synthesis of compound 21A (see Scheme 3)

using 3-phenyl-propyldisulfanyl-3-propylbenzene as the disulfide (prepared according to the methodology described in Tetrahedron Letters, 42, 2001, 6741-6743) and 3-(4-bromo-1H-pyrazol-3-yl)-pyridine (compound 20A). (conditions flash chromatography (ethyl acetate)) Yield: 22% (oil). $^1$H-NMR (400 MHz, CDCl$_3$): δ 9.18 (d, J=2 Hz, 1H), 8.62 (dd, J=5 Hz, 2 Hz, 1H), 8.31 (dt, J=8 Hz, 2 Hz, 1H), 7.69 (s, 1H), 7.40-7.36 (m, 1H), 7.24 (bt, J=7 Hz, 2H), 7.17 (bt, J=7 Hz, 1H), 7.04 (bd, J=7 Hz, 2H), 2.65-2.57 (m, 4H), 1.84-1.75 (m, 2H).

3-[4-(3-Phenyl-propylsulfanyl)-1H-pyrazol-3-yl]-1,2,5,6-tetrahydro-1-methylpyridine (Compound 22I)

Compound 22I was prepared from compound 21I following the procedure as described for the synthesis of compound 22A (from 21A) (see Scheme 3).
Yield: 59% (amorphous). $^1$H-NMR (400 MHz, CDCl$_3$): δ 7.51 (s, 1H), 7.30-7.22 (m, 2H), 7.21-7.12 (m, 3H), 6.66-6.46 (bs, 1H), 3.39-3.34 (m, 2H), 2.70-2.55 (m, 6H), 2.44 (s, 3H), 2.43-2.36 (m, 2H), 1.89-1.80 (m, 2H).

3-[4-(4,4-Difluoro-but-3enylsulfanyl)-1H-pyrazol-3-yl]-pyridine (Compound 21J)

Compound 21J was prepared following the procedure as described for the synthesis of compound 21A (see Scheme 3) using 4-(4,4-difluoro-but-3-enyldisulfanyl)-1,1-difluoro-but-1-ene as the disulfide (Tetrahedron Letters, 42, 2001, 6741-6743) and 3-(4-bromo-1H-pyrazol-3-yl)-pyridine (compound 20A). (conditions flash chromatography (ethyl acetate)) Yield: 58% (oil). $^1$H-NMR (400 MHz, CDCl$_3$): δ 9.18 (d, J=2 Hz, 1H), 8.62 (dd, J=5 Hz, 2 Hz, 1H), 8.31 (dt, J=8 Hz, 2 Hz, 1H), 7.72 (s, 1H), 7.42-7.36 (m, 1H), 4.19-4.06 (m, 1H), 2.59 (t, J=7 Hz, 2H), 2.18-2.09 (m, 2H).

3-[4-(4,4-Difluoro-but-3enylsulfanyl)-1H-pyrazol-3-yl]-1,2,5,6-tetrahydro-1-methylpyridine (Compound 22J)

Compound 22J was prepared from compound 21H following the procedure as described for the synthesis of compound 22A (from 21A) (see Scheme 3). Yield: 90% (amorphous). $^1$H-NMR (400 MHz, CDCl$_3$): δ 7.54 (s, 1H), 6.68-6.44 (bs, 1H), 4.27-4.15 (m, 1H), 3.40-3.36 (m, 2H), 2.66-2.60 (m, 4H), 2.47 (s, 3H), 2.45-2.38 (m, 2H), 2.22-2.14 (m, 2H).

3-[4-(3-Phenyl-allylsulfanyl)-1H-pyrazol-3-yl]-pyridine (Compound 21 K)

Compound 21K was prepared following the procedure as described for the synthesis of compound 21A (see Scheme 3) using 3-phenyl-allyldisulfanyl-3-alkylbenzene as the disulfide (Tetrahedron Letters, 42, 2001, 6741-6743) and 3-(4-bromo-1H-pyrazol-3-yl)-pyridine (compound 20A). (conditions flash chromatography (ethyl acetate)). Yield: 22%. (oil), (TLC ethyl acetate R$_f$ 0.45).

3-[4-(3-Phenyl-allylsulfanyl)-1H-pyrazol-3-yl]-1,2,5,6-tetrahydro-1-methylpyridine (Compound 22K)

Compound 22K was prepared from compound 21K following the procedure as described for the synthesis of compound 22A (from 21A) (see Scheme 3).
Yield: 72% (amorphous). $^1$H-NMR (400 MHz, CDCl$_3$): δ 7.52 (s, 1H), 7.30-7.18 (m, 5H), 6.70-6.20 (bs, 1H), 6.20-6.07 (m, 2H), 3.37 (d, J=7 Hz, 2H), 3.33-3.28 (m, 2H), 2.54 (bt, J=7 Hz, 2H), 2.40 (s, 3H), 2.39-2.30 (m, 2H).

3-[4-Pent-4-enylsulfanyl)-1H-pyrazol-3-yl]-pyridine (Compound 21L)

Compound 21L was prepared following the procedure as described for the synthesis of compound 21A (see Scheme 3) using 5-pent-4-enyldisulfanyl-pent-1-ene as the disulfide (Tetrahedron Letters, 42, 2001, 6741-6743) and 3-(4-iodo-1H-pyrazol-3-yl)-pyridine (compound 20B). (conditions flash chromatography (ethyl acetate)) Yield: 28%. (oil). LCMS (method A); R$_t$: 2.21 min, ([M+H]$^+$=246). $^1$H-NMR (400 MHz, CDCl$_3$): δ 9.20 (d, J=2 Hz, 1H), 8.62 (dd, J=5 Hz, 2 Hz, 1H), 8.31 (dt, J=8 Hz, 2 Hz, 1H), 7.71 (s, 1H), 7.41-7.35 (m, 1H), 5.73-5.59 (m, 2H), 4.97-4.89 (m, 2H), 2.59 (t, J=7 Hz, 2H), 2.10-2.03 (m, 2H), 1.61-1.54 (m, 2H).

3-[4-Pent-4-enylsulfanyl)-1H-pyrazol-3-yl]-1,2,5,6-tetrahydro-1-methylpyridine (Compound 22L)

Compound 22L was prepared from compound 21L following the procedure as described for the synthesis of compound 22A (from 21A) (see Scheme 3). Yield: 61% (amorphous). LCMS (method A); R$_t$: 1.84 min, ([M+H]$^+$=264). $^1$H-NMR (400 MHz, CDCl$_3$): δ 7.52 (s, 1H), 6.70-6.40 (bs, 1H), 5.81-5.68 (m, 1H), 5.04-4.94 (m, 2H), 3.40-3.36 (m, 2H), 2.66-2.57 (m, 4H), '2.45 (s, 3H), 2.45-2.37 (m, 2H), 2.17-2.09 (m, 2H), 1.66-1.58 (m, 2H).

3-[4-(Furan-2-ylmethylsulfanyl)-1H-pyrazol-3-yl]-pyridine (Compound 21M)

Compound 21M was prepared following the procedure as described for the synthesis of compound 21A (see scheme 3) using difurfuryl-disulfide and 3-(4-iodo-1H-pyrazol-3-yl)-pyridine (compound 20B). (conditions flash chromatography (ethyl acetate)) Yield: 54%. (oil). $^1$H-NMR (200 MHz, CDCl$_3$): δ 9.20 (d, J=2 Hz, 1H), 8.59 (dd, J=5 Hz, 2 Hz, 1H), 8.20 (dt, J=8 Hz, 2 Hz, 1H), 7.54 (s, 1H), 7.38-7.32 (m, 1H), 7.21-7.19 (m, 1H), 6.16-6.12 (m, 1H), 5.88-5.84 (m, 1H), 3.75 (s, 2H).

3-[4-(Furan-2-yl-methylsulfanyl)-1H-pyrazol-3-yl]-1,2,5,6-tetrahydro-1-methylpyridine (Compound 22M)

Compound 22M was prepared from compound 21M following the procedure as described for the synthesis of compound 22A (see Scheme 3). Yield: 65% (amorphous). LCMS (method A); R$_t$: 1.04 min, ([M+H]$^+$=276). $^1$H-NMR (200 MHz, CDCl$_3$): δ 7.36 (s, 1H), 7.33-7.31 (m, 1H), 6.38-6.26 (bs, 1H), 6.24-6.20 (m, 1H), 5.93-5.90 (m, 1H), 3.78 (s, 2H), 3.30-3.22 (m, 2H), 2.60 (bt, J=7 Hz, 2H), 2.44 (s, 3H), 2.41-2.33 (m, 2H).

3-(4-Benzylsulfanyl-1H-pyrazol-3-yl)-pyridine (Compound 21N)

Compound 21N was prepared following the procedure as described for the synthesis of compound 21A (see Scheme 3) using dibenzyl-disulfide and 3-(4-iodo-1H-pyrazol-3-yl)-pyridine (compound 20B). (conditions flash chromatography (ethyl acetate)) Yield: 33%. (oil). $^1$H-NMR (400 MHz, CDCl$_3$): δ 9.0 (d, J=2 Hz, 1H), 8.58 (dd, J=5 Hz, 2 Hz, 1H), 8.10 (dt, J=8 Hz, 2 Hz, 1H), 7.43 (s, 1H), 7.33-7.28 (m, 1H), 7.17-7.11 (m, 3H), 7.02-6.96 (m, 2H), 3.72 (s, 2H).

3-(4-Benzylsulfanyl-1H-pyrazol-3-yl)-1,2,5,6-tetrahydro-1-methylpyridine (Compound 22N)

Compound 22N was prepared from compound 21N following the procedure as described for the synthesis of compound 22A (from 21A) (see Scheme 3). Yield: 48% (amorphous). LCMS (method A); $R_t$: 1.55 min, ([M+H]$^+$=286). Compound 22N was reacted with 1 equivalent of fumaric acid in EtOH and concentrated. $^1$H-NMR (600 MHz, D$_6$DMSO): δ 7.63 (s, 1H), 7.28 (t, J=7 Hz, 2H), 7.28 (t, J=7 Hz, 2H), 7.24 (bt, J=7 Hz, 1H), 7.17 (bd, J=7 Hz, 2H), 6.82-6.79 (bs, 1H), 6.66 (s, 2H), 4.28 (bd, J=15 Hz, 1H), 4.05 (dd, J=16 Hz, 6 Hz, 2H), 3.86-3.80 (m, 1H), 3.55-3.50 (m, 1H), 3.18-3.10 (m, 1H), 2.94 and 2.93 (2×s, 3H), 2.68-2.46 (m, 2H).

3-[4-(2-Ethoxy-ethylsulfanyl)-1H-pyrazol-3-yl]-pyridine (Compound 21O)

Compound 21O was prepared following the procedure as described for the synthesis of compound 21A (see Scheme 3) using 1-ethoxy-2-(2-ethoxy-ethyldisulfanyl)-ethane as the disulfide (Tetrahedron Letters, 42, 2001, 6741-6743) and 3-(4-iodo-1H-pyrazol-3-yl)-pyridine (compound 20B). (conditions flash chromatography (ethyl acetate)) Yield: 28%. (oil). LCMS (method A); $R_t$: 2.21 min, ([M+H]$^+$=246). $^1$H-NMR (400 MHz, CDCl$_3$): δ 9.20 (d, J=2 Hz, 1H), 8.62 (dd, J=5 Hz, 2 Hz, 1H), 8.33 (dt, J=8 Hz, 2 Hz, 1H), 7.75 (s, 1H), 7.41-7.36 (m, 1H), 3.46 (t, J=7 Hz, 2H), 3.38 (q, J=7 Hz, 2H), 2.78 (t, J=7 Hz, 2H), 1.14 (t, J=7 Hz, 3H),

3-[4-(2-Ethoxy-ethylsulfanyl)-1H-pyrazol-3-yl]-1,2,5,6-tetrahydro-1-methylpyridine (Compound 22O)

Compound 22O was prepared from compound 21O following the procedure as described for the synthesis of compound 22A (from 21A) (see Scheme 3). Yield: 63% (amorphous). $^1$H-NMR (400 MHz, CDCl$_3$): δ 7.56 (s, 1H), 6.70-6.50 (bs, 1H), 3.55-3.43 (m, 4H), 3.40-3.36 (m, 2H), 2.81 (t, J=7 Hz, 2H), 2.61 (bt, J=7 Hz, 2H), 2.46 (s, 3H), 2.44-2.38 (m, 2H), 1.18 (t, J=7 Hz, 3H).

3-{4-[2-(2-Methoxy-ethoxy)-ethylsulfanyl]-1H-pyrazol-3-yl}-pyridine (Compound 21P)

Compound 21P was prepared following the procedure as described for the synthesis of compound 21$^a$ (see Scheme 3) using 1-methoxy-2-{2-[2-((2-methoxy-ethoxy)-ethyldisulfanyl]-ethoxy}-ethane as the disulfide (Tetrahedron Letters, 42, 2001, 6741-6743) and 3-(4-iodo-1H-pyrazol-3-yl)-pyridine (compound 20B). (conditions flash chromatography (ethyl acetate)) Yield: 36%. (oil). $^1$H-NMR (400 MHz, CDCl$_3$): δ 9.18 (d, J=2 Hz, 1H), 8.58 (dd, J=5 Hz, 2 Hz, 1H), 8.35 (dt, J=8 Hz, 2 Hz, 1H), 7.78 (s, 1H), 7.39-7.32 (m, 1H), 3.51-3.44 (m, 6H), 3.34 (s, 3H), 2.78 (t, J=7 Hz, 2H).

3-[4-[2-(2-Methoxy-ethoxy)-ethylsulfanyl]-1H-pyrazol-3-yl]-1,2,5,6-tetrahydro-1-methylpyridine (Compound 22P)

Compound 22P was prepared from compound 21P following the procedure as described for the synthesis of compound 22A (from 21A) (see Scheme 3). Yield: 33% (amorphous). $^1$H-NMR (400 MHz, CDCl$_3$): δ 7.57 (s, 1H), 6.74-6.69 (bs, 1H), 3.59-3.51 (m, 8H), 3.38 (s, 3H), 2.83 (t, J=7 Hz, 2H), 2.77 (bt, J=7 Hz, 2H), 2.55 (s, 3H), 2.52-2.45 (m, 2H).

3-(4-Allylsulfanyl-1H-pyrazol-3-yl)-pyridine (Compound 21Q)

Compound 21Q was prepared following the procedure as described for the synthesis of compound 21A (see Scheme 3) using 3-allyldisulfanyl-propene as the disulfide and 3-(4-iodo-1H-pyrazol-3-yl)-pyridine (compound 20B). (conditions flash chromatography (ethyl acetate)) Yield: 27%. (oil). $^1$H-NMR (200 MHz, CDCl$_3$): δ 9.20 (d, J=2 Hz, 1H), 8.60 (dd, J=5 Hz, 2 Hz, 1H), 8.29 (dt, J=8 Hz, 2 Hz, 1H), 7.70 (s, 1H), 7.40-7.36 (m, 1H), 5.77-5.66 (m, 1H), 4.94 (bdd, J=11 Hz, 1 Hz, 1H), 4.83 (bdd, J=17 Hz, 1 Hz, 1H), 3.19 (bd, J=8 Hz, 2H).

3-(4-Allylsulfanyl-1H-pyrazol-3-yl)-1,2,5,6-tetrahydro-1-methylpyridine (Compound 22Q)

Compound 22Q was prepared from compound 21Q following the procedure as described for the synthesis of compound 22A (from 21A) (see Scheme 3). Yield: 17% (amorphous). $^1$H-NMR (200 MHz, CDCl$_3$): δ 7.52 (s, 1H), 6.62-6.48 (bs, 1H), 5.84-5.74 (m, 1H), 4.98 (bdd, J=11 Hz, 1 Hz, 1H), 4.90 (bdd, J=17 Hz, 1 Hz, 1H), 4.00-3.95 (m, 2H), 3.23 (bd, J=8 Hz, 2H), 2.61 (bt, J=7 Hz, 2H), 2.46 (s, sH), 2.44-2.39 (m, 2H).

3-(3-Pyridin-3-yl-1H-pyrazol-4-ylsulfanyl)-propionitrile (Compound 21R)

Compound 21R was prepared following the procedure as described for the synthesis of compound 21A (see Scheme 3) using 3-(2-cyano-ethyldisulfanyl)-propionitrile as the disulfide and 3-(4-iodo-1H-pyrazol-3-yl)-pyridine (compound 20B). (conditions flash chromatography (ethyl acetate)) Yield: 62%. (oil). $^1$H-NMR (200 MHz, CDCl$_3$): δ 9.20 (d, J=2 Hz, 1H), 8.60 (dd, J=5 Hz, 2 Hz, 1H), 8.33 (dt, J=8 Hz, 2 Hz, 1H), 7.82 (s, 1H), 7.43-7.37 (m, 1H), 2.76 (t, J=7 Hz, 2H), 2.45 (t, J=7 Hz, 2H).

3-[3-(1-Methyl-1,2,5,6-tetrahydro-pyridin-3-yl)-1H-pyrazol-4-ylsulfanyl]-propionitrile (Compound 22R)

Compound 22R was prepared from compound 21R following the procedure as described for the synthesis of compound 22A (from 21A) (see Scheme 3). Yield: 8% (amorphous). $^1$H-NMR (200 MHz, CDCl$_3$): δ 7.58 (s, 1H), 6.60-6.50 (bs, 1H), 3.40-3.36 (m, 2H), 2.79 (t, J=7 Hz, 2H), 2.66 (bt, J=7 Hz, 2H), 2.50 (t, J=7 Hz, 2H), 2.47 (s, 3H), 2.45-2.38 (m, 2H).

3-[4-(3-methyl-butylsulfanyl)-1H-pyrazol-3-yl]-pyridine (Compound 21S)

Compound 21S was prepared following the procedure as described for the synthesis of compound 21A (see Scheme 3) using 3-Methyl-1-(3-methyl-butyldisulfanyl)-butane as the disulfide and 3-(4-iodo-1H-pyrazol-3-yl)-pyridine (compound 20B). (conditions flash chromatography (ethyl acetate)) Yield: 39%. (oil). $^1$H-NMR (200 MHz, CDCl$_3$): δ 9.18 (d, J=2 Hz, 1H), 8.65 (dd, J=5 Hz, 2 Hz, 1H), 8.35 (dt, J=8 Hz, 2 Hz, 1H), 7.78 (s, 1H), 7.39-7.35 (m, 1H), 2.60 (t, J=7 Hz, 2H), 1.65-1.57 (m, 1H), 1.42-1.33 (m, 2H), 0.81 (d, J=7 Hz, 6H).

3-[4-(3-methyl-butylsulfanyl)-1H-pyrazol-3-yl]-1,2,5,6-tetrahydro-1-methylpyridine (Compound 22S)

Compound 22S was prepared from compound 21S following the procedure as described for the synthesis of compound 22A (from 21A) (see Scheme 3). Yield: 73% (amorphous). $^1$H-NMR (200 MHz, CDCl$_3$): δ 7.5 (s, 1H), 6.60-6.48 (bs, 1H), 3.40-3.36 (m, 2H), 2.66-2.59 (m, 4H), 2.45 (s, 3H), 2.44-2.39 (m, 2H), 1.72-1.62 (m, 1H), 1.45-1.39 (m, 2H), 0.86 (d, J=7 Hz, 6H).

3-Pyridin-3-yl-pyrazole-1-sulfonic acid dimethylamide (Compound 23, Scheme 3)

Compound 19 (3.0 g, 20.7 mmol) and 2.22 ml of phenylsulfonyl chloride (20.7 mmol) were combined in pyridine (100 ml) and stirred for 18 hours at reflux. The reaction was concentrated in vacuo. The residue was taken up in ethyl acetate, washed three times with a saturated NaHCO$_3$ solution, dried (Na$_2$SO$_4$), filtered and concentrated in vacuo. The resulting residue was purified by flash chromatography (diethyl ether/PE 2/1) to afford the afford compound 23 (amorphous, 2.86 g, 55%). $^1$H-NMR (200 MHz, CDCl$_3$): δ 9.1 (d, J=2 Hz, 1H), 8.6 (dd, J=5 Hz, 2 Hz, 1H), 8.16 (dt, J=8 Hz, 2 Hz, 1H), 8.05 (d, J=3 Hz, 1H), 7.39-7.34 (m, 1H), 6.75 (d, J=3 Hz, 1H), 3.02 (s, 6H).

5-Butylsulfanyl-3-pyridin-3-yl-pyrazol-1-sulfonic acid dimethylamide (Compound 24, Scheme 3)

To a solution of anhydrous THF (50 ml) containing compound 24 (1.0 g, 4 mmol) was added 1 eq of n-BuLi (2.35 ml, 1.7 M in pentane) dropwise at −78° C. under N$_2$. After the addition, the resulting solution was stirred for 1 hour at −78° C. At this temperature 1.1 eq 1-butyldisulfanyl-butane (0.79 ml) was added and the resulting solution was stirred for 1 hour at −78° C. and subsequently allowed to warm to ambient temperature overnight. Then the mixture was quenched with a saturated NH$_4$Cl solution at 0° C. and concentrated in vacuo. Ethyl acetate was added and the organic layer was washed with a 5% NaHCO$_3$ solution, dried (Na$_2$SO$_4$), filtered and concentrated in vacuo. Purification by flash chromatography (diethyl ether/PE 5/1) to ethyl acetate/diethyl ether 1/1) afforded compound 24 (oil, 0.93 g, 70%). $^1$H-NMR (200 MHz, CDCl$_3$): 9.1 (d, J=2 Hz, 1H), 8.6 (dd, J=5 Hz, 2 Hz, 1H), 8.15 (dt, J=8 Hz, 2 Hz, 1H), 7.39-7.34 (m, 1H), 6.50 (s, 1H), 3.02 (s, 6H), 3.02 (t, J=7 Hz, 2H), 1.82-1.67 (m, 2H), 1.60-1.42 (m, 2H), 0.97 (t, J=7 Hz, 3H).

3-(5-Butylsulfanyl-1H-pyrazol-3-yl)-pyridine (Compound 25, Scheme 3)

Compound 24 (0.92 g, 2.71 mmol) was dissolved in 50 ml of n-BuOH. To this solution was added 2 g of KOH dissolved in 50 ml of H$_2$O and the reaction mixture was stirred for 18 hours at room temperature under N$_2$. The reaction mixture was concentrated in vacuo. The resulting residue was taken up in ethyl acetate, washed with a 5% NaHCO$_3$ solution, dried (Na$_2$SO$_4$), filtered and concentrated in vacuo. Purification by flash chromatography (diethyl ether/PE 4/1) afforded compound 25 (amorphous, 0.44 g, 70%). (TLC ethyl acetate R$_f$ 0.34).

3-(5-Butylsulfanyl-1H-pyrazol-3-yl)-1,2,5,6-tetrahydro-1-methylpyridine (Compound 26, Scheme 3)

Compound 26 was prepared following the procedure as described for the synthesis of compound 22A (from 21A). Yield: 70% (amorphous). $^1$H-NMR (200 MHz, CDCl$_3$): δ 6.27 (s, 1H), 6.22-6.18 (bs, 1H), 3.31-3.27 (m, 2H), 2.82 (t, J=7 Hz, 2H), 2.58 (bt, J=7 Hz, 2H), 2.44 (s, 3H), 2.39-2.32 (m, 2H), 1.62-1.54 (m, 2H), 1.44-1.37 (m, 2H), 0.86 (t, J=7 Hz, 3H).

3-[4-(3-Phenyl-propoxy)-1H-pyrazol-3-yl]-1,2,5,6-tetrahydro-1-methylpyridine (Compound 33A, Scheme 5)

A 60% dispersion of NaH in mineral oil (3 g, 1.1 eq) was added to a solution of anhydrous THF (100 ml) containing compound 20B (18.36 g, 68.74 mmol) under N$_2$. The resulting mixture was stirred for 2 hours at room temperature and subsequently treated with 13.37 ml (1.1 eq) of (2-chloromethoxy-ethyl)-trimethylsilane (SEM-Cl). The resulting mixture was stirred for 18 hours at room temperature. Ethyl acetate was added to the mixture and the organic layer was washed three times with a saturated NaHCO$_3$ solution, dried (Na$_2$SO$_4$), filtered and concentrated. The resulting residue was purified by flash chromatography (diethyl ether/PE 1/1) to give a (variable) mixture of 29A and 29B as an oil (23.09 g, 83%). $^1$H-NMR (400 MHz, CDCl$_3$): The NMR shows great resemblance with the NMR of the mixture of 27A/B (see Scheme 4), major isomer (presumably 29A) is given: δ 9.15 (d, J=2 Hz, 1H), 8.65 (dd, J=5 Hz, 2 Hz, 1H), 8.17 (dt, J=8 Hz, 2 Hz, 1H), 7.74 (s, 1H), 7.39-7.34 (m, 1H), 5.46 (s, 2H), 3.71-3.62 (m, 4H, both isomers), 0.98-0.84 (m, 4H, both isomers), 0.02 (both isomers, Si(CH$_3$)$_3$).

To a solution of anhydrous THF (250 ml) containing a mixture of 29A/B (10 g, 25 mmol) was added 10.5 ml (1.1 eq) of n-BuLi (2.5 M in hexane) dropwise (−78° C. under N$_2$). After the addition, the resulting solution was stirred for 60 minutes at −78° C. At this temperature, trimethyl borate (3 eq, 8.50 ml) was added (dropwise in 15 minutes) and the reaction mixture was stirred for another 2 hours at −78° C. The reaction mixture was then allowed to warm to ambient temperature (overnight).

The temperature of the reaction mixture was lowered to −10° C. and 2.2 ml (1.5 eq) of acetic acid was added. Subsequently, 1.1 eq of a 30% H$_2$O$_2$ solution (2.93 ml) was added dropwise, while keeping the temperature <−5° C. The mixture was allowed to warm to ambient temperature and stirred for another 4 hours. To the reaction mixture was added 10 ml of H$_2$O and subsequently ethyl acetate (500 ml). The organic layer was washed with a 5% NaHCO$_3$ solution, dried (Na$_2$SO$_4$), filtered and concentrated in vacuo. The resulting residue was purified by flash chromatography (diethyl ether followed by ethyl acetate) to afford 3-pyridin-3-yl-1-(2-trimethylsilanyl-1-ethoxymethyl)-1H-pyrazol-4-ol (30), as a (variable) mixture of the SEM protected product isomers. (amorphous, 2.9 g, 40%). $^1$H-NMR (400 MHz, CDCl$_3$, mixture of isomers ~1/1): δ 9.22 and 8.90 (2×bs, 1H), 8.47-8.18 (m, 2H), 7.45-7.34 (m, 1H), 7.36 and 7.31 (2×s, 1H), 5.36 and 5.35 (2×s, 2H), 3.74-3.69 and 3.64-3.59 (2×m, 2H), 0.99-0.90 (m, 2H), 0.02 and 0.01 (2×s, 9H)

To a solution of anhydrous DMF (50 ml) containing compound 30 (2.03 g, 6.98 mmol) were added 1.5 eq of K$_2$CO$_3$ (1.45 g) and the mixture was stirred for 1 hour under N$_2$. After the addition of 3-bromo-propylbenzene (1.1 eq, 1.17 ml), the resulting solution was stirred for 18 hours at 45° C. and allowed to reach ambient temperature. Ethyl acetate was added and the organic layer was washed with a concentrated NaHCO$_3$ solution, dried (Na$_2$SO$_4$), filtered and concentrated in vacuo. The resulting residue was purified by flash chromatography (diethyl ether) to afford 31A as mixture of SEM isomers. (oil, 1.92 g, 67%). $^1$H-NMR (400 MHz, CDCl$_3$, major isomer is given): δ 8.96 (d, J=2 Hz, 1H), 8.61 (dd, J=5 Hz, 2 Hz, 1H), 8.05 (dt, J=8 Hz, 2 Hz, 1H), 7.42-7.39 (m, 1H), 7.39 (s, 1H), 7.30-7.14 (m, 5H), 5.37 (s, 2H), 3.98 (t, J=7 Hz, 2H), 3.74-3.69 (m, 2H), 2.74 (t, J=7 Hz, 2H), 2.10-2.02 (m, 2H), 0.98-0.92 (m, 2H), 0.01 (s, 9H).

To a solution of anhydrous THF (50 ml) containing 31A (1.93 g, 4.71 mmol) was added 14.16 ml (3.0 eq) of TBAF (1.0 M in THF) under $N_2$. After the addition, the resulting solution was refluxed for 18 hours and subsequently concentrated in vacuo. Ethyl acetate was added and the organic layer was washed with a concentrated $NaHCO_3$ solution, dried ($Na_2SO_4$), filtered and concentrated in vacuo. The resulting residue was purified by flash chromatography (ethyl acetate) to afford the desired 3-[4-(3-phenyl-propoxy)-1H-pyrazol-3-yl]-pyridine (32A). (oil, 1.32 g, 73%). $^1$H-NMR (400 MHz, $CDCl_3$): δ 9.15 (d, J=2 Hz, 1H), 8.54 (dd, J=5 Hz, 2 Hz, 1H), 8.24 (dt, J=8 Hz, 2 Hz, 1H), 7.35-7.31 (m, 1H), 7.30-7.25 (m, 2H), 7.22-7.17 (m, 3H), 3.96 (t, J=7 Hz, 2H), 2.83 (t, J=7 Hz, 2H), 2.19-2.11 (m, 2H)

Compound 32A (0.3 g, 1.49 mmol) was converted to compound the title compound 3-[4-(3-phenyl-propoxy)-1H-pyrazol-3-yl]-1,2,5,6-tetrahydro-1-methylpyridine (33A), using the methodology described for the conversion of 21A to 22A (see Scheme 3).

Yield: 70% (amorphous, 72%). LCMS (method A); $R_t$: 1.52 min, ([M+H]$^+$=298). $^1$H-NMR (400 MHz, $CDCl_3$): δ 7.31-7.25 (m, 2H), 7.22-7.17 (m, 3H), 7.16-7.11 (bs, 1H), 6.62-6.44 (bs, 1H), 3.87 (t, J=7 Hz, 2H), 3.41-3.36 (m, 2H), 2.79 (t, J=7 Hz, 2H), 2.58 (t, J=7 Hz, 2H), 2.44 (s, 3H), 2.42-2.35 (m, 2H), 2.11-2.04 (m, 2H).

3-(4-Hexyloxy-1H-pyrazol-3-yl]-1,2,516-tetrahydro-1-methylpyridine (Compound 33B, Scheme 6)

Compound 29A/B was converted to 3-(4-iodo-1-(2-trimethylsilanyl-ethoxymethyl)-1H-pyrazol-3-yl)-1,2,5,6-tetrahydro-1-methylpyridine (compound 34A/B), using the methodology described for the conversion of 21A to 22A (see Scheme 3). Yield: 47%.(amorphous). LCMS (method A); $R_t$: 2.66 min, ([M+H]$^+$=420) and $R_t$: 2.74 min, ([M+H]$^+$=420).

A mixture of compound 34A/B (0.75 g, 1.79 mmol), CuI (34 mg, 0.179 mmol), $Cs_2CO_3$ (1.18 g, 3.58 mmol), 1,10-phenanthroline (0.07 g, 0.358 mmol) and 1-hexanol (5 ml, 40 mmol) was heated at 140° C. for 18 hours (under air).

The mixture was cooled to room temperature. Ethyl acetate was added and the organic layer was washed met a 5% $NaHCO_3$ solution, dried ($Na_2SO_4$), filtered and concentrated in vacuo. The resulting residue was purified by flash chromatography (ethyl acetate/PE 1:1) to afford compound 35A as an oil (0.24 g, 34%). LCMS (Method A); $R_t$: 2.50 min, ([M+H]$^+$=394).(TLC ethyl acetate/PE 1/1, $R_f$ 0.07).

To a solution of anhydrous THF (20 ml) containing a mixture of 35A (0.24 g, 0.6 mmol) was added 1.52 ml (2.5 eq) TBAF (1.0 M in THF) under $N_2$. After the addition, the resulting solution was refluxed for 18 hours and subsequently concentrated in vacuo. Ethyl acetate was added and the organic layer was washed with a concentrated $NaHCO_3$ solution, dried ($Na_2SO_4$), filtered and concentrated in vacuo. The resulting residue was purified by flash chromatography (ethyl acetate/MeOH (1/1)) to afford the title compound 33B. (oil, 0.12 g, 75%). LCMS (Method A); $R_t$: 1.99 min, ([M+H]$^+$=264).

Compound 33B was reacted with 1 equivalent of fumaric acid in EtOH and concentrated (amorphous). $^1$H-NMR (600 MHz, $D_6DMSO$): δ 7.50 (bs, 1H), 6.58 (s, 2H), 6.50 (bs, 1H), 3.88 (t, J=7 Hz, 2H), 3.75 (bs, 2H), 3.02 (bt, J=7 Hz, 2H), 2.69 (s, 3H), 2.48-2.42 (m, 2H), 1.75-1.67 (m, 2H), 1.45-1.38 (m, 2H), 1.36-1.28 (m, 4H), 0.89 (t, J=7 Hz, 3H).

3-(4-Butyloxyy-1H-pyrazol-3-yl)-pyridine (Compound 32C)

Compound 32C was prepared following the procedure as described for the synthesis of compound 32A (see Scheme 5) using 1-bromo-butane as the alkyl halogenide and 3-pyridin-3-yl-1-(2-trimethylsilanyl-1-ethoxymethyl)-1H-pyrazol-4-ol (30). Work-up and flash chromatography (ethyl acetate/diethyl ether 1/1) afforded compound 31C. Yield 30% (oil). $^1$H-NMR (major isomer is given, 400 MHz, $CDCl_3$): δ 8.9 (d, J=2 Hz, 1H), 8.6 (dd, J=5 Hz, 2 Hz, 1H), 8.05 (dt, J=8 Hz, 2 Hz, 1H), 7.42 (s, 1H), 7.41-7.37 (m, 1H), 5.37 (s, 2H), 3.98 (t, J=7 Hz, 2H), 3.74-3.68 (m, 2H), 1.74-1.66 (m, 2H), 1.49-1.39 (m, 2H), 0.92 (t, J=7 Hz, 3H), 0.02 (s, 9H).

The mixture of SEM-isomers was deprotected (TBAF/THF) to afford 3-(4-butyloxyy-1H-pyrazol-3-yl)-pyridine (32C).

Yield: 70% (amorphous). $^1$H-NMR (400 MHz, $CDCl_3$): δ 9.25 (d, J=2 Hz, 1H), 8.53 (dd, J=5 Hz, 2 Hz, 1H), 8.23 (dt, J=8 Hz, 2 Hz, 1H), 7.35-7.31 (m, 1H), 7.30 (s, 1H), 3.77 (t, J=7 Hz, 2H), 1.84-1.77 (m, 2H), 1.57-1.47 (m, 2H), 0.98 (t, J=7 Hz, 3H).

3-(4-Butyloxyy-1H-pyrazol-3-yl)-1,2,5,6-tetrahydro-1-methylpyridine (Compound 33C)

Compound 32C was converted to the title compound (33C), using the methodology described for the conversion of 21A to 22A (see Scheme 3).

Yield: 77% (amorphous). LCMS (method A); $R_t$: 1.48 min, ([M+H]$^+$=236). $^1$H-NMR (400 MHz, $CDCl_3$) δ 7.19 (bs, 1H), 6.52-6.42 (bs, 1H), 3.88 (t, J=7 Hz, 2H), 3.38-3.34 (m, 2H), 2.57 (t, J=7 Hz, 2H), 2.44 (s, 3H), 2.41-2.36 (m, 2H), 1.79-1.71 (m, 2H), 1.53-1.43 (m, 2H), 0.97 (t, J=7 Hz, 3H).

3-(4-But-3-enyloxy-1H-pyrazol-3-yl)-pyridine (Compound 32D)

Compound 32D was prepared following the procedure as described for the synthesis of compound 32A (see Scheme 5) using 4-bromo-but-1-ene as the alkyl halogenide and 3-pyridin-3-yl-1-(2-trimethylsilanyl-1-ethoxymethyl)-1H-pyrazol-4-ol (30). Work-up and flash chromatography (diethyl ether) afforded compound 31D. Yield 43% (oil, TLC diethyl ether $R_f$ 0.37), which was subsequently deprotected (TBAF/THF) to afford 3-(4-but-3-enyloxy-1H-pyrazol-3-yl)-pyridine (32D).

Yield: 75% (amorphous). $^1$H-NMR (400 MHz, $CDCl_3$): δ 9.15 (d, J=2 Hz, 1H), 8.58 (dd, J=5 Hz, 2 Hz, 1H), 8.24 (dt, J=8 Hz, 2 Hz, 1H), 7.35-7.30 (m, 1H), 7.32 (s, 1H), 5.96-5.85 (m, 1H), 5.22-5.11 (m, 2H), 4.02 (t, J=7 Hz, 2H), 2.62-2.55 (m, 2H).

3-(4-But-3-enyloxyy-1H-pyrazol-3-yl)-1,2,5,6-tetrahydro-1-methylpyridine (Compound 33D)

Compound 32D was converted to the title compound (33D), using the methodology described for the conversion of 21A to 22A (see Scheme 3).

Yield: 94%.(amorphous). LCMS (method A); $R_t$: 1.33 min, ([M+H]$^+$=234). $^1$H-NMR (400 MHz, $CDCl_3$): δ 7.20 (bs, 1H), 6.60-6.42 (bs, 1H), 5.94-5.83 (m, 1H), 5.19-5.07 (m, 2H), 3.94 (t, J=7 Hz, 2H), 3.38-3.33 (m, 2H), 2.59-2.50 (m, 4H), 2.44 (s, 3H), 2.41-2.36 (m, 2H).

3-(4-Heptyloxy-1H-pyrazol-3-yl)-1,2,5,6-tetrahydro-1-methylpyridine (Compound 33E)

A mixture of compound 34A/B (0.75 g, 1.79 mmol) (see Scheme 6), CuI (34 mg, 0.179 mmol), $Cs_2CO_3$ (1.18 g, 3.58 mmol), 1,10-phenanthroline (0.07 g, 0.358 mmol) and 1-heptanol (5 ml) was heated at 140° C. for 18 hours (under air). The mixture was cooled to room temperature. Ethyl acetate was added and the organic layer was washed with a 5% $NaHCO_3$ solution, dried ($Na_2SO_4$), filtered and concentrated in vacuo. The resulting residue was purified by flash chromatography (ethyl acetate/PE 1/1) to afford compound 35E (heptyl analogue of 35A, Scheme 6) as an oil (0.22 g, 30%). LCMS (method A); $R_t$: 2.60 min, ([M+H]$^+$=408).

To a solution of anhydrous THF (20 ml) containing a mixture of 35E (0.22 g, 0.54 mmol) was added 1.35 ml (2.5 eq) of TBAF (1.0 M in THF) under $N_2$. After the addition, the resulting solution was refluxed for 18 hours and subsequently concentrated in vacuo. Ethyl acetate was added and the organic layer was washed with a concentrated $NaHCO_3$ solution, dried ($Na_2SO_4$), filtered and concentrated in vacuo. The resulting residue was purified by flash chromatography (ethyl acetate/MeOH 1/1) to afford the title compound 33E. (oil, 0.08 g, 53%). LCMS (method A); $R_t$: 2.23 min, ([M+H]$^+$=278).

Compound 33E was reacted with 1 equivalent of fumaric acid in EtOH and concentrated (amorphous). $^1$H-NMR (600 MHz, D$_6$DMSO): δ 7.37 (bs, 1H), 6.58 (s, 2H), 6.43 (bs, 1H), 3.84 (t, J=7 Hz, 2H), 3.51 (bs, 2H), 2.77 (bt, J=7 Hz, 2H), 2.52 (s, 3H), 2.39-2.33 (m, 2H), 1.72-1.66 (m, 2H), 1.45-1.22 (m, 8H), 0.87 (t, J=7 Hz, 3H).

3-(4-Pent-4-enyloxy-1H-pyrazol-3-yl)-1,2,5,6-tetrahydro-1-methylpyridine (Compound 33F)

A mixture of compound 34A/B (0.75 g, 1.79 mmol) (see Scheme 6), CuI (34 mg, 0.179 mmol), $Cs_2CO_3$ (1.18 g, 3.58 mmol), 1,10-phenanthroline (0.07 g, 0.358 mmol) and pent-4-en-1-ol (5 ml) was heated at 140° C. for 18 hours (under air).

The mixture was cooled to room temperature. Ethyl acetate was added and the organic layer was washed met a 5% $NaHCO_3$ solution, dried ($Na_2SO_4$), filtered and concentrated in vacuo. The resulting residue was purified by flash chromatography (ethyl acetate/PE 1:1) to afford compound 35F (pent-4-enyl analogue of 35A, Scheme 6) as an oil (0.41 g, 60%). LCMS (Method A); $R_t$: 2.33 min, ([M+H]$^+$=378).

To a solution of anhydrous THF (20 ml) containing a mixture of 35F (0.22 g, 0.54 mmol) was added 1.35 ml (2.5 eq) of TBAF (1.0 M in THF) under $N_2$. After the addition, the resulting solution was refluxed for 18 hours, cooled and subsequently concentrated in vacuo. Ethyl acetate was added and the organic layer was washed with a concentrated $NaHCO_3$ solution, dried ($Na_2SO_4$), filtered and concentrated in vacuo. The resulting residue was purified by flash chromatography (ethyl acetate/MeOH 1/1) to afford the title compound 33F. (oil, 0.08 g, 53%). LCMS (Method A); $R_t$: 1.83 min, ([M+H]$^+$=248).

Compound 33F was reacted with 1 equivalent of fumaric acid in EtOH and concentrated (amorphous). $^1$H-NMR (600 MHz, D$_6$DMSO): δ 7.38 (bs, 1H), 6.56 (s, 2H), 6.48-6.44 (m, 1H), 5.88-5.80 (m, 1H), 5.06-4.95 (m, 2H), 3.86 (t, J=7 Hz, 2H), 3.60 (bs, 2H), 2.86 (bt, J=7 Hz, 2H), 2.58 (s, 3H), 2.42-2.37 (m, 2H), 2.20-2.15 (m, 2H), 1.83-1.77 (m, 2H).

3-(4-Pentyloxy-1H-pyrazol-3-yl)-1,2,5,6-tetrahydro-1-methylpyridine (Compound 33G, Scheme 6)

A mixture of compound 29A/B (1.0 g, 2.49 mmol) (see Scheme 5), CuI (0.05 g, 0.249 mmol), $Cs_2CO_3$ (1.62 g, 4.98 mmol), 1,10-phenanthroline (0.09 g, 0.498 mmol) and pentanol (7 ml) was heated at 140° C. for 18 hours (under air).

The mixture was cooled to room temperature. Ethyl acetate was added and the organic layer was washed met a 5% $NaHCO_3$ solution, dried ($Na_2SO_4$), filtered and concentrated in vacuo. The resulting residue was purified by flash chromatography (ethyl acetate/PE 1:2) to afford compound 31G as an oil (0.24 g, 27%). LCMS (method A); $R_t$: 2.76 min, ([M+H]$^+$=362). $^1$H-NMR (400 MHz, mixture of isomers, CDCl$_3$): δ 9.25 and 8.90 (d, J=2 Hz, 1H), 8.61 and 8.52 (dd, J=5 Hz, 2 Hz, 1H), 8.28 and 8.06 (dt, J=8 Hz, 2 Hz, 1H), 7.43 and 7.29 (s, 1H), 7.41-7.37 and 7.35-7.31 (m, 1H), 5.39 and 5.37 (s, 2H), 4.0-3.92 (m, 2H), 3.71 and 3.60 (bt, J=7 Hz, 2H), 1.88-1.80 and 1.76-1.69 (m, 2H), 1.52-1.25 (m, 6H), 0.97-0.90 (m, 3H).

To a solution of anhydrous THF (25 ml) containing 31G (0.23 g, 0.63 mmol) were added 1.59 ml (2.5 eq) of TBAF (1.0 M in THF) under $N_2$. After the addition, the resulting solution was refluxed for 18 hours and subsequently concentrated in vacuo. Ethyl acetate was added and the organic layer was washed with a concentrated $NaHCO_3$ solution, dried ($Na_2SO_4$), filtered and concentrated in vacuo. The resulting residue was purified by flash chromatography (ethyl acetate) to afford 3-(4-pentyloxy-1H-pyrazol-3-yl)-pyridine 32G. (oil, 0.14 g, 95%). LCMS (method A); $R_t$: 2.27 min, ([M+H]$^+$=232). $^1$H-NMR (400 MHz, CDCl$_3$): δ 9.25 (d, J=2 Hz, 1H), 8.53 (dd, J=5 Hz, 2 Hz, 1H), 8.23 (dt, J=8 Hz, 2 Hz, 1H), 7.36-7.29 (m, 2H), 3.96 (bt, J=7 Hz, 2H), 1.87-1.78 (m, 2H), 1.51-1.34 (m, 6H), 0.94 (t, J=7 Hz, 3H).

Compound 32G was converted to the title compound (33G), using the methodology described for the conversion of 21A to 22A (see Scheme 3).

Yield: 85% (amorphous). LCMS (Method A); $R_t$: 1.83 min, ([M+H]$^+$=250). $^1$H-NMR (400 MHz, CDCl$_3$): δ 7.19 (bs, 1H), 6.54-6.50 (bs, 1H), 3.88 (t, J=7 Hz, 2H), 3.40-3.36 (m, 2H), 2.59 (t, J=7 Hz, 2H), 2.45 (s, 3H), 2.43-2.37 (m, 2H), 1.81-1.75 (m, 2H), 1.46-1.34 (m, 4H), 0.93 (t, J=7 Hz, 3H).

Butyl-[3-(1-Methyl-1,2,5,6-tetrahydro-pyridin-3-yl)-1H-pyrazol-4-yl]-amine (Compound 42, Scheme 8)

To a solution of concentrated (10 ml) $H_2SO_4$ containing compound 19 (0.725 g, 5 mmol) was added a mixture of 5 ml $H_2SO_4$ and 5 ml $HNO_3$ dropwise at −10° C. under $N_2$. After the addition, the resulting solution was stirred for 3 hours at room temperature. The mixture was poured into ice followed by subsequent addition of 2 N NaOH. Ethyl acetate was added and the organic layer was washed with brine, dried ($Na_2SO_4$), filtered and concentrated in vacuo. The resulting residue was purified by flash chromatography (ethyl acetate) to give compound 38 as an oil (0.57 g, 60%). $^1$H-NMR (200 MHz, CDCl$_3$ and D$_6$DMSO 1/1): δ 8.9 (d, J=2 Hz, 1H), 8.7 (d, J=5 Hz, 2 Hz, 1H), 8.05 (dt, J=8 Hz, 2 Hz, 1H), 7.60 (s, 1H), 7.48-7.40 (m, 1H).

Compound 38 (0.37 g, 1.9 mmol) was dissolved in MeOH (containing Pd(OH)$_2$/C (0.03 g)). Hydrogenation was accomplished within 3 hours (1 atm) at room temperature. The reaction mixture was filtered, washed with ethyl acetate/MeOH (1/1) and concentrated in vacuo. The resulting residue was purified by flash chromatography (ethyl acetate followed by ethyl acetate/MeOH 1/1) to afford compound 39 as an oil (0.29 g, 95%). $^1$H-NMR (200 MHz, CDCl$_3$ and D$_6$DMSO 1/1): δ 9.05 (d, J=2 Hz, 1H), 8.51 (d, J=5 Hz, 2 Hz, 1H), 8.09 (dt, J=8 Hz, 2 Hz, 1H), 7.43 (s, 1H), 7.37-7.32 (m, 1H).

To a solution of anhydrous $CH_3CN$ (15 ml) containing a mixture of compound 39 (0.21 g, 1.3 mmol) and 0.27 ml (1.5 eq) of triethyl amine was added 0.14 ml of butyryl chloride under N$_2$. After the addition, the resulting solution was stirred for 3 hours at room temperature and subsequently concentrated in vacuo. Ethyl acetate was added and the organic layer was washed with a concentrated NaHCO$_3$ solution, dried (Na$_2$SO$_4$), filtered and concentrated in vacuo. The resulting residue was purified by flash chromatography (ethyl acetate) to afford N-(3-pyridin-3-yl-1H-pyrazol)-butyramide 40 (oil, 0.19 g, 77%).(TLC ethyl acetate R$_f$ 0.16).

Compound 40 was converted to compound 41, using the methodology described for the conversion of 21A to 22A (see Scheme 3).

Yield: 65% (amorphous). LCMS (Method A); R$_t$: 0.73 min, ([M+H]$^+$=249). $^1$H-NMR (600 MHz, CDCl$_3$): δ 8.4 (bs, 1H), 7.5 (bs, 1H), 6.0-5.96 (m, 1H), 3.27 (bs, 2H), 2.63 (t, J=7 Hz, 2H), 2.43 (s, 3H), 2.43-2.37 (m, 2H), 2.32 (t, J=7 Hz, 2H), 1.76-1.70 (m, 2H), 0.98 (t, J=7 Hz, 3H).

To a solution of anhydrous THF (25 ml) containing compound 41 (0.27 g, 1.09 mmol) was added 0.04 g (1.0 eq) LiAlH$_4$ under N$_2$. After the addition, the resulting solution was refluxed for 18 hours and allowed to warm to ambient temperature. To the reaction mixture was added 0.04 ml of H$_2$O, followed by 0.08 ml of 2N NaOH and 0.04 ml of H$_2$O. The resulting mixture was warmed for 10 minutes (60° C.), cooled to room temperature and filtrated. Ethyl acetate was added and the organic layer was washed with a concentrated NaHCO$_3$ solution, dried (Na$_2$SO$_4$), filtered and concentrated in vacuo. The resulting residue was purified by flash chromatography (ethyl acetate/MeOH 1/1) to afford the title compound 42. (oil, 0.21 g, 95%). LCMS (method A); R$_t$: 1.05 min, ([M+H]$^+$=235). $^1$H-NMR (600 MHz, CDCl$_3$): δ 7.1 (bs, 1H), 6.17-6.14 (m, 1H), 3.4-3.37 (m, 2H), 2.99 (t, J=7 Hz, 2H), 2.64 (t, J=7 Hz, 2H), 2.48 (s, 3H), 2.47-2.42 (m, 2H), 1.66-1.60 (m, 2H), 1.47-1.40 (m, 2H), 0.97 (t, J=7 Hz, 3H).

3-(4-Hex-1-ynyl-1H-pyrazol-3-yl)-pyridine (Compound 44A, Scheme 9)

Compound 20B (10.49 g, 38.6 mmol) was converted to 3-(1-phenylsulfonyl-4-iodo-1H-pyrazol-3-yl)-pyridine (36B), using the methodology described for the conversion of 20A to 36A (see Scheme 7). Yield 11.65 g (amorphous, 74%). (TLC diethyl ether R$_f$ 0.4) $^1$H-NMR (400 MHz, CDCl$_3$): δ 9.05 (d, J=2 Hz, 1H), 8.65 (dd, J=5 Hz, 2 Hz, 1H), 8.27 (s, 1H), 8.12 (dt, J=8 Hz, 2 Hz, 1H), 8.10-8.06 (m, 2H), 7.73-7.67 (m, 1H), 7.58 (bt, J=7 Hz, 2H), 7.39-7.34 (m, 1H).

To triethyl amine (10 ml) and DMF (4 ml) containing 36B (0.97 g, 2.36 mmol), was added 3 eq of hex-1-yne (0.81 ml). The resulting mixture was stirred for another 2 hours under N$_2$. Successively were added 10 mol % of CuI (45 mg), 5 mol % of PdCl$_2$(PPH$_3$)$_2$ (83 mg) and 18 mol % of PPH$_3$ (111 mg). After the addition, the resulting solution was warmed at 70° C. for 18 hours under N$_2$. After cooling to room temperature, the mixture was diluted with ethyl acetate, washed three times with a saturated NaHCO$_3$ solution, dried (Na$_2$SO$_4$), filtered and concentrated. The resulting residue was purified by flash chromatography (diethyl ether/PE (1/1)) to afford 3-(1-phenylsulfonyl-4-hex-1-ynyl-1H-pyrazol-3-yl)-pyridine (43A) as an oil (0.66 g, 77%). $^1$H-NMR (400 MHz, CDCl$_3$): δ 9.5-9.2 (bs, 1H), 8.8-8.4 (bs, 1H), 8.34 (bd, J=8 Hz, 1H), 8.21 (s, 1H), 8.08-8.04 (m, 2H), 7.67 (bt, J=7 Hz, 1H), 7.57 (bt, J=7 Hz, 2H), 7.41-7.32 (bs, 1H), 2.42 (t, J=7 Hz, 2H), 1.62-1.53 (m, 2H), 1.49-1.39 (m, 2H), 0.93 (t, J=7 Hz, 3H).

Compound 43A (0.66 g, 1.81 mmol), 1.3 g of KOH and 2 ml of NH$_2$NH$_2$.H$_2$O were combined in diethylene glycol (20 ml) and warmed to reflux for 1 hour under N$_2$. The mixture was cooled, concentrated and redissolved in MeOH. Filtration over 25 g of SCX-2 (MeOH followed by 1 N NH$_3$/MeOH) and subsequent purification by flash chromatography (ethyl acetate) afforded the title compound 44A. Yield 0.37 g (90%). $^1$H-NMR (400 MHz, CDCl$_3$): δ 9.25 (d, J=2 Hz, 1H), 8.60 (dd, J=5 Hz, 2 Hz, 1H), 8.34 (dt, J=8 Hz, 2 Hz, 1H), 7.73 (s, 1H), 7.39-7.34 (m, 1H), 2.43 ((t, J=7 Hz, 2H), 1.64-1.56 (m, 2H), 1.52-1.42 (m, 2H), 0.94 (t, J=7 Hz, 3H).

3-(4-Hex-1-ynyl-1H-pyrazol-3-yl)-1,2,5,6-tetrahydro-1-methylpyridine (Compound 45A, Scheme 9)

Compound 44A was converted to compound 45A, using the methodology described for the conversion of 21A to 22A (see Scheme 3). Yield: 90% (amorphous). LCMS (method A); R$_t$: 1.79 min, ([M+H]$^+$=244). $^1$H-NMR (400 MHz, CDCl$_3$): δ 7.57 (s, 1H), 6.78-6.66 (bs, 1H), 3.42-3.38 (m, 2H), 2.59 (bt, J=7 Hz, 2H), 2.45 (s, 3H), 2.44-2.37 (m, 2H), 1.62-1.43 (m, 4H), 0.94 (t, J=7 Hz, 3H).

3-(4-Hept-1-ynyl-1H-pyrazol-3-yl)-pyridine (Compound 44B)

Compound 44B was prepared following the procedure as described for the synthesis of compound 44A (see Scheme 9) using hept-1-yne and 3-(1-phenylsulfonyl-4-bromo-1H-pyrazol-3-yl)-pyridine (36A). (flash chromatography with diethyl ether) to afford 3-(1-phenylsulfonyl-4-hept-1-ynyl-1H-pyrazol-3-yl)-pyridine (43B) as an oil (90%). $^1$H-NMR (400 MHz, CDCl$_3$): δ 9.25 (bs, 1H), 8.6 (bs, 1H), 8.34 (bd, J=8 Hz, 1H), 8.21 (s, 1H), 8.06 (bd, J=8 Hz, 2H), 7.67 (bt, J=7 Hz, 1H), 7.57 (bt, J=7 Hz, 2H), 7.36-7.30 (m, 1H), 2.42 (t, J=7 Hz, 2H), 1.63-1.55 (m, 2H), 1.44-1.28 (m, 4H), 0.89 (t, J=7 Hz, 3H). Compound 43B was converted to the title compound 44B, using the methodology described for the conversion of 43A to 44A (see Scheme 9). Yield: 98% (oil). $^1$H-NMR (400 MHz, CDCl$_3$): δ 9.25 (d, J=2 Hz, 1H), 8.59 (dd, J=5 Hz, 2 Hz, 1H), 8.37 (dt, J=8 Hz, 2 Hz, 1H), 7.72 (s, 1H), 7.38-7.33 (m, 1H), 2.42 ((t, J=7 Hz, 2H), 1.65-1.57 (m, 2H), 1.46-1.30 (m, 4H), 0.90 (t, J=7 Hz, 3H).

3-(4-Hept-1-ynyl-1H-pyrazol-3-yl)-1,2,5,6-tetrahydro-1-methylpyridine (Compound 45B)

Compound 44B was converted to compound 45B, using the methodology described for the conversion of 21A to 22A (see Scheme 3). Yield: 44% (amorphous). LCMS (method A); R$_t$: 1.84 min, ([M+H]$^+$=258). $^1$H-NMR (400 MHz, CDCl$_3$): δ 7.57 (s, 1H), 6.78-6.66 (bs, 1H), 3.42-3.38 (m, 2H), 2.59 (bt, J=7 Hz, 2H), 2.45 (s, 3H), 2.44-2.37 (m, 2H), 1.62-1.43 (m, 4H), 0.94 (t, J=7 Hz, 3H).

3-(4-Non-1-ynyl-1H-pyrazol-3-yl)-pyridine (Compound 44C)

Compound 44C was prepared following the procedure as described for the synthesis of compound 44A (see Scheme 9) using non-1-yne and 3-(1-phenylsulfonyl-4-iodo-1H-pyrazol-3-yl)-pyridine (36B). (flash chromatography with diethyl ether/PE 1/1) to afford 3-(1-phenylsulfonyl-4-non-1-ynyl-1H-pyrazol-3-yl)-pyridine (43C) as an oil (80%). (TLC diethyl ether R$_f$ 0.44).

Compound 43C was converted to the title compound 44C, using the methodology described for the conversion of 43A to 44A (see Scheme 9). Yield: 78% (oil). $^1$H-NMR (400 MHz, CDCl$_3$): δ 9.25 (d, J=2 Hz, 1H), 8.61 (dd, J=5 Hz, 2 Hz, 1H), 8.35 (dt, J=8 Hz, 2 Hz, 1H), 7.73 (s, 1H), 7.39-7.34 (m, 1H), 2.42 ((t, J=7 Hz, 2H), 1.65-1.56 (m, 2H), 1.47-1.38 (m, 2H), 1.37-1.22 (m, 6H), 0.90 (t, J=7 Hz, 3H).

3-(4-Non-1-ynyl-1H-pyrazol-3-yl)-1,2,5,6-tetrahydro-1-methylpyridine (Compound 45C)

Compound 44C was converted to compound 45C, using the methodology described for the conversion of 21A to 22A (see Scheme 3). Yield: 79% (amorphous). LCMS (method A); $R_t$: 2.17 min, ([M+H]$^+$=286). $^1$H-NMR (400 MHz, CDCl$_3$): δ 7.57 (s, 1H), 6.74-6.69 (bs, 1H), 3.40-3.36 (m, 2H), 2.58 (bt, J=7 Hz, 2H), 2.44 (s, 3H), 2.43-2.36 (m, 2H), 1.63-1.55 (m, 2H), 1.48-1.39 (m, 2H), 1.36-1.23 (m, 6H), 0.89 (t, J=7 Hz, 3H).

3-[4-(5-Phenyl-pent-1-ynyl)-1H-pyrazol-3-yl]-pyridine (Compound 44D)

Compound 44C was prepared following the procedure as described for the synthesis of compound 44A (see Scheme 9) using pent-4-ynyl-benzene and 3-(1-phenylsulfonyl-4-iodo-1H-pyrazol-3-yl)-pyridine (36B). (flash chromatography with diethyl ether/PE (1/1)) to afford 3-[1-phenylsulfonyl-4-(5-phenyl-pent-1-ynyl)-1H-pyrazol-3-yl]-pyridine (43D) as an oil (80%). $^1$H-NMR (400 MHz, CDCl$_3$): δ 9.3 (d, J=2 Hz, 1H), 8.6 (dd, J=5 Hz, 2 Hz, 1H), 8.33 (dt, J=8 Hz, 2 Hz, 1H), 8.22 (s, 1H), 8.09-8.05 (m, 2H), 7.68 (bt, J=8 Hz, 1H), 7.57 (bt, J=8 Hz, 2H), 7.35-7.25 (m, 3H), 7.21-7.15 (m, 3H), 2.74 ((t, J=7 Hz, 2H), 2.42 ((t, J=7 Hz, 2H), 1.96-1.87 (m, 2H). (TLC diethyl ether $R_f$ 0.56).

Compound 43D was converted to the title compound 44D, using the methodology described for the conversion of 43A to 44A (see Scheme 9). Yield: 86% (oil). $^1$H-NMR (400 MHz, CDCl$_3$): δ 9.25 (d, J=2 Hz, 1H), 8.6 (dd, J=5 Hz, 2 Hz, 1H), 8.35 (dt, J=8 Hz, 2 Hz, 1H), 7.74 (s, 1H), 7.40-7.17 (m, 6H), 2.77 ((t, J=7 Hz, 2H), 2.44 ((t, J=7 Hz, 2H), 1.99-1.89 (m, 2H).

3-[4-(5-Phenyl-pent-1-ynyl)-1H-pyrazol-3-yl]-1,2,5,6-tetrahydro-1-methylpyridine (Compound 45D)

Compound 44D was converted to compound 45D, using the methodology described for the conversion of 21A to 22A (see Scheme 3). Yield: 95% (amorphous). LCMS (method A); $R_t$: 1.99 min, ([M+H]$^+$=306). $^1$H-NMR (400 MHz, CDCl$_3$): δ 7.58 (s, 1H), 7.31-7.18 (m, 5H), 6.79-6.73 (bs, 1H), 3.43-3.40 (m, 2H), 2.78 (t, J=7 Hz, 2H), 2.60 (bt, J=7 Hz, 2H), 2.45-2.37 (m, 7H), 1.95-1.87 (m, 2H).

3-[4-(5-Cyclohexyl-pent-1-ynyl)-1H-pyrazol-3-yl]-pyridine (Compound 44E)

Compound 44E was prepared following the procedure as described for the synthesis of compound 44A (see Scheme 9) using pent-4-ynyl-cyclohexane and 3-(1-phenylsulfonyl-4-iodo-1H-pyrazol-3-yl)-pyridine (36B). (flash chromatography with diethyl ether/PE 1/1) to afford 3-[1-phenylsulfonyl-4-(5-cyclohexyl-pent-1-ynyl)-1H-pyrazol-3-yl]-pyridine (43E) as an oil (90%). $^1$H-NMR (400 MHz, CDCl$_3$) δ 9.25 (d, J=2 Hz, 1H), 8.6 (dd, J=5 Hz, 2 Hz, 1H), 8.33 (dt, J=8 Hz, 2 Hz, 1H), 8.21 (s, 1H), 8.08-8.04 (m, 2H), 7.68 (bt, J=8 Hz, 1H), 7.57 (bt, J=8 Hz, 2H), 7.35-7.31 (m, 1H), 2.38 (t, J=7 Hz, 2H), 1.72-1.55 (m, 6H), 1.31-1.10 (m, 7H), 0.95-0.8 (m, 2H).

Compound 43E was converted to the title compound 44E, using the methodology described for the conversion of 43A to 44A (see Scheme 9). Yield: 94% (oil). $^1$H-NMR (400 MHz, CDCl$_3$): δ 9.25 (d, J=2 Hz, 1H), 8.6 (dd, J=5 Hz, 2 Hz, 1H), 8.35 (dt, J=8 Hz, 2 Hz, 1H), 7.72 (s, 1H), 7.39-7.34 (m, 1H), 2.40 (t, J=7 Hz, 2H), 1.73-1.57 (m, 6H), 1.35-1.10 (m, 7H), 0.93-0.75 (m, 2H).

3-[4-(5-Cyclohexyl-pent-1-ynyl)-1H-pyrazol-3-yl]-1,2,5,6-tetrahydro-1-methylpyridine (Compound 45E)

Compound 44E was converted to compound 45E, using the methodology described for the conversion of 21A to 22A (see Scheme 3). Yield: 90% (amorphous). LCMS (method A); $R_t$ 2.28 min, ([M+H]$^+$=312). $^1$H-NMR (400 MHz, CDCl$_3$): δ 7.57 (s, 1H), 6.76-6.71 (bs, 1H), 3.41-3.37 (m, 2H), 2.59 (bt, J=7 Hz, 2H), 2.45-2.35 (m, 7H), 1.75-1.55 (m, 6H), 1.35-1.10 (m, 7H), 0.94-0.8 (m, 2H).

3-(4-Hex-1-enyl-1H-pyrazol-3-yl)-1,2,5,6-tetrahydro-1-methylpyridine (Compound 47A, Scheme 9)

To toluene (20 ml) containing 36A (0.67 g, 1.84 mmol) (see Scheme 7), was added 1.5 eq of (E)-hexene-1-ylboronic acid (0.35 g). The resulting mixture was stirred for 2 hours under N$_2$. Successively were added 2 eq of K$_3$PO$_4$ (0.78 g), 4 mol % of Pd(OAc)$_2$ (16.5 mg) and 8 mol % of S-Phos (60.4 mg). After the addition, the resulting solution was warmed at 90° C. for 18 hours under N$_2$. After cooling to room temperature, the mixture was diluted with ethyl acetate, washed three times with a saturated NaHCO$_3$ solution, dried (Na$_2$SO$_4$), filtered and concentrated. The resulting residue was purified by flash chromatography (diethyl ether/PE 1/1) to afford 3-(1-phenylsulfonyl-4-hex-1-enyl-1H-pyrazol-3-yl)-pyridine (46A) as an oil (0.38 g, 61%). $^1$H-NMR (400 MHz, CDCl$_3$): δ 8.8 (d, J=2 Hz, 1H), 8.6 (dd, J=5 Hz, 2 Hz, 1H), 8.15 (s, 1H), 8.10-8.05 (m, 2H), 7.94 (dt, J=8 Hz, 2 Hz, 1H), 7.70-7.64 (m, 1H), 7.56 (bt, J=8 Hz, 2H), 7.37-7.33 (m, 1H), 6.19-6.02 (m, 1H), 2.2-2.13 (m, 2H), 1.45-1.29 (m, 4H), 0.90 (t, J=7 Hz, 3H).

Compound 46A (0.34 g, 0.97 mmol), 0.7 g of KOH and 1 ml of NH$_2$NH$_2$.H$_2$O were combined in diethylene glycol (10 ml) and warmed to reflux for 1 hour under N$_2$. The mixture was cooled, concentrated and redissolved in MeOH. Filtration over 25 g of SCX-2 (MeOH followed by 1 N NH$_3$/MeOH) and subsequent purification by flash chromatography (ethyl acetate) afforded 3-(4-hex-1-enyl-1H-pyrazol-3-yl)-pyridine (the deprotected analog of 46A). Yield 0.18 g (86%). (TLC diethyl ether $R_f$ 0.18). 3-(4-Hex-1-enyl-1H-pyrazol-3-yl)-pyridine was converted to the title compound 47A, using the methodology described for the conversion of 21 A to 22A (see Scheme 3). Yield: 50% (amorphous). LCMS (method A); $R_t$: 2.30 min, ([M+H]$^+$=246). $^1$H-NMR (400 MHz, CDCl$_3$): δ 7.59 (s, 1H), 6.22 (bd, J=16 Hz, 1H), 6.03-5.98 (bs, 1H), 5.98-5.88 (m, 1H), 3.26-3.21 (m, 2H), 2.63 (bt, J=7 Hz, 2H), 2.44 (s, 3H), 2.43-2.36 (m, 2H), 2.19-2.11 (m, 2H), 1.46-1.29 (m, 4H), 0.91 (t, J=7 Hz, 3H).

3-{4-2-[-(3-Fluor-phenyl)-vinyl]-1H-pyrazol-3-yl}-1,2,5,6-tetrahydro-1-methylpyridine (Compound 47B)

To toluene (20 ml) containing 36A (0.48 g, 1.32 mmol) (see Scheme 7), was added 1.5 eq of (E)-2-(3-fluorphenyl)-vinyl boronic acid (0.33 g). The resulting mixture was stirred for 2 hours under N$_2$. Successively were added 2 eq of K$_3$PO$_4$ (0.56 g), 4 mol % of Pd(OAc)$_2$ (8.8 mg) and 8 mol % of S-Phos (32 mg). After the addition, the resulting solution was warmed at 90° C. for 18 hours under N$_2$. After cooling to room temperature, the mixture was diluted with ethyl acetate, washed three times with a saturated NaHCO$_3$ solution, dried (Na$_2$SO$_4$), filtered and concentrated. The resulting residue was purified by flash chromatography (diethyl ether/PE 1/1) to afford 3-(1-phenylsulfonyl-4-[2-(3-fluoro-phenyl)-vinyl]-1H-pyrazol-3-yl)-pyridine (46B) as an oil (0.39 g, 73%). $^1$H-NMR (400 MHz, CDCl$_3$): δ 8.85 (d, J=2 Hz, 1H), 8.65 (dd, J=5 Hz, 2 Hz, 1H), 8.36 (s, 1H), 8.13-8.08 (m, 2H), 7.95 (dt, J=8 Hz, 2 Hz, 1H), 7.72-7.67 (m, 1H), 7.58 (bt, J=8 Hz, 2H), 7.41-7.37 (m, 1H), 7.33-7.27 (m, 1H), 7.16 (bd, J=7 Hz, 1H), 7.12-7.07 (m, 1H), 7.0-6.94 (m, 1H), 6.92 (d, J=16 Hz, 1H), 6.82 (d, J=16 Hz, 1H).

Compound 46B (1.06 g, 2.62 mmol), 1.3 g of KOH and 2 ml NH$_2$NH$_2$.H$_2$O were combined in diethylene glycol (25 ml) and warmed to reflux for 1 hour under N$_2$. The mixture was cooled, concentrated and redissolved in MeOH. Filtration over 25 g of SCX-2 (MeOH followed by 1 N NH$_3$/MeOH) and subsequent purification by flash chromatography (ethyl acetate) afforded 3-{4-[2-(3-fluor-phenyl)-vinyl]-1H-pyrazol-3-yl}-pyridine (the deprotected analog of 46B). Yield 0.42 g (60.4%). $^1$H-NMR (400 MHz, CDCl$_3$): δ 8.85 (d, J=2 Hz, 1H), 8.65 (dd, J=5 Hz, 2 Hz, 1H), 7.95-7.90 (m, 2H), 7.45-7.41 (m, 1H), 7.32-7.27 (m, 1H), 7.20-7.16 (m, 1H), 7.14-7.09 (m, 1H), 6.99 (d, J=16 Hz, 1H), 6.96-6.86 (m, 2H).

3-{4-[2-(3-Fluor-phenyl)-vinyl]-1H-pyrazol-3-yl}-pyridine was converted to the title compound 47B, using the methodology described for the conversion of 21A to 22A (see Scheme 3). Yield: 67% (amorphous). LCMS (method A); R$_t$: 1.79 min, ([M+H]$^+$=284). $^1$H-NMR (400 MHz, CDCl$_3$): δ 7.78 (s, 1H), 7.31-7.25 (m, 1H), 7.20-7.10 (m, 2H), 7.0-6.88 (m, 2H), 6.81 (d, J=16 Hz, 1H), 6.07-6.01 (m, 1H), 3.33-3.25 (m, 2H), 2.69 (bt, J=7 Hz, 2H), 2.50-2.42 (m, 5H).

3-(4 Oct-1-enyl-1H-pyrazol-3-yl)-1,2,5,6-tetrahydro-1-methylpyridine (Compound 47C)

To toluene (20 ml) containing 36A (0.91 g, 2.5 mmol) (see Scheme 7), was added 1.5 eq (E)-octene-1-ylboronic acid (0.59 g). The resulting mixture was stirred for 2 hours under N$_2$. Successively were added 2 eq of K$_3$PO$_4$ (1.06 g), 4 mol % of Pd(OAc)$_2$ (22.4 mg) and 8 mol % of S-Phos (82 mg). After the addition, the resulting solution was warmed at 90° C. for 18 hours under N$_2$. After cooling to room temperature, the mixture was diluted with ethyl acetate, washed three times with a saturated NaHCO$_3$ solution, dried (Na$_2$SO$_4$), filtered and concentrated. The resulting residue was purified by flash chromatography (diethyl ether/PE 1/1) to afford 3-(1-phenyl-sulfonyl-4-oct-1-enyl-1H-pyrazol-3-yl)-pyridine (46C) as an oil (0.31 g, 32%). $^1$H-NMR (400 MHz, CDCl$_3$): δ 8.85 (d, J=2 Hz, 1H), 8.65 (dd, J=5 Hz, 2 Hz, 1H), 8.15 (s, 1H), 8.08-8.05 (m, 2H), 7.93 (dt, J=8 Hz, 2 Hz, 1H), 7.69-7.64 (m, 1H), 7.59-7.52 (m, 2H), 7.37-7.33 (m, 1H), 6.19 (d, J=16 Hz, 1H), 6.10-6.03 (m, 1H), 2.19-2.12 (m, 2H), 1.45-1.37 (m, 2H), 1.36-1.23 (m, 6H), 0.90 (t, J=7 Hz, 3H).

Compound 46C (0.35 g, 0.89 mmol), 0.7 g of KOH and 1 ml of NH$_2$NH$_2$.H$_2$O were combined in diethylene glycol (10 ml) and warmed to reflux for 1 hour under N$_2$. The mixture was cooled, concentrated and re-dissolved in MeOH. Filtration over 25 g of SCX-2 (MeOH followed by 1 N NH$_3$/MeOH) and subsequent purification by flash chromatography (ethyl acetate) afforded 3-(4-oct-1-enyl-1H-pyrazol-3-yl)-pyridine (the deprotected analog of 46C). Yield 0.19 g (95%). $^1$H-NMR (400 MHz, CDCl$_3$): δ 8.85 (d, J=2 Hz, 1H), 8.65 (dd, J=5 Hz, 2 Hz, 1H), 7.91 (dt, J=8 Hz, 2 Hz, 1H), 7.71 (s, 1H), 7.41-7.36 (m, 1H), 6.27 (d, J=16 Hz, 1H), 6.07-5.98 (m, 1H), 2.19-2.12 (m, 2H), 1.46-1.38 (m, 2H), 1.37-1.23 (m, 6H), 0.89 (t, J=7 Hz, 3H).

3-(4 Oct-1-enyl-1H-pyrazol-3-yl)-pyridine was converted to the title compound 47C, using the methodology described for the conversion of 21A to 22A (see Scheme 3). Yield: 95% (amorphous). $^1$H-NMR (400 MHz, CDCl$_3$): δ 7.58 (s, 1H), 6.24 (bd, J=16 Hz, 1H), 6.07-6.02 (m, 1H), 5.98-5.89 (m, 1H), 3.29-3.25 (m, 2H), 2.63 (bt, J=7 Hz, 2H), 2.46 (s, 3H), 2.44-2.38 (m, 2H), 2.18-2.12 (m, 2H), 1.46-1.38 (m, 2H), 1.38-1.24 (m, 6H), 0.91 (t, J=7 Hz, 3H).

3-(4-Butylsulfanyl-1H-pyrazol-3-yl)-1-azabicyclo[2.2.2]octane (Compound 49A, Scheme 10)

To a solution of anhydrous THF (150 ml) containing compound 48 (0.5 g, 1.65 mmol), prepared according to Biorganic & Medicinal Chemistry, 8, 2000, 449-454, were added 2.1 eq of n-BuLi (1.39 ml, 2.5 M in hexane) dropwise at −78° C. under N$_2$. After the addition, the resulting solution was stirred for 1.5 hours at −78° C. At this temperature 1.1 eq of ethyldisulfanylethane (0.35 ml) were added and the resulting solution was stirred for 1 hour at −78° C. and subsequently allowed to warm to ambient temperature overnight. Then the mixture was quenched with a saturated NH$_4$Cl solution at 0° C. and concentrated in vacuo. Ethyl acetate was added and the organic layer was washed with 2 N NaOH, dried (Na$_2$SO$_4$), filtered and concentrated in vacuo. Purification by flash chromatography (MeOH) afforded the title compound 49A (amorphous, 0.15 g, 35%). Compound 49A was reacted with 1 equivalent of fumaric acid in EtOH and concentrated. (solid). mp 162-164° C. LCMS (method A); R$_t$: 1.62 min, ([M+H]$^+$=266). $^1$H-NMR (400 MHz, D$_6$DMSO): δ 7.83 (s, 1H), 6.43 (s, 2H), 3.60-3.39 (m, 3H), 3.25-3.00 (m, 4H), 2.58 (bt, J=7 Hz, 2H), 2.10-2.05 (m, 1H), 1.98-1.83 (m, 2H), 1.78-1.68 (m, 1H), 1.48-1.30 (m, 4H), 0.84 (t, J=7 Hz, 3H).

3-(4-Pentylsulfanyl-1H-pyrazol-3-yl)-1-azabicyclo[2.2.2]octane (Compound 49B, Scheme 10)

Compound 48 (2.50 g; 8.25 mmol), K$_2$CO$_3$ (1.82 g; 13.2 mmol) and pentane-1-thiol (1.53 ml, 12.4 mmol) were dissolved in 30 ml of DMF and the solution was degassed for 45 minutes with argon. To this solution were added Pd$_2$(dba)$_3$ (755 mg; 0.83 mmol) and Xantphos (953 mg; 1.65 mmol). After the addition, the reaction mixture was heated up to 120° C. and stirred for 20 hours under N$_2$. The mixture was cooled, concentrated and re-dissolved in MeOH. Filtration over 25 g of SCX-2 (MeOH followed by 1 N NH$_3$/MeOH) and subsequent purification by flash chromatography (EtOH) afforded the title compound 49B as an oil. Yield 395 mg (17%). Compound 49B was reacted with 1 equivalent of fumaric acid in EtOH and concentrated (solid). mp 142-145° C. $^1$H-NMR (600 MHz, D$_6$DMSO): δ 7.83 (s, 1H), 6.48 (s, 2H), 3.58-3.51 (m, 1H), 3.48-3.41 (m, 2H), 3.25-3.15 (m, 3H), 3.11-3.03 (m, 1H), 2.61-2.53 (m, 2H), 2.11-2.06 (m, 1H), 1.97-1.85 (m, 2H), 1.77-1.69 (m, 1H), 1.59-1.52 (m, 1H), 1.48-1.41 (m, 2H), 1.34-1.22 (m, 4H), 0.83 (t, J=7 Hz, 3H).

3-(4-Methylsulfanyl-1H-pyrazol-3-yl)-1-azabicyclo[2.2.2]octane (Compound 49C)

Compound 48 (2.50 g; 8.25 mmol)(see Scheme 10) was dissolved in 30 ml of DMF and the solution was degassed for 45 minutes with argon. To this solution were added NaSMe (867 mg, 12.4 mmol), Pd$_2$(dba)$_3$ (755 mg; 0.83 mmol) and Xantphos (953 mg; 1.65 mmol). After the addition, the reaction mixture was heated to 120° C. and stirred for 20 hours under N$_2$. The mixture was cooled, concentrated and re-dissolved in MeOH. Filtration over 25 g of SCX-2 (MeOH followed by 1 N NH$_3$/MeOH) and subsequent purification by flash chromatography (EtOH) afforded compound 49C (oil).

Crystallization from diethyl ether gave the title compound (solid).mp 145-147° C. Yield: 290 mg (16%). $^1$H-NMR (600 MHz, D$_6$DMSO): δ7.70 (s, 1H), 3.21-3.12 (m, 1H), 3.10-3.01 (m, 2H), 2.92-2.85 (m, 1H), 2.81-2.73 (m, 2H), 2.68-2.61 (m, 1H), 2.21 (s, 3H), 1.81-1.78 (m, 1H), 1.68-1.55 (m, 3H), 1.25-1.18 (m, 1H).

3-(4-Ethylsulfanyl-1H-pyrazol-3-yl)-1-azabicyclo [2.2.2]octane (Compound 49D)

Compound 49D was prepared following the procedure as described for the synthesis of compound 49B (see Scheme 10) using ethanethiol as reagent. Subsequent purification by flash chromatography (EtOH to EtOH/triethylamine 99/1) afforded compound 49D.

Yield: 30% (oil). $^1$H-NMR (600 MHz, D$_6$DMSO): δ 7.69 (s, 1H), 3.16-2.99 (m, 3H), 2.92-2.84 (m, 1H), 2.80-2.71 (m, 2H), 2.67-2.60 (m, 1H), 2.56-2.51 (m, 2H), 1.78-1.75 (m, 1H), 1.66-1.54 (m, 3H), 1.25-1.18 (m, 1H), 1.08 (t, J=7 Hz, 3H).

3-(4-Propylsulfanyl-1H-pyrazol-3-yl)-1-azabicyclo [2.2.2]octane (Compound 49E)

Compound 49E was prepared following the procedure as described for the synthesis of compound 49B (see Scheme 10) using propane-1-thiol as reagent. Subsequent purification by flash chromatography (EtOH to EtOH/triethylamine 99/1) afforded compound 49E.

Yield: 25% (amorphous). $^1$H-NMR (600 MHz, D$_6$DMSO): δ 7.72-7.64 (bs, 1H), 3.16-2.99 (m, 3H), 2.93-2.84 (m, 1H), 2.80-2.71 (m, 2H), 2.67-2.60 (m, 1H), 2.54-2.48 (m, 2H+DMSO), 1.78-1.75 (m, 1H), 1.66-1.54 (m, 3H), 1.47-1.40 (m, 2H), 1.25-1.18 (m, 1H), 0.90 (t, J=7 Hz, 3H).

3-(4-Hexylsulfanyl-1H-pyrazol-3-yl)-1-azabicyclo [2.2.2]octane (Compound 49F)

Compound 49F was prepared following the procedure as described for the synthesis of compound 49B (see Scheme 10) using hexane-1-thiol as reagent. Subsequent purification by flash chromatography (EtOH) afforded compound 49F.

Yield: 25% (oil). Compound 49F was reacted with 1 equivalent of fumaric acid in EtOH and concentrated (solid). mp 130° C. $^1$H-NMR (600 MHz, D$_6$DMSO): δ 7.81 (s, 1H), 6.46 (s, 2H), 3.55-3.49 (m, 1H), 3.45-3.39 (m, 2H), 3.22-3.13 (m, 3H), 3.08-3.02 (m, 1H), 2.60-2.52 (m, 2H), 2.09-2.05 (m, 1H), 1.95-1.83 (m, 2H), 1.75-1.68 (m, 1H), 1.57-1.51 (m, 1H), 1.46-1.40 (m, 2H), 1.35-1.29 (m, 2H), 1.27-1.17 (m, 4H), 0.83 (t, J=7 Hz, 3H).

3-(4-Phenethylsulfanyl-1H-pyrazol-3-yl)-1-azabicyclo[2.2.2]octane (Compound 49G)

Compound 49G was prepared following the procedure as described for the synthesis of compound 49B (see Scheme 10) using 3-phenyl-1-propanethiol as reagent. Subsequent purification by flash chromatography (EtOH) afforded compound 49G.

Yield: 11% (oil). Compound 49G was reacted with 1 equivalent of fumaric acid in EtOH and concentrated (amorphous). $^1$H-NMR (600 MHz, D$_6$DMSO): δ 7.86 (s, 1H), 7.26 (t, J=8 Hz, 2H), 7.19-7.14 (m, 3H), 6.49 (s, 2H), 3.56-3.50 (m, 1H), 3.46-3.39 (m, 2H), 3.24-3.14 (m, 3H), 3.10-3.03 (m, 1H), 2.66 (t, J=7 Hz, 2H), 2.60-2.53 (m, 2H), 2.03-2.00 (bs, 1H), 1.94-1.82 (m, 2H), 1.77-1.68 (m, 3H), 1.56-1.50 (m, 1H).

3-[4-(3-Methyl-butylsulfanyl)-1H-pyrazol-3-yl]-1-azabicyclo[2.2.2]octane (Compound 49H)

Compound 49H was prepared following the procedure as described for the synthesis of compound 49B (see Scheme 10) using 3-methyl-1-butanethiol as reagent. Subsequent purification by flash chromatography (EtOH) afforded compound 49G.

Yield: 20% (oil). Compound 49G was reacted with 1 equivalent of fumaric acid in EtOH and concentrated (solid). mp 157-159° C. $^1$H-NMR (600 MHz, D$_6$DMSO): δ 7.83 (s, 1H), 6.47 (s, 2H), 3.56-3.50 (m, 1H), 3.46-3.40 (m, 2H), 3.24-3.15 (m, 3H), 3.09-3.03 (m, 1H), 2.58 (t, J=7 Hz, 2H), 2.09-2.06 (bs, 1H), 1.96-1.84 (m, 2H), 1.76-1.68 (m, 1H), 1.67-1.59 (m, 1H), 1.58-1.52 (m, 1H), 1.38-1.30 (m, 2H), 0.83 (d, J=7 Hz, 6H).

3-[4-(4,4-Difluoro-but-3-enylsulfanyl)-1H-pyrazol-3-yl]-1-azabicyclo[2.2.2]octane (Compound 49I)

Compound 49I was prepared following the procedure as described for the synthesis of compound 21A (see Scheme 3) using 3-phenyl-propyldisulfanyl-3-propylbenzene as the disulfide (prepared according to the methodology described in Tetrahedron Letters, 42, 2001, 6741-6743) and 3-(4-iodo-1H-pyrazol-3-yl]-1-azabicyclo[2.2.2]octane (compound 48, see Scheme 10). Purification conditions were: PrepHPLC (system CHSLCPO$_2$), Column: Inertsil ODS-3, 8 um. Eluens 10%/90% CH$_3$CN/H$_2$O+HCOOH, 50 ml/min. LCMS (method A): R$_t$: 1.16 min, ([M+H]$^+$=300). Yield: 4.5%. (oil). $^1$H-NMR (600 MHz, CDCl$_3$): δ 7.63 (s, 1H), 4.24 and 4.17 (ddt, J=7 Hz, 26 Hz, 3 Hz, 1H), 3.91-3.84 (m, 1H), 3.51-3.37 (m, 3H), 3.32-3.19 (m, 2H), 3.12-3.03 (m, 1H), 2.57 (t, J=7 Hz, 2H), 2.23-2.15 (m, 3H), 2.12-2.01 (m, 1H), 2.01-1.89 (m, 2H), 1.61-1.51 (m, 1H).

3-(4-Butoxy-1H-pyrazol-3-yl)-1-azabicyclo[2.2.2] octane (Compound 52A, Scheme 10)

A 60% dispersion of NaH in mineral oil (1.5 g, 38 mmol) was added to a solution of anhydrous THF (300 ml) containing 3-(4-iodo-1H-pyrazol-3-yl]-1-azabicyclo[2.2.2]octane (compound 48, 9.6 g, 31.7 mmol) under N$_2$. The resulting mixture was stirred for 2 hours at room temperature until all solids had dissolved. The reaction mixture was subsequently treated with 38.4 mmol (6.74 ml) of 2-chloromethoxy-ethyl-trimethylsilane (SEM-Cl). The resulting mixture was stirred for 20 hours at room temperature. Because of partial quaternization of the desired product (50), TBAF (1 M solution in THF, 45 ml, 45 mmol) was added and the mixture was stirred for 20 hours at room temperature. Ethyl acetate was added to the mixture and the organic layer was washed with a 2 N NaOH solution followed by brine, dried (Na$_2$SO$_4$), filtered and concentrated to afford 3-[4-iodo-1-(2-trimethylsilanyl-ethoxymethyl)-1H-pyrazol-3-yl]-1-azabicyclo[2.2.2]octane (50). Yield: 11.6 g, 26.7 mmol, 84%. LCMS (method B); R$_t$: 3.11 min, ([M+H]$^+$=434).

A mixture of compound 50 (2.5 g, 5.77 mmol), CuI (1.37 g, 7.19 mmol), Cs$_2$CO$_3$ (3.90 g, 12 mmol), 1,10-phenanthroline (2.60 g, 14.4 mmol) and butanol (25 ml) was heated at 150° C. for 4 hours in the microwave.

The mixture was cooled to room temperature. Ethyl acetate was added and the organic layer was washed met a 2 N NaOH solution, dried (Na$_2$SO$_4$), filtered and concentrated in vacuo. The resulting residue was purified by flash chromatography (gradient EtOH to EtOH/triethylamine 300/1) followed by a second flash chromatography (EtOH/ethyl acetate/triethylamine 25/75/1) to afford compound 51A as an oil (0.33 g, 15%). LCMS (method B); $R_t$: 3.27 min, ([M+H]$^+$=380).

To a solution of anhydrous THF (5 ml) containing compound 51A (0.33 g, 0.86 mmol) were added 3.5 ml of TBAF (1.0 M in THF) under $N_2$. After the addition, the resulting solution was stirred for 20 hours at room temperature and subsequently concentrated in vacuo. Ethyl acetate was added and the organic layer was washed with a concentrated NaHCO$_3$ solution, dried (Na$_2$SO$_4$), filtered and concentrated in vacuo. The resulting residue was purified by flash chromatography (gradient EtOH to EtOH/triethylamine 97/3), followed by a preparative HPLC purification: PrepHPLC (system CHSLCPO$_2$), Column: Inertsil ODS-3, 8 um. Eluens 10%/90% CH$_3$CN/H$_2$O+HCOOH, 50 ml/min, to afford the title compound 52A. (oil, 0.1 g, 45%). LCMS (method A): $R_t$: 1.0 min, ([M+H]$^+$=250). $^1$H-NMR (600 MHz, D$_6$DMSO+a few drops of HCOOH): δ 8.63 (s, 1H), 7.2 (s, 1H), 3.99-3.93 (m, 1H), 3.85 (t, J=7 Hz, 2H), 3.54-3.26 (m, 5H), 3.19-3.12 (m, 1H), 2.36-2.32 (m, 1H), 2.12-1.95 (m, 3H), 1.76-1.70 (m, 2H), 1.67-1.60 (m, 1H), 1.50-1.42 (m, 2H), 0.98 (t, J=7 Hz, 3H).

3-(4-Propoxy-1H-pyrazol-3-yl)-1-azabicyclo[2.2.2]octane (Compound 52B)

Compound 52B was prepared following the procedure as described for the synthesis of compound 52A (see Scheme 10) using propanol and 3-[4-iodo-1-(2-trimethylsilanyl-ethoxymethyl)-1H-pyrazol-3-yl]-1-azabicyclo[2.2.2]octane (50). Work-up and flash chromatography (gradient EtOH to EtOH/triethylamine 300/1) followed by a second flash chromatography (EtOH/ethyl acetate/triethylamine 25/75/1) afforded compound 51B as an oil (14%). LCMS (method B): $R_t$: 7.15 min, ([M+H]$^+$=366). Compound 51A was subsequently deprotected (TBAF/THF) and purified by flash chromatography (gradient EtOH to EtOH/triethylamine 97/3), followed by a preparative TLC purification (CH$_3$CN/H$_2$O) to afford the title compound 52B as an oil. (51%). LCMS (method A); $R_t$: 0.91 min, ([M+H]$^+$=236). $^1$H-NMR (600 MHz, D$_6$DMSO): δ 7.34 (s, 1H), 3.74 (t, J=7 Hz, 2H), 3.24-3.19 (m, 1H), 3.03-2.96 (m, 1H), 2.92-2.87 (m, 1H), 2.86-2.74 (m, 3H), 2.69-2.62 (m, 1H), 1.88-1.84 (m, 1H), 1.67-1.55 (m, 5H), 1.26-1.20 (m, 1H), 0.92 (t, J=7 Hz, 3H).

3-(4-Pentyloxy-1H-pyrazol-3-yl)-1-azabicyclo[2.2.2]octane (Compound 52C)

Compound 52C was prepared following the procedure as described for the synthesis of compound 52A (see Scheme 10) using pentanol (25 ml) and 3-[4-iodo-1-(2-trimethylsilanyl-ethoxymethyl)-1H-pyrazol-3-yl]-1-azabicyclo[2.2.2]octane (50), (2 g, 4.61 mmol). Work-up and flash chromatography (gradient EtOH to EtOH/triethylamine 300/1) followed by a second flash chromatography (EtOH/ethyl acetate/triethylamine 25/75/1) afforded compound 51C as an oil (0.46 g, 15%). LCMS (method B); $R_t$: 3.30 min, ([M+H]$^+$=394).

To a solution of SEM-protected pyrazole 51C (0.46 g, 1.2 mmol) in EtOH (5 ml) was added HCl (4 M in dioxane, 1 ml, 4 mmol) and the reaction mixture was stirred at 75° C. for 20 hours. Subsequent purification by flash chromatography (gradient EtOH to EtOH/triethylamine 97/3), followed by a preparative HPLC purification: PrepHPLC (system CHSLCPO$_2$), Column: Inertsil ODS-3, 8 um. Eluens 10%/90% CH$_3$CN/H$_2$O+HCOOH, 50 ml/min, afforded the title compound 52C. (oil, 60 mg, 19%).

$^1$H-NMR (600 MHz, D$_6$DMSO+a few drops of HCOOH): δ 8.65 (s, ~1H), 7.2 (s, 1H), 3.96-3.90 (m, 1H), 3.84 (t, J=7 Hz, 2H), 3.54-3.46 (m, 1H), 3.45-3.26 (m, 4H), 3.19-3.12 (m, 1H), 2.36-2.32 (m, 1H), 2.12-1.95 (m, 3H), 1.79-1.74 (m, 2H), 1.67-1.60 (m, 1H), 1.45-1.35 (m, 4H), 0.95 (t, J=7 Hz, 3H).

Exo-6-(1H-pyrazol-3-yl)-1-azabicyclo[3.2.1]octan-6-ol (Compound 55, Scheme 11)

A suspension of propargylaldehyde diethyl acetale (14.62 g, 114 mmol) and t-BuOK (14.92 g, 133 mmol) in 350 ml of anhydrous THF was stirred for 1 hour at −10° C. under $N_2$. Then a suspension of 1-aza-bicyclo[3.2.1]octan-6-one (53, J. Med. Chem., 36, 1993, 683-689) (11.92 g, 95 mmol) in 100 ml of THF was added and the resulting homogeneous reaction mixture was stirred for another 2 hours at 0° C. Then the mixture was quenched with an aqueous acetic acid solution at 0° C. and concentrated in vacuo. Ethyl acetate was added and the organic layer was washed with 2 N NaOH, dried (Na$_2$SO$_4$), filtered and concentrated in vacuo. Purification by flash chromatography (dichloromethane/MeOH/NH$_4$OH 93/7/0.5) afforded 6-(3,3-diethoxy-prop-1-ynyl)-1-azabicyclo[3.2.1]octan-6-ol (54) as an oil (20.87 g, 86%). LCMS (Method A): $R_t$: 1.18 min, ([M+H]$^+$=254). $^1$H-NMR (400 MHz, CDCl$_3$): δ 5.28 (s, 1H), 3.74-3.65 (m, 2H), 3.61-3.52 (m, 2H), 3.45 (d, J=13 Hz, 1H), 3.12-3.04 (m, 1H), 3.0-2.82 (m, 4H), 2.22-2.18 (m, 1H), 2.17-2.02 (m, 1H), 1.98-1.89 (m, 1H), 1.71-1.61 (m, 1H), 1.39-1.30 (m, 1H), 1.22 (t, J=7 Hz, 6H).

Compound 54 (15.39 g, 60.7 mmol) and 7.02 g of hydrazine dihydrochloride were combined in EtOH/H$_2$O (3/2, 250 ml) and warmed to reflux for 18 hour under $N_2$. The mixture was cooled, concentrated and re-dissolved in MeOH. To the reaction mixture was added Amberlyte IRA-95 (basic) and subsequently stirred for 18 hours at room temperature. The mixture was filtrated, concentrated and re-dissolved in MeOH. Filtration over 100 g of SCX-2 (MeOH followed by 1 N NH$_3$/MeOH) afforded the title compound 55 (amorphous). Yield 8.45 g (72%). $^1$H-NMR (600 MHz, D$_6$DMSO+a few drops of CF$_3$COOH): δ 7.70 (d, J=2 Hz, 1H), 6.42 (d, J=2 Hz, 1H), 4.24-4.20 (m, 1H), 3.41-3.31 (m, 4H), 3.25-3.21 (m, 1H), 2.45-2.42 (m, 1H), 2.40-2.30 (m, 1H), 2.10-2.04 (m, 1H), 1.74-1.64 (m, 2H), used techniques are DEPT, HSQC, COSY, HMBC, ROESY and NOESY Endo-6-(1H-pyrazol-3-yl)-1-azabicyclo[3.2.1]octane (Compound 58, Scheme 11)

Compound 55 (7.83 g, 41 mmol) and 9.81 ml (120 mmol) of pyridine were combined in benzene (150 ml). Acetic anhydride was added (11.48 ml, 120 mmol) and the reaction mixture was warmed to 40° C. for 72 hour under $N_2$. The mixture was cooled, concentrated and re-dissolved in MeOH. Filtration over 100 g of SCX-2 (MeOH followed by 1 N NH$_3$/MeOH) afforded compound 56 (amorphous, 9.6 g, ~100%), LCMS (method A): $R_t$: 0.98 min, ([M+H]$^+$=236), which was used without further purification.

Compound 56 (1.2 g, 5.1 mmol) was heated (in the neat) at 200° C. for 5 min under reduced pressure (23 mbar) and subsequently cooled to room temperature. Purification by flash chromatography (dichloromethane/MeOH/NH$_4$OH 85/15/1) afforded 6-(1H-pyrazol-3-yl)-1-azabicyclo[3.2.1]oct-6-ene (57) as an oil (0.49 g, 49%). LCMS (Method A); $R_t$: 1.27 min, ([M+H]$^+$=176). $^1$H-NMR (400 MHz, CDCl$_3$): δ 7.56 (d, J=2 Hz, 1H), 6.43 (s, 1H), 6.36 (d, J=2 Hz, 1H), 3.50-3.45 (m, 1H), 3.06-2.97 (m, 1H), 2.93 (d, J=10 Hz, 1H), 2.86-2.79 (m, 2H), 2.06-1.93 (m, 1H), 1.78-1.72 (m, 1H), 1.49-1.41 (m, 1H).

Compound 57 (3.84 g, 21.9 mmol), 6.9 g of ammonium formate (110 mmol) and 20% Pd(OH)$_2$/C (340 mg) were combined in MeOH (150 ml) and warmed to reflux for 1 hour. The mixture was cooled, filtered, concentrated and re-dissolved in MeOH. Filtration over 40 g of SCX-2 (MeOH followed by 1 N NH$_3$/MeOH) and subsequent purification by flash chromatography (MeOH/triethylamine 90/3) afforded endo-6-(1H-pyrazol-3-yl)-1-azabicyclo[3.2.1]octane (58), (amorphous, 2.8 g, 73%). LCMS (method A); R$_t$: 0.80 min, ([M+H]$^+$=178). $^1$H-NMR (600 MHz, D$_6$DMSO/CDCl$_3$ (1/1)): δ 7.54 (d, J=2 Hz, 1H), 6.16 (d, J=2 Hz, 1H), 3.98-3.92 (m, 1H), 3.90-3.84 (m, 1H), 3.82-3.77 (m, 1H), 3.53-3.48 (m, 1H), 3.32-3.24 (m, 3H), 2.82-2.77 (m, 1H), 2.03-1.94 (m, 1H), 1.68-1.60 (m, 1H), 1.58-1.52 (m, 1H), 1.51-1.47 (m, 1H), used techniques are DEPT, HSQC, COSY, HMBC, ROESY and NOESY.

Endo-6-(4-pentylsulfanyl-1H-Pyrazol-3-yl)-1-azabicyclo[3.2.1]octane (Compound 60A, Scheme 11)

To a solution of 58 (1.49 g, 8.41 mmol) in anhydrous DMF (60 ml) at −10° C. were added 2.68 g (10.93 mmol) of N-iodosuccinimide. The reaction mixture was stirred for 2 hours at −10° C. and 1 hour at room temperature. The solvent was (partly) removed under reduced pressure. MeOH was added and the resulting reaction mixture was filtrated over 120 g of SCX-2 (MeOH followed by 1 N NH$_3$/MeOH) to afford endo-6-(4-iodo-1H-pyrazol-3-yl)-1-azabicyclo[3.2.1]octane (59), (amorphous, 1.73 g, 67%). LCMS (Method A); R$_t$: 1.25 min, ([M+H]$^+$=304). $^1$H-NMR (600 MHz, D$_6$DMSO+ CF$_3$COOH): δ 7.72 (s, 1H), 4.08-4.03 (m, 1H), 3.80-3.75 (m, 1H), 3.73-3.68 (m, 1H), 3.50-3.45 (m, 1H), 3.34-3.25 (m, 3H), 3.04-3.0 (m, 1H), 2.24-2.14 (m, 1H), 1.64-1.57 (m, 1H), 1.50-1.42 (m, 1H), 1.22-1.17 (m, 1H), used techniques are DEPT, HSQC, COSY, HMBC, ROESY and NOESY.

Compound 59 (0.50 g; 1.65 mmol), K$_2$CO$_3$ (0.3 g; 2.14 mmol) and pentane-1-thiol (0.26 ml, 2.06 mmol) were dissolved in 20 ml of xylene/DMF (9/1) and the solution was degassed for 45 minutes with argon. To this solution were added Pd$_2$(dba)$_3$ (150 mg; 0.165 mmol) and Xantphos (190 mg; 0.33 mmol). After the addition, the reaction mixture was heated up to 130° C. and stirred for 20 hours under N$_2$. The mixture was cooled, concentrated and re-dissolved in MeOH. Filtration over 75 g of SCX-2 (MeOH followed by 1 N NH$_3$/MeOH) and subsequent purification by flash chromatography (MeOH/triethylamine (97/3)) afforded the title compound 60A as an oil. Yield 150 mg (32%). Compound 60A was reacted with 1 equivalent of fumaric acid in EtOH and concentrated (amorphous).

LCMS (method A); R$_t$: 1.39 min, ([M+H]$^+$=280). $^1$H-NMR (600 MHz, D$_6$DMSO): δ 7.85 (s, 1H), 6.43 (s, 2H), 3.80-3.70 (m, 2H), 3.63-3.58 (m, 1H), 3.28-3.22 (m, 1H), 3.20-3.19 (m, 3H), 2.82-2.78 (m, 1H), 2.63-2.55 (m, 2H), 2.12-2.01 (m, 1H), 1.65-1.56 (m, 1H), 1.50-1.44 (m, 2H), 1.37-1.15 (m, 6H), 0.85 (t, J=7 Hz, 3H).

Endo-6-(4-butylsulfanyl-1H-pyrazol-3-yl)-1-azabicyclo[3.2.1]octane (Compound 60B)

Compound 60B was prepared following the procedure as described for the synthesis of compound 60A (see Scheme 11) using butane-1-thiol and endo-6-(4-iodo-1H-pyrazol-3-yl)-1-azabicyclo[3.2.1]-octane (50). Compound 60B was reacted with 1 equivalent of fumaric acid in EtOH and concentrated. Yield: 49% (amorphous). LCMS (method A); R$_t$: 1.71 min, ([M+H]$^+$=266). $^1$H-NMR (600 MHz, D$_6$DMSO): δ 7.80 (s, 1H), 6.46 (s, 2H), 3.94-3.89 (m, 1H), 3.86-3.81 (m, 1H), 3.79-3.74 (m, 1H), 3.45-3.41 (m, 1H), 3.31-3.22 (m, 3H), 2.93-2.89 (m, 1H), 2.62-2.55 (m, 2H), 2.21-2.11 (m, 1H), 1.66-1.59 (m, 1H), 1.49-1.42 (m, 2H), 1.40-1.33 (m, 2H), 1.26-1.20 (m, 2H), 0.86 (t, J=7 Hz, 3H).

3-(4-Bromo-isoxazol-3-yl)-pyridine (Compound 64, Scheme 12)

To a solution of anhydrous THF (250 ml) containing 3-pyridinealdoxim (61) (18.87 g, 154.7 mmol) were added 20.57 g (1.0 eq) of N-chlorosuccinimide. After the addition, the resulting solution was stirred for 18 hours at 65° C. Then the temperature of the reaction mixture was lowered to −30° C. and 1,2-bis-trimethylsilanyl-ethyne was added (26.4 g, 170.4 mmol), subsequently followed by triethylamine (2 eq, 42 ml, dropwise), while keeping the temperature <−25° C. After stirring for another 30 minutes, the mixture was allowed to warm to ambient temperature, diluted with ethyl acetate, washed three times with a saturated NaHCO$_3$ solution, dried (Na$_2$SO$_4$), filtered and concentrated. The resulting residue was purified by flash chromatography (diethyl ether/PE 1/1) to afford 3-(4,5-bis-trimethylsilanyl-isoxazol-3-yl)-pyridine (62) as an oil (4.45 g, 17%). $^1$H-NMR (400 MHz, CDCl$_3$): δ 8.70 (dd, J=5 Hz, 2 Hz, 1H), 8.68 (d, J=2 Hz, 1H), 7.76 (dt, J=8 Hz, 2 Hz, 1H), 7.41-7.37 (m, 1H), 0.46 (s, 9H), 0.011 (s, 9H).

To a solution of anhydrous CCl$_4$ (80 ml) containing compound 62 (4.45 g, 15.4 mmol) was added (1.1 eq, 1.04 ml) Br$_2$. After the addition, the resulting solution was stirred for 18 hours at 40° C. The reaction mixture was cooled and concentrated in vacuo. Ethyl acetate was added and the organic layer was washed with a saturated NaHCO$_3$ solution, dried (Na$_2$SO$_4$), filtered and concentrated in vacuo. Purification by flash chromatography (diethyl ether) afforded 3-(4-bromo-5-trimethylsilanyl-isoxazol-3-yl)-pyridine (63) as an oil (4.5 g, ~100%). $^1$H-NMR (400 MHz, CDCl$_3$) δ 9.08 (d, J=2 Hz, 1H), 8.73 (dd, J=5 Hz, 2 Hz, 1H), 8.14 (dt, J=8 Hz, 2 Hz, 1H), 7.46-7.41 (m, 1H), 0.40 (s, 9H).

To a solution of EtOH (20 ml) containing compound 63 (4.5 g, 15.4 mmol) were added 5 ml of 25% NH$_4$OH. After the addition, the resulting solution was stirred for 10 minutes at room temperature. The reaction mixture was concentrated in vacuo. Ethyl acetate was added and the organic layer was washed with a saturated NaHCO$_3$ solution, dried (Na$_2$SO$_4$), filtered and concentrated in vacuo. Purification by flash chromatography (diethyl ether) afforded the title compound (64) as an oil (2.76 g, 82%). (TLC diethyl ether R$_f$ 0.4). $^1$H-NMR (400 MHz, CDCl$_3$): δ 9.14 (d, J=2 Hz, 1H), 8.76 (dd, J=5 Hz, 2 Hz, 1H), 8.58 (s, 1H), 8.19 (dt, J=8 Hz, 2 Hz, 1H), 7.48-7.43 (m, 1H).

3-(4-Butylsulfanyl-isoxazol-3-yl)-1,2,5,6-tetrahydro-1-methylpyridine (Compound 66A, Scheme 12)

To a degassed solution of dioxane (40 ml) containing 64 (1.0 g, 4.44 mmol), were added 1.2 eq (0.62 ml) of butane-1-thiol and 2 eq of triethylamine (1.52 ml). The resulting mixture was stirred for another 2 hours under N$_2$. Successively were added 2.5 mol % of Pd$_2$(dba)$_3$ (100 mg) and 5 mol % of Xantphos (128 mg). After the addition, the resulting solution was stirred for 18 hours at 95° C. under N$_2$. After cooling to room temperature, the mixture was diluted with ethyl acetate, washed with a saturated NaHCO$_3$ solution, dried (Na$_2$SO$_4$), filtered and concentrated. The resulting residue was purified by flash chromatography (diethyl ether) to afford 3-(4-butylsulfanyl-isoxazol-3-yl)-pyridine (65A) as an oil (0.26 g, 25%). (TLC diethyl ether R$_f$ 0.54). $^1$H-NMR (400 MHz, CDCl$_3$): δ 9.24 (d, J=2 Hz, 1H), 8.72 (dd, J=5 Hz, 2 Hz, 1H), 8.49 (s, 1H), 8.31 (dt, J=8 Hz, 2 Hz, 1H), 7.45-7.41 (m, 1H), 2.61 (t, J=7 Hz, 2H), 1.52-1.43 (m, 2H), 1.39-1.29 (m, 2H), 0.83 (t, J=7 Hz, 3H).

1 Eq of sulfuric acid dimethyl ester (0.14 ml, 1.5 mmol) was added to a solution of 65A (0.35 g, 1.5 mmol) in acetone (20 ml) and the mixture was stirred for 18 hours at room temperature. The precipitated crystals were filtered, washed extensively with diethyl ether and dried to afford the corresponding pyridinium sulfuric acid mono methyl ester derivative. To a cooled (−30° C.) suspension of this compound in MeOH (25 ml), sodium borohydride (0.17 g, 4.5 mmol) was added in small portions. The mixture was allowed to warm to ambient temperature and poured into a saturated NH$_4$Cl solution (0° C.). The solvent was (partly) removed under reduced pressure. Ethyl acetate was added and the organic layer was washed with a saturated NaHCO$_3$ solution, dried (Na$_2$SO$_4$), filtered and concentrated in vacuo. The resulting residue was purified by flash chromatography (MeOH) to afford the title compound 66A. (amorphous, 1.09 g, 73% (overall)). LCMS (method A): R$_t$: 1.58 min, ([M+H]$^+$=253). $^1$H-NMR (600 MHz, CDCl$_3$): δ 8.23 (s, 1H), 7.06-7.04 (m, 1H), 3.40-3.38 (m, 2H), 2.68 (t, J=7 Hz, 2H), 2.59 (t, J=7 Hz, 2H), 2.48-2.42 (m, 5H), 1.57-1.51 (m, 2H), 1.44-1.37 (m, 2H), 0.90 (t, J=7 Hz, 3H).

3-(4-Hexylsulfanyl-isoxazol-3-yl)-1,2,5,6-tetrahydro-1-methylpyridine (Compound 66B)

To a degassed solution of dioxane (30 ml) containing 64 (0.6 g, 2.66 mmol) (see Scheme 12), were added 1.2 eq (0.62 ml) of hexane-1-thiol and 2 eq of triethylamine (0.92 ml). The resulting mixture was stirred for another 2 hours under N$_2$. Successively were added 2.5 mol % of Pd$_2$(dba)$_3$ (61 mg) and 5 mol % Xantphos (77 mg). After the addition, the resulting solution was stirred for 18 hours at 95° C. under N$_2$. After cooling to room temperature, the mixture was diluted with ethyl acetate, washed with a saturated NaHCO$_3$ solution, dried (Na$_2$SO$_4$), filtered and concentrated. The resulting residue was purified by flash chromatography (diethyl ether) to afford 3-(4-Hexylsulfanyl-isoxazol-3-yl)-pyridine (65B) as an oil (0.25 g, 37%). $^1$H-NMR (400 MHz, CDCl$_3$): δ 9.24 (d, J=2 Hz, 1H), 8.73 (dd, J=5 Hz, 2 Hz, 1H), 8.49 (s, 1H), 8.31 (dt, J=8 Hz, 2 Hz, 1H), 7.45-7.41 (m, 1H), 2.61 (t, J=7 Hz, 2H), 1.52-1.43 (m, 2H), 1.35-1.13 (m, 6H), 0.85 (t, J=7 Hz, 3H).

1 Eq of sulfuric acid dimethyl ester (0.09 ml, 0.95 mmol) was added to a solution of 65A (0.25 g, 0.95 mmol) in acetone (20 ml) and the mixture was stirred for 18 hours at room temperature. The precipitated crystals were filtered, washed extensively with diethyl ether and dried to afford the corresponding pyridinium sulfuric acid mono methyl ester derivative. To a cooled (−30° C.) suspension of this compound in MeOH (25 ml), sodium borohydride (0.144 g, 4 eq.) was added in small portions. The mixture was allowed to warm to ambient temperature and poured into a saturated NH$_4$Cl solution (0° C.). The solvent was (partly) removed under reduced pressure. Ethyl acetate was added and the organic layer was washed with a saturated NaHCO$_3$ solution, dried (Na$_2$SO$_4$), filtered and concentrated in vacuo. The resulting residue was purified by flash chromatography (MeOH) to afford the title compound 66B. (amorphous, 0.72 g, 65% (overall)). LCMS (method A); R$_t$: 1.92 min, ([M+H]$^+$=281). $^1$H-NMR (400 MHz, CDCl$_3$): δ 8.23 (s, 1H), 7.06-7.04 (m, 1H), 3.40-3.38 (m, 2H), 2.67 (t, J=7 Hz, 2H), 2.59 (t, J=7 Hz, 2H), 2.48-2.42 (m, 5H), 1.59-1.51 (m, 2H), 1.41-1.21 (m, 6H), 0.85 (t, J=7 Hz, 3H).

3-(4-Hex-1-enyl-isoxazol-3-yl)-1,2,5,6-tetrahydro-1-methylpyridine (Compound 68A, Scheme 13)

To anhydrous THF (30 ml) containing compound 64 (0.64 g, 2.84 mmol), were added 1.5 eq of (E)-hexene-1-ylboronic acid (0.55 g). The resulting mixture was stirred for 2 hours under N$_2$. Successively were added 2 eq of K$_3$PO$_4$ (1.2 g), 2 mol % of Pd(OAc)$_2$ (13 mg) and 4 mol % of S-Phos (47 mg). After the addition, the resulting solution was warmed at 65° C. for 18 hours under N$_2$. After cooling to room temperature, the mixture was diluted with ethyl acetate, washed with a saturated NaHCO$_3$ solution, dried (Na$_2$SO$_4$), filtered and concentrated. The resulting residue was purified by flash chromatography (diethyl ether/PE 1/1) to afford 3-(4-hex-1-enyl-isoxazol-3-yl)-pyridine (compound 67A) as an oil (0.47 g, 69%). $^1$H-NMR (400 MHz, CDCl$_3$): δ 8.9 (d, J=2 Hz, 1H), 8.72 (dd, J=5 Hz, 2 Hz, 1H), 8.49 (s, 1H), 8.0 (dt, J=8 Hz, 2 Hz, 1H), 7.45-7.41 (m, 1H), 6.11-5.99 (m, 2H), 2.22-2.14 (m, 2H), 1.46-1.29 (m, 4H), 0.91 (t, J=7 Hz, 3H).

3-(4-Hex-1-enyl-1H-pyrazol-3-yl)-pyridine (67A) was converted to the title compound 68A, using the methodology described for the conversion of 65A to 66A (see Scheme 12). Yield: 95% (amorphous). LCMS (method A): R$_t$: 1.68 min, ([M+H]$^+$=247). $^1$H-NMR (400 MHz, CDCl$_3$): δ 8.28 (s, 1H), 6.36-6.30 (m, 1H), 6.09-5.93 (m, 2H), 3.46-3.41 (m, 2H), 2.70 (t, J=7 Hz, 2H), 2.52 (s, 3H), 2.51-2.45 (m, 2H), 2.21-2.14 (m, 2H), 1.47-1.31 (m, 4H), 0.92 (t, J=7 Hz, 3H).

3-(4 Oct-1-enyl-isoxazol-3-yl)-1,2,5,6-tetrahydro-1-methylpyridine (Compound 68B)

To anhydrous THF (20 ml) containing 64 (0.49 g, 2.17 mmol) (see Scheme 13), were added 1.5 eq of (E)-octene-1-ylboronic acid (0.51 g). The resulting mixture was stirred for 2 hours under N$_2$. Successively were added 2 eq of K$_3$PO$_4$ (0.92 g), 2 mol % of Pd(OAc)$_2$ (10 mg) and 4 mol % of S-Phos (36 mg). After the addition, the resulting solution was warmed at 65° C. for 18 hours under N$_2$. After cooling to room temperature, the mixture was diluted with ethyl acetate, washed with a saturated NaHCO$_3$ solution, dried (Na$_2$SO$_4$), filtered and concentrated. The resulting residue was purified by flash chromatography (diethyl ether/PE 1/1) to afford 3-(4 Oct-1-enyl-isoxazol-3-yl)-pyridine (compound 67B) as an oil (0.19 g, 34%). $^1$H-NMR (400 MHz, CDCl$_3$): δ 8.9 (d, J=2 Hz, 1H), 8.72 (dd, J=5 Hz, 2 Hz, 1H), 8.49 (s, 1H), 7.9 (dt, J=8 Hz, 2 Hz, 1H), 7.45-7.40 (m, 1H), 6.11-5.99 (m, 2H), 2.21-2.13 (m, 2H), 1.46-1.38 (m, 2H), 1.37-1.21 (m, 6H), 0.91 (t, J=7 Hz, 3H).

3-(4 Oct-1-enyl-1H-pyrazol-3-yl)-pyridine (67B) was converted to the title compound 68B, using the methodology described for the conversion of 65A to 66A (see Scheme 12). Yield: 54% (amorphous). LCMS (method A); R$_t$: 2.0 min, ([M+H]$^+$=275). $^1$H-NMR (400 MHz, CDCl$_3$): δ 8.28 (s, 1H), 6.32-6.27 (m, 1H), 6.09-5.93 (m, 2H), 3.37-3.33 (m, 2H), 2.61 (t, J=7 Hz, 2H), 2.45 (s, 3H), 2.44-2.39 (m, 2H), 2.20-2.12 (m, 2H), 1.48-1.38 (m, 2H), 1.37-1.24 (m, 6H), 0.85 (t, J=7 Hz, 3H).

3-(4-Hept-1-ynyl-isoxazol-3-yl)-1,2,5,6-tetrahydro-1-methylpyridine (Compound 70A, Scheme 13)

To anhydrous DMF (20 ml) containing compound 64 (1.08 g, 4.8 mmol), were added 1.5 eq of hept-1-ynyl-trimethylsilane (1.21 g), 3 eq of KOAc (1.41 g) and 1 eq of TBAF (1.0 M in THF). The resulting mixture was stirred for another 2 hours under $N_2$. Successively were added 10 mol % of $Pd(OAc)_2$ (108 mg) and 20 mol % of $PPH_3$ (251 mg). After the addition, the resulting solution was warmed at 90° C. for 18 hours under $N_2$. After cooling to room temperature, the mixture was diluted with ethyl acetate, washed three times with a saturated $NaHCO_3$ solution, dried ($Na_2SO_4$), filtered and concentrated. The resulting residue was purified by flash chromatography (diethyl ether/PE 1/1) to afford 3-(4-Hept-1-ynyl-isoxazol-3-yl)-pyridine (69A) as an oil (0.34 g, 30%). $^1$H-NMR (400 MHz, $CDCl_3$): δ 9.3 (d, J=2 Hz, 1H), 8.7 (dd, J=5 Hz, 2 Hz, 1H), 8.58 (s, 1H), 8.34 (dt, J=8 Hz, 2 Hz, 1H), 7.44-7.39 (m, 1H), 2.42 (t, J=7 Hz, 2H), 1.65-1.57 (m, 2H), 1.45-1.29 (m, 4H), 0.91 (t, J=7 Hz, 3H).

3-(4-Hept-1-ynyl-1H-pyrazol-3-yl)-pyridine (69A) was converted to the title compound 70A, using the methodology described for the conversion of 65A to 66A (see Scheme 12). Yield: 50% (amorphous). LCMS (method A): $R_t$: 1.78 min, ([M+H]$^+$=259). $^1$H-NMR (400 MHz, $CDCl_3$): δ 8.40 (s, 1H), 7.18-7.13 (m, 1H), 3.41-3.36 (m, 2H), 2.59 (t, J=7 Hz, 2H), 2.45 (s, 3H), 2.45-2.38 (m, 2H), 1.64-1.55-2.12 (m, 2H), 1.46-1.30 (m, 4H), 0.91 (t, J=7 Hz, 3H).

3-[5-Bromo-3-(2-trimethylsilanyl-ethoxymethyl)-3H-imidazol-4-yl]-pyridine (Compound 73, Scheme 14)

To anhydrous THF (100 ml) containing 3-bromo-pyridine (3.29 g, 20.82 mmol), were added 1.2 eq of /PrMgCl (12.49 ml, 2M in THF) and the resulting mixture was stirred for 2 hours under $N_2$ (10° C.). Subsequently 1.2 eq of $(CH_3)_3SnCl$ were added and the reaction mixture was stirred for 18 hours at room temperature (under $N_2$). The reaction mixture was quenched with a saturated $NH_4Cl$ solution, diluted with ethyl acetate, washed three times with a saturated $NaHCO_3$ solution, dried ($Na_2SO_4$), filtered and concentrated. The resulting residue was purified by flash chromatography (diethyl ether/PE 1/1) to afford 3-trimethylstannanyl-pyridine (71) (3.32 g, 66%). LCMS (method A): $R_t$: 2.09 min, ([M+H]$^+$=242). $^1$H-NMR (400 MHz, $CDCl_3$): δ 8.62 (bs, 1H), 8.52 (dd, J=5 Hz, 2 Hz, 1H), 7.76 (dt, J=8 Hz, 2 Hz, 1H), 7.25-7.21 (m, 1H), 0.33 (s, 9H), with Sn satellites at 0.41 and 0.27.

To a solution of 71 (0.82 g, 3.4 mmol) in anhydrous toluene (50 ml) were added 0.9 eq (1.10 g) of 4,5-dibromo-1-(2-trimethylsilanyl-ethoxymethyl)-1H-imidazole (compound 72, LCMS (method A): $R_t$: 3.60 min, ([M+H]$^+$=357)) and the resulting mixture was stirred for 2 hours under $N_2$ (room temperature). To this reaction mixture were added 10 mol % of $PdCl_2(PPH_3)_2$ (240 mg). After the addition, the temperature was raised to 100° C. and the resulting solution was stirred for 18 hours under $N_2$. The reaction mixture was cooled, diluted with ethyl acetate, washed three times with a saturated $NaHCO_3$ solution, dried ($Na_2SO_4$), filtered and concentrated. The resulting residue was purified by flash chromatography (diethyl ether followed by ethyl acetate) to afford 3-[5-bromo-3-(2-trimethylsilanyl-ethoxymethyl)-3H-imidazol-4-yl]-pyridine (73) as an oil (385 mg, 36%). LCMS (method A): $R_t$: 3.40 min, ([M+H]$^+$=355). $^1$H-NMR (400 MHz, $CDCl_3$ and HMBC): δ 8.79 (d, J=2 Hz, 1H), 8.66 (dd, J=5 Hz, 2 Hz, 1H), 7.91 (dt, J=8 Hz, 2 Hz, 1H), 7.66 (s, 1H), 7.44-7.40 (m, 1H), 5.17 (s, 2H), 3.56-3.50 (m, 2H), 0.94-0.87 (m, 2H), 0.0 (s, 9H).

3-(5-Pentylsulfanyl-3H-imidazol-4-yl)-1,2,5,6-tetrahydro-1-methylpyridine (Compound 76A, Scheme 14)

To a degassed solution of xylene (100 ml) containing 73 (1.82 g, 5.16 mmol), were added 1.25 eq (0.80 ml) of pentane-1-thiol and 1.25 eq of $K_2CO_3$ (0.8 g). The resulting mixture was stirred for another 2 hours under $N_2$. Successively were added 10 mol % of $Pd_2(dba)_3$ (470 mg) and 20 mol % mmol Xantphos (600 mg). After the addition, the resulting solution was stirred for 18 hours at 130° C. under $N_2$. After cooling to room temperature, the mixture was diluted with ethyl acetate, washed with a saturated $NaHCO_3$ solution, dried ($Na_2SO_4$), filtered and concentrated. The resulting residue was purified by flash chromatography (diethyl ether followed by ethyl acetate) to afford 3-[5-pentylsulfanyl-3-(2-trimethylsilanyl-ethoxymethyl)-3H-imidazol-4-yl]-pyridine (74A) as an oil (530 mg, 30%) and starting material (73, 380 mg, 21%), $^1$H-NMR (400 MHz, $CDCl_3$): δ 9.38 (d, J=2 Hz, 1H), 8.53 (dd, J=5 Hz, 2 Hz, 1H), 8.42 (dt, J=8 Hz, 2 Hz, 1H), 7.82 (s, 1H), 7.35-7.30 (m, 1H), 5.43 (s, 2H), 3.59-3.54 (m, 2H), 2.66 (t, J=7 Hz, 2H), 1.47-1.38 (m, 2H), 1.28-1.10 (m, 4H), 0.96-0.89 (m, 2H), 0.80 (t, J=7 Hz, 3H), 0.0 (s, 9H).

3-[5-Pentylsulfanyl-3-(2-trimethylsilanyl-ethoxymethyl)-3H-imidazol-4-yl]-pyridine (74A) was converted to 3-[5-pentylsulfanyl-3-(2-trimethylsilanyl-ethoxymethyl)-3H-imidazol-4-yl]-1,2,5,6-tetrahydro-1-methylpyridine (75A) using the methodology described for the conversion of 21A to 22A (see scheme 3). Yield: 75% (amorphous). $^1$H-NMR (400 MHz, $CDCl_3$): δ 7.68 (s, 1H), 6.75-6.71 (m, 1H), 5.37 (s, 2H), 3.54-3.46 (m, 4H), 2.67 (t, J=7 Hz, 2H), 2.57 (t, J=6 Hz, 2H), 2.46 (s, 3H), 2.44-2.38 (m, 2H), 1.55-1.46 (m, 2H), 1.37-1.24 (m, 4H), 0.94-0.85 (m, 5H), 0.0 (s, 9H).

To a solution of anhydrous THF (20 ml) containing 75A (0.42 g, 1.06 mmol) were added 3.18 ml (3 eq) of TBAF (1.0 M in THF) under $N_2$. After the addition, the resulting solution was refluxed for 18 hours and subsequently concentrated in vacuo. Ethyl acetate was added and the organic layer was washed with a concentrated $NaHCO_3$ solution, dried ($Na_2SO_4$), filtered and concentrated in vacuo. The resulting residue was purified by flash chromatography (MeOH), followed by a further purification on (25 g) SCX-2 (MeOH followed by 1 N $NH_3$/MeOH) to afford the title compound 76A. (oil, 0.2 g, 73%). LCMS (Method A): $R_t$: 1.0 min, ([M+H]$^+$=266). $^1$H-NMR (400 MHz, $CDCl_3$): δ 7.54 (s, 1H), 6.36-6.31 (m, 1H), 3.49-3.46 (m, 2H), 2.75 (t, J=7 Hz, 2H), 2.64 (t, J=6 Hz, 2H), 2.47 (s, 3H), 2.43-2.38 (m, 2H), 1.55-1.49 (m, 2H), 1.35-1.23 (m, 4H), 0.85 (t, J=7 Hz, 3H).

3-(5-Hexylsulfanyl-3H-imidazol-4-yl)-1,2,5,6-tetrahydro-1-methylpyridine (Compound 76B, Scheme 14)

To a degassed solution of xylene (30 ml) containing compound 73 (0.6 g, 1.70 mmol), were added 1.25 eq (0.30 ml) of hexane-1-thiol and 1.25 eq of $K_2CO_3$ (0.29 g). The resulting mixture was stirred for another 2 hours under $N_2$. Successively were added 10 mol % of $Pd_2(dba)_3$ (160 mg) and 20 mol % of Xantphos (200 mg). After the addition, the resulting solution was stirred for 18 hours at 130° C. under $N_2$. After cooling to room temperature, the mixture was diluted with ethyl acetate, washed with a saturated $NaHCO_3$ solution, dried ($Na_2SO_4$), filtered and concentrated. The resulting residue was purified by flash chromatography (diethyl ether) to afford 3-[5-hexylsulfanyl-3-(2-trimethylsilanyl-ethoxymethyl)-3H-imidazol-4-yl]-pyridine (74B) as an oil (120 mg, 18%) and starting material (73, 380 mg), $^1$H-NMR (400 MHz, $CDCl_3$): δ 9.38 (d, J=2 Hz, 1H), 8.53 (dd, J=5 Hz, 2 Hz, 1H), 8.42 (dt, J=8 Hz, 2 Hz, 1H), 7.82 (s, 1H), 7.35-7.30 (m, 1H), 5.43 (s, 2H), 3.59-3.54 (m, 2H), 2.66 (t, J=7 Hz, 2H), 1.46-1.37 (m, 2H), 1.28-1.06 (m, 8H), 0.96-0.89 (m, 2H), 0.80 (t, J=7 Hz, 3H), 0.0 (s, 9H).

To a solution of anhydrous THF (30 ml) containing 74B (0.29 g, 0.74 mmol) were added 2.2 ml (3 eq) of TBAF (1.0 M in THF) under $N_2$. After the addition, the resulting solution was refluxed for 18 hours and subsequently concentrated in vacuo. Ethyl acetate was added and the organic layer was washed with a concentrated NaHCO₃ solution, dried (Na₂SO₄), filtered and concentrated in vacuo. The resulting residue was purified by flash chromatography (ethyl acetate) to afford 3-(5-hexylsulfanyl-3H-imidazol-4-yl)-pyridine. (77) as an oil (0.14 g, 71%). ¹H-NMR (400 MHz, CDCl₃): δ 9.25 (bs, 1H), 8.53 (dd, J=5 Hz, 2 Hz, 1H), 8.42-8.35 (m, 1H), 7.78 (s, 1H), 7.38-7.34 (m, 1H), 2.79-2.69 (m, 2H), 1.53-1.44 (m, 2H), 1.33-1.09 (m, 6H), 0.80 (t, J=7 Hz, 3H).

3-(5-Hexylsulfanyl-3H-imidazol-4-yl]-pyridine (77) was converted to the title compound (76B) using the methodology described for the conversion of 21A to 22A (see Scheme 3) (the quaternization however was done at room temperature with a slight excess of CH₃I). Yield: 70% (oil). LCMS (method A); R$_t$: 1.21 min, ([M+H]⁺=280). ¹H-NMR (400 MHz, CDCl₃): δ 7.53 (s, 1H), 6.40-6.29 (m, 1H), 3.45-3.41 (m, 2H), 2.79-2.72 (m, 2H), 2.59 (t, J=6 Hz, 2H), 2.45 (s, 3H), 2.41-2.37 (m, 2H), 1.55-1.49 (m, 2H), 1.38-1.31 (m, 2H), 1.30-1.19 (m, 4H), 0.85 (t, J=7 Hz, 3H).

§5. Pharmacological Tests (I) Assay Method for Muscarinic Receptor Ligand Screening (In Vitro; Functional Assay)

Test Substance

Compounds were dissolved in DMSO (10 mM) and diluted in assay buffer to test concentration. Prime testing was at 1 µM; for actives in antagonist mode (PI, percent inhibition with respect to reference agonist and blank >30%) as well as actives in agonist mode (PS, percent stimulation with respect to reference agonist and blank >30%) testing was continued at lower concentrations in 10-fold dilutions: 0.1 µM, 0.01 µM, etc.

Assay Characteristics Target, Species, Tissue

| Assay | Target | Species | Tissue |
|---|---|---|---|
| Muscarine M1 | GPCR-A-MA-ACH M1 | Human | CHO cells |
| Muscarine M1 | GPCR-A-MA-ACH M1 | Rabbit | vas deferens (field-stimulated) |
| Muscarine M2 | GPCR-A-MA-ACH M2 | Guinea Pig | left atrium (electrically paced) |
| Muscarine M3 | GPCR-A-MA-ACH M3 | Guinea Pig | ileum |
| Muscarine M4 | GPCR-A-MA-ACH M4 | Human | CHO cells |

Assay Characteristics Ligand (Kd, Concentration), Non Specific Binding (Compound, Concentration)

Assay Characteristics Method, Bibliography

| Assay | Method (see below) | Bibliography (see below) |
|---|---|---|
| Muscarine M1 | cell-based assay | Sur et al. (2003) |
| Muscarine M1 | isolated organ | Eltze (1988) |
| Muscarine M2 | isolated organ | Eglen at al. (1988) |
| Muscarine M3 | isolated organ | Clague et al. (1985) |
| Muscarine M4 | cell-based assay | Stables et al. (1997) |

Assay Procedures & Calculations

Assay Procedures

Isolated Organ Assays, Agonist Mode:

The tissues were exposed to a maximal concentration of the respective reference agonist to verify responsiveness and to obtain a control response. Following extensive washings and recovery of the initial state, the tissues were exposed to the test compounds or the same agonist. In the M1 and M2 receptor assays, the compounds were left in contact with the tissues until a stable response was obtained or for a maximum of 15 min. When several concentrations were tested, they were added cumulatively. In the M3 receptor assay, the compounds were left in contact with the tissues for a time sufficient to obtain a peak response or for a maximum of 10 min, then washed out. When several concentrations were tested, they were added consecutively at 40-min intervals. Where an agonist-like response was obtained, the respective reference antagonist was tested against the highest concentration of the compounds to confirm the involvement of the receptor studied in this response.

Isolated Organ Assays, Antagonist Mode:

The tissues were exposed to a submaximal concentration of the respective reference agonist to obtain a control response. In the M1 and M2 receptor assays, the test compounds or the reference antagonists were added after stabilization of the agonist-induced response then left in contact with the tissues until a stable effect was obtained or for a maximum of 15 min. When several concentrations were tested, they were added cumulatively. In the M3 receptor assay, the test compounds or the reference antagonist were added 30 min before re-exposure to the agonist which was added at 40-min intervals. Where it occurred, an inhibition of the agonist-induced response produced by the compounds indicated an antagonist activity at the receptor studied. Each compound was investigated in the three assays for agonist and antagonist activities at one or several concentrations in three separate tissues. In each assay, the reference agonist and antagonist were tested at several concentrations in three separate tissues to obtain concentration-response curves.

| Assay | Reference Agonist | Ligand EC50 (nM) | Ligand Concentration L (nM) | Reference Antagonist | Response |
|---|---|---|---|---|---|
| Muscarine M1 | acetylcholine | 0.8 | 100 (ago mode) 3 (anta mode) | pirenzepine | Ca2+ - FLIPR Fluorimetry |
| Muscarine M1 | McN-A-343 | 250 | 3000 (ago mode) 1000 (anta mode) | pirenzepine | inhibition of twitch contraction |
| Muscarine M2 | carbachol | 150 | 3000 (ago mode) 1000 (anta mode) | methoctramine | negative inotropic effect |
| Muscarine M3 | carbachol | 125 | 3000 (ago mode) 1000 (anta mode) | 4-DAMP | contraction |
| Muscarine M4 | oxotremorine | 40 | 10000 (ago mode) 10000 (anta mode) | pirenzepine | Ca2+ - Aequorin luminescence |

Cell-Based Assays:
Cells were incubated with compound and the response indicated was measured.
Response and Calculation of Results
Isolated Organ Assays:
The parameters measured were the maximum change in the amplitude of the electrically-evoked contractions (M1 and M2 receptor assays) or in tension (M3 receptor assay) induced by each compound concentration. The results are expressed as a percent of the control agonist-induced response. The EC50 values of the reference agonists (concentration producing a half-maximum response) and IC50 values of the reference antagonists (concentration producing a half-maximum inhibition of the agonist-induced response) were calculated by linear regression analysis of their concentration-response curves.
Cell-Based Assays:
The results are expressed as a percent of reference agonist values and blanks in the presence of the test compound, percent stimulation for agonist mode; for the antagonist mode (test compound in the presence of reference agonist) as percent inhibition. The EC50 values (concentration causing a half-maximal stimulation of control values), IC50 values (concentration causing a half-maximal inhibition of control values) were determined by non-linear regression analysis of the concentration-response curves using Hill equation curve fitting.

Bibliography
CLAGUE, R. U., EGLEN, R. M., STRACHAN, A. C. and WHITING, R. L. (1985) Action of agonists and antagonists at muscarinic receptors present on ileum and atria in vitro. *Brit. J. Pharmacol*, 86: 163-170.
EGLEN, R. M., MONTGOMERY, W. W., DAINTY, I. A., DUBUQUE, L. K. and WHITING, R. L. (1988) The interaction of methoctramine and himbacine at atrial, smooth muscle and endothelial muscarinic receptors in vitro. *Brit. J. Pharmacol.*, 95: 1031-1038.
ELTZE, M. (1988) Muscarinic M1- and M2-receptors mediating opposite effects on neuro-muscular transmission in rabbit vas deferens. *Eur. J. Pharmacol.*, 151: 205-221.
STABLES, J., GREEN, A., MARSHALL, F., FRASER, N., KNIGHT, E., SAUTEL, M., MILLIGAN, G., LEE, M., and REES, S. (1997) A bioluminescent assay for agonist activity at potentially any G-Protein-Coupled Receptor. *Anal. Biochem.* 252: 115-126.
SUR, C., MALLORGA, P. J., WITTMANN, M., JACOBSON, M. A., PASCARELLA, D., WILLIAMS, J. B., BRANDISH, P. E., PETTIBONE, D. J., SCOLNICK, E. M. and CONN, P. J. (2003) N-desmethylclozapine, an allosteric agonist at muscarinic 1 receptor, potentiates N-methyl-D-aspartate receptor activity. *PNAS*, 100: 13674-13679.

(II) Assay Method for Muscarinic Receptor Ligand Screening (In Vitro; Receptor Binding Assay)
Test Substance
Compounds were dissolved in DMSO (10 mM) and diluted in assay buffer to test concentration. Prime testing was at 10 µM; for actives (PI, percent inhibition with respect to total and non-specific binding >40%) testing was continued at lower concentrations in 10-fold dilutions: 1 µM, 0.1 µM, etc.
Assay Characteristics Target. Species, Tissue

| Assay | Target | Species | Tissue |
|---|---|---|---|
| Muscarine M non-selective | GPCR-A-MA-ACH M | Rat | cerebral cortex |
| Muscarine M1 | GPCR-A-MA-ACH M1 | Human | CHO cells |
| Muscarine M2 | GPCR-A-MA-ACH M2 | Human | CHO cells |
| Muscarine M3 | GPCR-A-MA-ACH M3 | Human | CHO cells |
| Muscarine M4 | GPCR-A-MA-ACH M4 | Human | CHO cells |

Assay Characteristics Ligand (Kd, Concentration), Non Specific Binding (Compound, Concentration)

| Assay | Ligand | Ligand Kd (nM) | Ligand Concentration L (nM) | Non Specific Binding Compound | Non Specific Binding Concentration (µM) |
|---|---|---|---|---|---|
| Muscarine M non-selective | 3H-QNB | 0.01 | 0.05 | Atropine | 1 µM |
| Muscarine M1 | 3H-Pirenzepine | 13 | 2 | Atropine | 1 µM |
| Muscarine M2 | 3H-AFDX384 | 4.3 | 2 | Atropine | 1 µM |
| Muscarine M3 | 3H-4DAMP | 0.5 | 0.2 | Atropine | 1 µM |
| Muscarine M4 | 3H-Oxotremorine | 4.5 | 6 | Atropine | 1 µM |
| Muscarine M4 | 3H-4DAMP | 0.332 | 0.2 | Atropine | 1 µM |

Assay Characteristics Incubation Conditions (period/temperature), Bibliography

| Assay | Incubation Conditions period/temperature | Bibliography (see below) |
|---|---|---|
| Muscarine M non-selective | 120 min/22° C. | Richards (1990) |
| Muscarine M1 | 60 min/22° C. | Dörje et al. (1991) |
| Muscarine M2 | 60 min/22° C. | Dörje et al. (1991) |
| Muscarine M3 | 60 min/22° C. | Peralta et al. (1987) |
| Muscarine M4 | 30 min/25° C. | Dörje et al. (1991) |
| Muscarine M4 | 60 min/22° C. | Dörje et al. (1991) |

Assay Procedures & Calculations
Assay Procedure
Following incubation of compound with the receptor preparation (from 'Tissue') and the Ligand at the time and temperature indicated, the receptor preparations were rapidly filtered under vacuum through glass fibre filters; the filters were washed extensively with an ice-cold buffer using a harvester. Bound radioactivity was measured by scintillation counting using a liquid scintillation cocktail.
Response and Calculation of Results
Results were expressed as percentage of total Ligand binding and that of Non Specific Binding, per concentration of Compound tested (duplicates); from the concentration—displacement curves IC50 values were determined by non-linear regression analysis using Hill equation curve fitting. The inhibition constants (Ki) were calculated from the Cheng-Prushoff equation Ki=IC50/(1+L/Kd), where L is the concentration of radioligand in the assay, and Kd the affinity of the radioligand for the receptor. Results were expressed as pki's, means±SD of at least 2 separate experiments; i.e. outliers (outside +/−1 std of mean) and discrepancies were excluded. Compounds with no significant affinity at concentrations of 10 μM and higher were concluded to be "inactive" denoted by pKi of "<5.0".

Bibliography

DÖRJE, F., WESS, J., LAMBRECHT, G., TACKE, R., MUTSCHLER, E. and BRANN, M. R. (1991) Antagonist binding profiles of five cloned human muscarinic receptor subtypes. *J. Pharmacol. Exp. Ther.*, 256: 727-733.

RICHARDS, M. H. (1990) Rat hippocampal muscarinic autoreceptors are similar to the $M_2$ (cardiac) subtype: comparison with hippocampal $M_1$, atrial $M_2$ and ileal M3 receptors. *Brit. J. Pharmacol.*, 99: 753-761.

PERALTA, E. G., ASHKENAZI, A., WINSLOW, J. W., SMITH, D. H., RAMACHANDRAN, J. and CAPON, D. J. (1987) Distinct primary structures, ligand-binding properties and tissue-specific expression of four human muscarinic acetylcholine receptors. *EMBO. J.*, 6: 3923-3929.

Determination of Metabolic Stability (In Vitro)

Method used according to procedures described by DI, L. et al., Journal of Biomolecular Screening, Vol. 8, No. 4, 453-462 (2003).

§6. Pharmacological Data

TABLE 1

Affinity to M1 and M4 receptors and efficacy.

| Compound No | RB Musc. M4 3H-DAMP pKi | RB Musc. M4 3H-Oxotremorine pKi | Cell funct. Musc. M4 Agonism pEC50 | RB Musc. M1 3H-Pirenzepine pKi | Cell funct. Musc. M1 Agonism pEC50 |
|---|---|---|---|---|---|
| 9 | 6.5 | 6.4 | <5.0 | 5.9 | 6.9 |
| 16 | n.d. | n.d. | <5.0 | n.d. | n.d. |
| 22F | 7.4 | 7.2 | 6.9 | 6.5 | 6.7 |
| 22M | 6.4 | 6.6 | <5.0 | 6.3 | n.d. |
| 26 | 6.7 | 6.6 | <5.0 | 6.8 | n.d. |
| 49A | 7.8 | 7.6 | 7.4 | 6.9 | 8.0 |
| 22N | 6.6 | 6.6 | <5.0 | 6.4 | n.d. |
| 22B | 6.9 | 6.4 | 6.3 | 6.3 | 7.1 |
| 41 | <5 | <5 | <5.0 | <5 | n.d. |
| 22A | 6.4 | 6.6 | <5.0 | 5.8 | n.d. |
| 22E | 6.5 | 7 | <5.0 | 6.4 | n.d. |
| 42 | 5.3 | 5.4 | <5.0 | 5.1 | n.d. |
| 22G | 7.3 | 6.7 | 6.5 | 6.7 | 7.4 |
| 22D | 6.4 | 6.5 | <5.0 | 5.8 | n.d. |
| 33C | 6.5 | 5.8 | 5.9 | 5.9 | 6.9 |
| 22Q | 6.3 | 6.9 | <5.0 | 6.1 | n.d. |
| 22R | 5.4 | 5.7 | <5.0 | 4.9 | n.d. |
| 22S | 7.3 | 6.8 | <5.0 | 6.9 | 6.4 |
| 33A | 6.6 | 6.3 | 6.1 | 5.9 | 6.9 |
| 22H | 7.2 | 6.9 | 8.0 | 6.7 | 6.9 |
| 33D | 6.0 | 5.8 | 5.9 | 5.6 | 7.0 |
| 66B | 7.0 | 6.8 | 6.3 | 6.2 | n.d. |
| 66A | 7.4 | 7.1 | <5.0 | 6.6 | n.d. |
| 68B | 6.0 | 6.1 | 6.1 | 5.3 | 6.1 |
| 70A | 6.7 | 6.6 | 6.2 | 6.0 | 6.6 |
| 47A | 6.1 | 6.6 | 6.3 | 5.6 | 6.8 |
| 68A | 6.6 | 6.2 | 6.1 | 5.8 | 6.7 |
| 45B | 5.9 | 6.3 | 6.5 | 5.7 | 6.9 |
| 49D | 7.0 | 6.9 | 6.8 | 6.1 | 7.4 |
| 60B | 6.8 | 6.6 | <5.0 | 6.4 | <6.0 |
| 49E | 7.4 | 7.1 | 7.1 | 6.5 | 8.0 |
| 45C | 6.1 | 6.3 | 5.7 | 6.1 | <6.0 |
| 45A | 6.2 | 6.4 | 6.1 | 5.8 | 6.9 |
| 47B | 6.5 | 6.8 | <5.0 | 6.1 | n.d. |
| 45E | 5.8 | 5.8 | <5.0 | 5.8 | <6.0 |
| 22C | 7.2 | 6.8 | <5.0 | 6.6 | <6.0 |
| 45D | 6.2 | 6.3 | 5.9 | 5.7 | 6.1 |
| 47C | 6.1 | 6.6 | 6.2 | 6.1 | 6.1 |
| 22I | 6.6 | 7.0 | 6.6 | 6.1 | 7.0 |
| 22J | 6.6 | 7.2 | 6.6 | 6.2 | 7.4 |
| 22K | 6.2 | 6.4 | 5.9 | 5.9 | 7.0 |
| 49F | 7.3 | 7.9 | 7.9 | 6.6 | 6.1 |
| 49B | 7.6 | 8.1 | 8.2 | 6.8 | 8.0 |
| 49H | 7.4 | 7.5 | <5.0 | 6.8 | 7.3 |
| 33B | 6.5 | 6.7 | 6.3 | 6.0 | 7.0 |
| 33G | 6.7 | 6.9 | 6.2 | 5.8 | 7.6 |
| 49C | 6.9 | 6.9 | 6.3 | 6.0 | 7.1 |
| 22L | 7.0 | 7.2 | 7.2 | 6.1 | 8.0 |
| 22O | 6.1 | 6.4 | 6.2 | 5.1 | 7.5 |
| 33E | 6.5 | 6.8 | 6.2 | 6.0 | 6.7 |
| 33F | 6.3 | 6.5 | 6.1 | 5.4 | 7.4 |
| 59 | 7.0 | 6.7 | <5.0 | 6.0 | 7.1 |
| 49G | 7.0 | 7.6 | 8.0 | 6.2 | 7.3 |
| 52C | 6.6 | 7.2 | n.d. | 6.0 | 7.9 |
| 52A | 6.6 | 6.9 | n.d. | 6.1 | 7.7 |
| 52B | 6.9 | 7.2 | 7.0 | 6.2 | 8.1 |
| 49I | 7.2 | 7.9 | 7.7 | 6.5 | 8.5 |
| 22P | 5.2 | 5.2 | 5.9 | <5.0 | 6.4 |
| 76B | 6.3 | 6.0 | 6.0 | 5.4 | 7.1 |
| 76A | 6.5 | 6.2 | 5.1 | 5.6 | 6.9 |
| 60A | 6.6 | 7.2 | <5.0 | 6.4 | n.d. |

(RB = receptor binding; n.d. = not done)

TABLE 2

Affinity to M2 and M3 receptors and efficacy.

| Compound No | RB Musc M2 methoctramine | Cell funct. Musc. M2 Agonism pEC50 | Cell funct. Musc. M2 Antagonism pA2 | RB Musc M3 4-DAMP | Cell funct. Musc. M3 Agonism pEC50 | Cell funct. Musc. M3 Antagonism pA2 |
|---|---|---|---|---|---|---|
| 22J | 5.5 | <6 | <6 | 6.5 | <6 | <6 |
| 33G | 5.4 | <6 | <6 | 6.1 | <6 | <6 |
| 33B | 5.9 | <6 | <6 | 6.4 | <6 | <6 |
| 22L | 5.7 | <6 | <6 | 6.5 | <6 | <6 |
| 33F | 5.3 | <6 | <6 | 6.0 | <6 | <6 |
| 22O | 5.0 | <6 | 7.7 | 5.6 | <6 | <6 |

TABLE 2-continued

Affinity to M2 and M3 receptors and efficacy.

| Compound No | RB Musc M2 methoctramine | Cell funct. Musc. M2 Agonism pEC50 | Cell funct. Musc. M2 Antagonism pA2 | RB Musc M3 4-DAMP | Cell funct. Musc. M3 Agonism pEC50 | Cell funct. Musc. M3 Antagonism pA2 |
|---|---|---|---|---|---|---|
| 49G | 6.1 | <6 | <6 | 6.5 | <6 | <6 |
| 52A | 5.4 | <6 | <6 | 6.1 | <6 | <6 |
| 52C | 5.6 | <6 | <6 | 6.2 | <6 | <6 |
| 52B | 5.9 | <6 | 7.6 | 6.5 | <6 | <6 |
| 76B | 5.2 | <6 | <6 | 5.6 | <6 | <6 |
| 76A | 5.3 | <6 | <6 | 6.1 | <6 | <6 |
| 49E | 6.3 | 6.1 | <6 | 6.9 | <6 | <6 |
| 22S | 5.7 | <6 | <6 | 7.3 | <6 | 7.0 |
| 22C | 6.4 | <6 | <6 | 7.5 | <6 | <6 |
| 49F | 6.4 | <6 | <6 | 7.0 | <6 | <6 |
| 49B | 6.2 | <6 | <6 | 7.2 | <6 | <6 |
| Methoctramine | 7.5 | | 7.9 | | | |
| 4-DAMP | | | | 9.4 | | |
| Carbachol | | 6.8 | | | | |
| McN-A-343 | | | | | 6.9 | |
| Pirenzepine | | | | | | 8.9 |

(RB = receptor binding)

TABLE 3

Stability in human liver homogenate/selected compounds

| Compound | t ½ (minutes) |
|---|---|
| 22B | 52 |
| 22G | 50 |
| 22J | 129 |
| 22L | 56 |
| 22O | 245 |
| 33F | 230 |
| 33G | 56 |
| Xanomeline (reference) | 17 |

What is claimed is:
1. A heterocyclic compound of the formula (I)

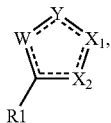
(I)

or a pharmaceutically acceptable salt thereof,
wherein
the heterocycle comprises two double bonds, which may be present at varying positions, and which are represented by the dashed lines (—);
the heterocycle contains two heteroatoms,
W is N or NH;
Y is CH, O or NH, wherein
if Y is O, X1 is CH and X2 is C—Z—R2 or C—R3, wherein Z is NH, O, or S; and
if Y is CH or NH, one of X1 and X2 is CH or N, wherein if X1 is CH or N, X2 is C—Z—R2 or C—R3, and if X2 is CH or N, X1 is C—Z—R2 or C—R3, wherein Z is NH or S;
R1 is structure (a):

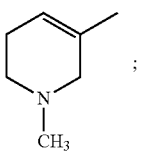
(a)

R2 is chosen from $(C_1-C_{10})$alkyl, $(C_2-C_{10})$alkenyl and $(C_2-C_{10})$alkynyl, optionally independently substituted with one or more substituents chosen from halogen, hydroxy, cyano, oxo, $(C_1-C_6)$alkoxy, $(C_1-C_6)$alkylthio, $(C_1-C_6)$alkenyloxy, $(C_1-C_6)$alkenylthio, $(C_1-C_4)$alkoxy$(C_1-C_4)$alkoxy, $(C_5-C_7)$cycloalkyl, a 5-membered unsaturated heterocycle optionally substituted with halogen, phenyl, phenyloxy and phenylthio, wherein the phenyl group is optionally substituted with halogen; and R3 is chosen from $(C_4-C_{10})$alkyl, $(C_2-C_{10})$alkenyl and $(C_2-C_{10})$alkynyl, optionally independently substituted with one or more substituents chosen from halogen, hydroxy, cyano, $(C_1-C_6)$alkoxy, $(C_1-C_6)$alkylthio, $(C_1-C_6)$alkenyloxy, $(C_1-C_6)$alkenylthio, $(C_1-C_4)$alkoxy$(C_1-C_4)$alkoxy, $(C_5-C_7)$cycloalkyl, a 5-membered unsaturated heterocycle optionally substituted with halogen, phenyl, phenyloxy and phenylthio, wherein the phenyl group is optionally substituted with halogen;

and optionally, when R2 is an unbranched $(C_2-C_8)$alkyl, R2 links to formula (Ia)

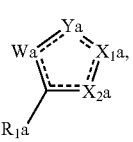
(Ia)

or a pharmaceutically acceptable salt thereof,
through the $X_1a$ or $X_2a$ of formula (Ia), wherein if $X_1$ is CH or N, $X_1a$ is CH or N and $X_2a$ is C-Za-, or
if X1 is C—Z—R2, $X_1a$ is C-Za- and $X_2a$ is CH or N, wherein $X_1a$ or $X_2a$ having Za links to R2;
wherein
Wa is N or NH;
Ya is CH, O or NH;
Za is NH, O , or S; and $R_1a$ is chosen from structure (a):

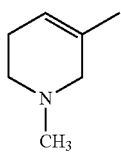
(a)

2. The compound of claim 1, wherein R2 is chosen from $(C_1-C_{10})$alkyl, $(C_2-C_{10})$alkenyl and $(C_2-C_{10})$alkynyl, optionally independently substituted with one or more substituents chosen from halogen, hydroxy, cyano, oxo, $(C_1-C_6)$alkoxy, $(C_1-C_6)$alkylthio, $(C_1-C_8)$alkenyloxy, $(C_1-C_6)$alkenylthio, $(C_1-C_4)$alkoxy$(C_1-C_4)$alkoxy, $(C_5-C_7)$cycloalkyl, a 5-membered unsaturated heterocycle optionally substituted with halogen, phenyl, phenyloxy and phenylthio, wherein the phenyl group is optionally substituted with halogen.

3. The compound of claim 2, wherein R2 is chosen from $(C_1-C_8)$alkyl, $(C_2-C_8)$alkenyl and $(C_2-C_8)$alkynyl, optionally independently substituted with one or more substituents chosen from halogen, hydroxy, cyano, $(C_1-C_6)$alkoxy, $(C_1-C_4)$alkoxy$(C_1-C_4)$alkoxy, $(C_5-C_7)$cycloalkyl, tetrahydrofuranyl and phenyl, wherein the phenyl group is optionally substituted with halogen.

4. The compound of claim 3, wherein R2 is chosen from $(C_1-C_8)$alkyl and $(C_2-C_8)$alkenyl, optionally substituted with one or more substituents chosen from halogen and $(C_1-C_6)$alkoxy.

5. The compound of claim 1, wherein R3 is chosen from $(C_4-C_{10})$alkyl,$(C_2-C_{10})$alkenyl and $(C_2-C_{10})$alkynyl, optionally substituted with a substituent chosen from $(C_5-C_7)$cycloalkyl and phenyl, wherein the phenyl group is optionally substituted with halogen.

6. The compound of claim 1, wherein R1 has the structure (a).

7. The compound of claim 1, wherein W is N and Y is NH.

8. A heterocyclic compound of the formula (I)

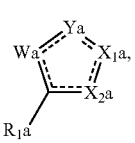
(I)

or a pharmaceutically acceptable salt thereof,
wherein
the heterocycle comprises two double bonds, which may be present at varying positions, and which are represented by the dashed lines (—);
the heterocycle contains two heteroatoms,
W is N;
Y is NH;
X1 is CH and X2 is C—Z—R2 or C—R3, wherein Z is O or S;

R1 is structure (a):

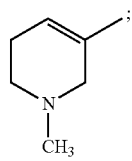
(a)

R2 is chosen from $(C_1-C_{10})$alkyl, $(C_2-C_{10})$alkenyl and $(C_2-C_{10})$alkynyl, optionally independently substituted with one or more substituents chosen from halogen, hydroxy, cyano, oxo, $(C_1-C_6)$alkoxy, $(C_1-C_6)$alkylthio, $(C_1-C_6)$alkenyloxy, $(C_1-C_6)$alkenylthio, $(C_1-C_4)$alkoxy$(C_1-C_4)$alkoxy, $(C_5-C_7)$cycloalkyl, a 5-membered unsaturated heterocycle optionally substituted with halogen, phenyl, phenyloxy and phenylthio, wherein the phenyl group is optionally substituted with halogen; and R3 is chosen from $(C_4-C_{10})$alkyl, $(C_2-C_{10})$alkenyl and $(C_2-C_{10})$alkynyl, optionally independently substituted with one or more substituents chosen from halogen, hydroxy, cyano, $(C_1-C_6)$alkoxy, $(C_1-C_6)$alkylthio, $(C_1-C_6)$alkenyloxy, $(C_1-C_6)$alkenylthio, $(C_1-C_4)$alkoxy$(C_1-C_4)$alkoxy, $(C_5-C_7)$cycloalkyl, a 5-membered unsaturated heterocycle optionally substituted with halogen, phenyl, phenyloxy and phenylthio, wherein the phenyl group is optionally substituted with halogen;

and optionally, when R2 is an unbranched $(C_2-C_8)$alkyl, R2 links to formula (Ia)

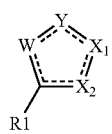
(Ia)

or a pharmaceutically acceptable salt thereof,
through the $X_1a$ or $X_2a$ of formula (Ia), wherein $X_1a$ is CH or N and $X_2a$ is C-Za-;
wherein
Wa is N or NH;
Ya is CH, O or NH;
Za is NH, O, or S; and
$R_1a$ is chosen from structure (a):

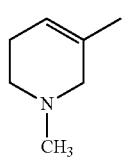
(a)

9. The compound of claim 8, wherein X2 is C—Z—R2.

10. The compound of claim 9, wherein Z is S.

11. A heterocyclic compound of the formula (I)

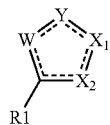
(I)

or a pharmaceutically acceptable salt thereof,
wherein
the heterocycle comprises two double bonds, which may be present at varying positions, and which are represented by the dashed lines (—);
the heterocycle contains two heteroatoms,
W is N or NH;
Y is O;
X1 is CH and X2 is C—Z—R2 or C—R3 wherein Z is O or S; and
R1 is structure (a):

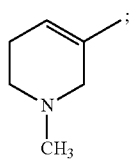
(a)

R2 is chosen from $(C_1\text{-}C_{10})$alkyl, $(C_2\text{-}C_{10})$alkenyl and $(C_2\text{-}C_{10})$alkynyl, optionally independently substituted with one or more substituents chosen from halogen, hydroxy, cyano, oxo, $(C_1\text{-}C_6)$alkoxy, $(C_1\text{-}C_6)$alkylthio, $(C_1\text{-}C_6)$alkenyloxy, $(C_1\text{-}C_6)$alkenylthio, $(C_1\text{-}C_4)$alkoxy$(C_1\text{-}C_4)$alkoxy, $(C_5\text{-}C_7)$cycloalkyl, a 5-membered unsaturated heterocycle optionally substituted with halogen, phenyl, phenyloxy and phenylthio, wherein the phenyl group is optionally substituted with halogen; and
R3 is chosen from $(C_4\text{-}C_{10})$alkyl, $(C_2\text{-}C_{10})$alkenyl and $(C_2\text{-}C_{10})$alkynyl, optionally independently substituted with one or more substituents chosen from halogen, hydroxy, cyano, $(C_1\text{-}C_6)$alkoxy, $(C_1\text{-}C_6)$alkylthio, $(C_1\text{-}C_6)$alkenyloxy, $(C_1\text{-}C_6)$alkenylthio, $(C_1\text{-}C_4)$alkoxy$(C_1\text{-}C_4)$alkoxy, $(C_5\text{-}C_7)$cycloalkyl, a 5-membered unsaturated heterocycle optionally substituted with halogen, phenyl, phenyloxy and phenylthio, wherein the phenyl group is optionally substituted with halogen;
and optionally, when R2 is an unbranched $(C_2\text{-}C_8)$alkyl, R2 links to formula (Ia)

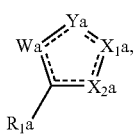
(Ia)

or a pharmaceutically acceptable salt thereof,
through the $X_1a$ or $X_2a$ of formula (Ia), wherein if $X_1$ is CH or N, $X_1a$ is CH or N and $X_2a$ is C—Za-, or
if X1 is C—Z—R2, $X_1a$ is C-Za- and $X_2a$ is CH or N, wherein $X_1a$ or $X_2a$ having Za links to R2;

wherein
Wa is N or NH;
Ya is CH, O or NH;
Za is NH, O, or S; and
$R_1a$ is chosen from structure (a):

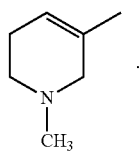
(a)

12. The compound of claim 11, wherein Z is S.
13. A compound chosen from
3-(4-Pentyl-1H-pyrazol-3-yl)-1,2,5,6-tetrahydro-1-methylpyridine;
3-(4-Butyl-1H-pyrazol-3-yl)-1,2,5,6-tetrahydro-1-methylpyridine;
3-(4-Butylsulfanyl-1H-pyrazol-3-yl)-1,2,5,6-tetrahydro-1-methylpyridine;
3-[4-(Furan-2-ylmethylsulfanyl)-1H-pyrazol-3-yl]-1,2,5,6-tetrahydro-1-methylpyridine;
3-(5-Butylsulfanyl-1H-pyrazol-3-yl)-1,2,5,6-tetrahydro-1-methylpyridine;
3-(4-Benzylsulfanyl-1H-pyrazol-3-yl)-1,2,5,6-tetrahydro-1-methylpyridine;
3-[4-(4,4,4-trifluoro-butylsulfanyl)-1H-pyrazol-3-yl]-1,2,5,6-tetrahydro-1-methylpyridine;
N-[3-(1-Methyl-1,2,5,6-tetrahydro-pyridin-3-yl)-1H-pyrazol-4-yl]-butyramide;
3-(4-Methylsulfanyl-1H-pyrazol-3-yl)-1,2,5,6-tetrahydro-1-methylpyridine;
3-(4-Propylsulfanyl-1H-pyrazol-3-yl)-1,2,5,6-tetrahydro-1-methylpyridine;
Butyl-[3-(1-methyl-1,2,5,6-tetrahydro-pyridin-3-yl)-1H-pyrazol-4-yl]-amine;
3-(4-Pentylsulfanyl-1H-pyrazol-3-yl)-1,2,5,6-tetrahydro-1-methylpyridine;
3-(4-Ethylsulfanyl-1H-pyrazol-3-yl)-1,2,5,6-tetrahydro-1-methylpyridine;
3-(4-Butyloxy-1H-pyrazol-3-yl)-1,2,5,6-tetrahydro-1-methylpyridine;
3-(4-Allylsulfanyl-1H-pyrazol-3-yl)-1,2,5,6-tetrahydro-1-methylpyridine;
3-[3-(1-Methyl-1,2,5,6-tetrahydro-pyridin-3-yl)-1H-pyrazol-4-ylsulfanyl]-propionitrile;
3-[4-(3-Methyl-butylsulfanyl)-1H-pyrazol-3-yl]-1,2,5,6-tetrahydro-1-methylpyridine;
3-[4-(3-Phenyl-propoxy)-1H-pyrazol-3-yl]-1,2,5,6-tetrahydro-1-methylpyridine;
3-(4-Hexylsulfanyl-1H-pyrazol-3-yl)-1,2,5,6-tetrahydro-1-methylpyridine;
3-(4-But-3-enyloxy-1H-pyrazol-3-yl)-1,2,5,6-tetrahydro-1-methylpyridine;
3-(4-Hexylsulfanyl-isoxazol-3-yl)-1,2,5,6-tetrahydro-1-methylpyridine;
3-(4-Butylsulfanyl-isoxazol-3-yl)-1,2,5,6-tetrahydro-1-methylpyridine;
3-(4-Oct-1-enyl-isoxazol-3-yl)-1,2,5,6-tetrahydro-1-methylpyridine;
3-(4-Hept-1-ynyl-isoxazol-3-yl)-1,2,5,6-tetrahydro-1-methylpyridine;
3-(4-Hex-1-enyl-1H-pyrazol-3-yl)-1,2,5,6-tetrahydro-1-methylpyridine;

3-(4-Hex-1-enyl-isoxazol-3-yl)-1,2,5,6-tetrahydro-1-methylpyridine;
3-(4-Hept-1-ynyl-pyrazol-3-yl)-1,2,5,6-tetrahydro-1-methylpyridine;
3-(4-Non-1-ynyl-1H-pyrazol-3-yl)-1,2,5,6-tetrahydro-1-methylpyridine;
3-(4-Hex-1-ynyl-1H-pyrazol-3-yl)-1,2,5,6-tetrahydro-1-methylpyridine;
3-{4-[2-(3-Fluoro-phenyl)-vinyl]-1H-pyrazol-3-yl}-1,2,5,6-tetrahydro-1-methylpyridine;
3-[4-(5-Cyclohexyl-pent-1-ynyl)-1H-pyrazol-3-yl]-1,2,5,6-tetrahydro-1-methylpyridine;
Bis-[3-(1-methyl-1,2,5,6-tetrahydro-pyridin-3-yl)-1H-pyrazol-4-yl]-2-sulfanylethyl]-methane;
3-[4-(5-Phenyl-pent-1-ynyl)-1H-pyrazol-3-yl]-1,2,5,6-tetrahydro-1-methylpyridine;
3-(4-Oct-1-enyl-1H-pyrazol-3-yl)-1,2,5,6-tetrahydro-1-methylpyridine;
3-[4-(3-Phenyl-propylsulfanyl)-1H-pyrazol-3-yl]-1,2,5,6-tetrahydro-1-methylpyridine;
3-[4-(4,4-Difluoro-but-3-enylsulfanyl)-1H-pyrazol-3-yl]-1,2,5,6-tetrahydro-1-methylpyridine;
3-[4-(3-Phenyl-allylsulfanyl)-1H-pyrazol-3-yl]-1,2,5,6-tetrahydro-1-methylpyridine;
3-(4-Hexyloxy-1H-pyrazol-3-yl)-1,2,5,6-tetrahydro-1-methyl pyridine;
3-(4-Pentyloxy-1H-pyrazol-3-yl)-1,2,5,6-tetrahydro-1-methyl pyridine;
3-[4-Pent-4-enylsulfanyl)-1H-pyrazol-3-yl]-1,2,5,6-tetrahydro-1-methylpyridine;
3-[4-(2-Ethoxy-ethylsulfanyl)-1H-pyrazol-3-yl]-1,2,5,6-tetrahydro-1-methylpyridine;
3-(4-Heptyloxy-1H-pyrazol-3-yl)-1,2,5,6-tetrahydro-1-methylpyridine;
3-(4-Heptyloxy-1H-pyrazol-3-yl)-1,2,5,6-tetrahydro-1-methylpyridine;
3-(4-Pent-4-enyloxy-1H-pyrazol-3-yl)-1,2,5,6-tetrahydro-1-methylpyridine;
3-[4-[2-(2-Methoxy-ethoxy)-ethylsulfanyl]-1H-pyrazol-3-yl}-1,2,5,6-tetrahydro-1-methylpyridine;
3-(5-Hexylsulfanyl-3H-imidazol-4-yl)-1,2,5,6-tetrahydro-1-methylpyridine; and
3-(5-Pentylsulfanyl-3H-imidazol-4-yl)-1,2,5,6-tetrahydro-1-methylpyridine;
or a pharmaceutically acceptable salt thereof.

14. A pharmaceutical composition comprising a compound as claimed in claim 1, and at least one other pharmacologically active substance.

15. A pharmaceutical composition comprising the compound as claimed in claim 1, and a pharmaceutically acceptable auxiliary.

* * * * *

UNITED STATES PATENT AND TRADEMARK OFFICE
CERTIFICATE OF CORRECTION

| | | |
|---|---|---|
| PATENT NO. | : 8,084,473 B2 | Page 1 of 1 |
| APPLICATION NO. | : 12/108275 | |
| DATED | : December 27, 2011 | |
| INVENTOR(S) | : Alex Stoit et al. | |

It is certified that error appears in the above-identified patent and that said Letters Patent is hereby corrected as shown below:

Title page, item [75], lines 3-4, add the word "(deceased)" after Jan H. Reinders'.

Claim 2, col. 75, line 16, "$(C_1-C_8)$alkenyloxy" should read -- $(C_1-C_6)$alkenyloxy --.

Claim 13, col. 80, line 2, "methyl pyridine" should read -- methylpyridine --.

Signed and Sealed this
Nineteenth Day of June, 2012

David J. Kappos
*Director of the United States Patent and Trademark Office*